US012806161B2

(12) United States Patent
Freeman et al.

(10) Patent No.: US 12,806,161 B2
(45) Date of Patent: Nov. 24, 2026

(54) METHODS AND COMPOSITIONS FOR INDUCING BROWN ADIPOGENESIS

(71) Applicant: ENERGESIS PHARMACEUTICALS, INC., Cambridge, MA (US)

(72) Inventors: Brian Freeman, Cambridge, MA (US); Olivier D. Boss, Cambridge, MA (US)

(73) Assignee: ENERGESIS PHARMACEUTICALS, INC., Cambridge, MA (US)

(*) Notice: Subject to any disclaimer, the term of this patent is extended or adjusted under 35 U.S.C. 154(b) by 853 days.

(21) Appl. No.: 17/924,694

(22) PCT Filed: May 11, 2021

(86) PCT No.: PCT/US2021/031776
§ 371 (c)(1),
(2) Date: Nov. 11, 2022

(87) PCT Pub. No.: WO2021/231424
PCT Pub. Date: Nov. 18, 2021

(65) Prior Publication Data

US 2023/0190689 A1 Jun. 22, 2023

Related U.S. Application Data

(60) Provisional application No. 63/022,640, filed on May 11, 2020.

(51) Int. Cl.

| | |
|---|---|
| ***A61K 31/195*** | (2006.01) |
| ***A61K 31/38*** | (2006.01) |
| ***A61K 31/4174*** | (2006.01) |
| ***A61K 31/421*** | (2006.01) |
| ***A61P 3/04*** | (2006.01) |
| ***A61P 3/08*** | (2006.01) |

(52) U.S. Cl.
CPC ............ *A61K 31/195* (2013.01); *A61K 31/38* (2013.01); *A61K 31/4174* (2013.01); *A61K 31/421* (2013.01); *A61P 3/04* (2018.01); *A61P 3/08* (2018.01)

(58) Field of Classification Search
CPC ............. A61K 2300/00; A61K 31/195; A61K 31/38; A61K 31/4174; A61K 31/421; A61P 3/04; A61P 3/08
See application file for complete search history.

(56) References Cited

U.S. PATENT DOCUMENTS

| | | | |
|---|---|---|---|
| 7,795,310 | B2 | 9/2010 | Lee et al. |
| 2006/0069161 | A1 | 3/2006 | Lee et al. |
| 2008/0009537 | A1 | 1/2008 | Sakai |

(Continued)

FOREIGN PATENT DOCUMENTS

| | | |
|---|---|---|
| JP | 2008-505176 | 2/2008 |
| JP | 2009-149628 | 7/2008 |
| JP | 2017-507670 | 3/2017 |

OTHER PUBLICATIONS

Written Opinion in International Application No. PCT/US2021/031776, Sep. 8, 2021, pp. 1-6.

(Continued)

*Primary Examiner* — Savitha M Rao
(74) *Attorney, Agent, or Firm* — SALIWANCHIK, LLOYD & EISENSCHENK

(57) ABSTRACT

This disclosure features compositions, methods, and kits for the treatment of metabolic disorders such as diabetes and obesity.

12 Claims, 65 Drawing Sheets

Specification includes a Sequence Listing.

(56) References Cited

U.S. PATENT DOCUMENTS

| | | | |
|---|---|---|---|
| 2018/0344761 | A1 | 12/2018 | Oudshoorn |
| 2022/0331403 | A1 | 10/2022 | Boss |

OTHER PUBLICATIONS

Overby, H. et al. "Indomethacin promotes browning and brown adipotenesis in both murine and human fat cells" *Pharmacol Res Perspect.,* 2020, pp. 1-13, e00592.

Higuchi, T. et al. "Anti-tumor effects of a nonsteroidal anti-inflammatory drug zaltoprofen on chondrosarcoma via activating peroxisome proliferator-activated receptor gamma and suppressing matrix metalloproteinase-2 expression" *Cancer Medicine,* 2018, pp. 1944-1954, vol. 7, No. 5.

Ghandour, R. A. et al. "IP-receptor and PPARs trigger the conversion of human white to brite adipocyte induced by carbaprostacyclin" *Biochimica et Biophysica Acta Molecular and Cell Biology of Lipids*, 2016, pp. 1-28, vol. 1861, No. 4.

Vehicle (DMSO)

Rosiglitazone

BMP7

Rosiglitazone + BMP7

Diflunisal

Probenecid

Tianeptine

Zaltoprofen

Ozagrel

Gliquidone

Bezafibrate

Alprostadil

Oxaprozin

Indomethacin

A

B

C

Bezafibrate

Glimepiride

Ozagrel

Diflunisal

A

B

C

Alprostadil

Tianeptine

Probenecid

Gliquidone

Oxaprozin

A

B

C

Zaltoprofen

* p<0.05, ** p<0.01, 2-way ANOVA with Bonferroni's multiple comparisons test

** p<0.01
2-way ANOVA with Bonferroni's multiple comparisons test 1-way ANOVA with Bonferroni's multiple comparisons test

* $p<0.05$
1-way ANOVA with Bonferroni's multiple comparisons test 1-way ANOVA with Bonferroni's multiple comparisons test

* p<0.05
1-way ANOVA with Bonferroni's multiple comparisons test 1-way ANOVA with Bonferroni's multiple comparisons test 1-way ANOVA with Bonferroni's multiple comparisons test 1-way ANOVA with Bonferroni's multiple comparisons test

* p<0.05, 1-way ANOVA with Bonferroni's multiple comparisons test

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: UCP1 FAM-MGB probe

<400> SEQUENCE: 1

tcaaggggtt ggtaccttcc                                                20


<210> SEQ ID NO 2
<211> LENGTH: 20
<212> TYPE: DNA
<213> ORGANISM: Artificial Sequence
<220> FEATURE:
<223> OTHER INFORMATION: sense primer

<400> SEQUENCE: 2

cactaacgaa ggaccaacgg                                                20


<210> SEQ ID NO 3
<211> LENGTH: 20
<212> TYPE: DNA
<213> ORGANISM: Artificial Sequence
<220> FEATURE:
<223> OTHER INFORMATION: antisense primer

<400> SEQUENCE: 3

ttccaggatc caagtcgcaa                                                20


<210> SEQ ID NO 4
<211> LENGTH: 20
<212> TYPE: DNA
<213> ORGANISM: Artificial Sequence
<220> FEATURE:
<223> OTHER INFORMATION: Cyclophilin A NED-MGB probe

<400> SEQUENCE: 4

actgccaaga ctgagtggtt                                                20


<210> SEQ ID NO 5
<211> LENGTH: 20
<212> TYPE: DNA
<213> ORGANISM: Artificial Sequence
<220> FEATURE:
<223> OTHER INFORMATION: sense primer

<400> SEQUENCE: 5

caaatgctgg acccaacaca                                                20


<210> SEQ ID NO 6
<211> LENGTH: 20
<212> TYPE: DNA
<213> ORGANISM: Artificial Sequence
<220> FEATURE:
<223> OTHER INFORMATION: antisense primer

<400> SEQUENCE: 6

tcactttgcc aaacaccaca                                                20


<210> SEQ ID NO 7
<211> LENGTH: 22
<212> TYPE: DNA
<213> ORGANISM: Artificial Sequence
```

-continued

```
<220> FEATURE:
<223> OTHER INFORMATION: PPARgamma2 VIC-MGB probe

<400> SEQUENCE: 7

tcacaagaaa tgaccatggt tg                                              22


<210> SEQ ID NO 8
<211> LENGTH: 22
<212> TYPE: DNA
<213> ORGANISM: Artificial Sequence
<220> FEATURE:
<223> OTHER INFORMATION: sense primer

<400> SEQUENCE: 8

agcgattcct tcactgatac ac                                              22


<210> SEQ ID NO 9
<211> LENGTH: 20
<212> TYPE: DNA
<213> ORGANISM: Artificial Sequence
<220> FEATURE:
<223> OTHER INFORMATION: antisense primer

<400> SEQUENCE: 9

ccagaatggc atctctgtgt                                                 20
```

METHODS AND COMPOSITIONS FOR INDUCING BROWN ADIPOGENESIS

CROSS-REFERENCE TO RELATED APPLICATIONS

This application is the U.S. National Stage Application of International Patent Application No. PCT/US2021/031776, filed on May 11, 2021, which claims the benefit of U.S. Provisional Application Ser. No. 63/022,640, filed May 11, 2020, the disclosure of which is hereby incorporated by reference in its entirety, including all figures, tables and amino acid or nucleic acid sequences.

The Sequence Listing for this application is labeled "Seq-List.txt" which was created on May 9, 2021 and is 2 KB. The entire content of the sequence listing is incorporated herein by reference in its entirety.

STATEMENT REGARDING FEDERALLY SPONSORED RESEARCH

This invention was made with government support under R44DK109860 awarded by the National Institutes of Health. The government has certain rights in the invention.

TECHNICAL FIELD

The present disclosure relates to compositions and methods related to enhancing brown adipocytes, and/or brown adipocyte mass, in conditions such as type 2 diabetes, obesity, insulin-resistance, and dyslipidemia. Specifically, the present disclosure identifies and describes compounds that increase the differentiation of brown adipose tissue (BAT) progenitor cells isolated from skeletal muscle (CD34+ cells) into brown adipocytes. Further, the present disclosure identifies and describes compounds which interact with gene products involved in the regulation of brown adipocyte differentiation and/or mass. Still further, the present disclosure provides methods for the identification and therapeutic use of compounds for the prevention and treatment of type 2 diabetes, obesity, insulin-resistance, and dyslipidemia. The disclosure is useful for the study, prevention, and treatment of various metabolic diseases such as obesity, type 2 diabetes, insulin-resistance and dyslipidemia.

BACKGROUND

The epidemic of obesity is closely associated with increases in the prevalence of diabetes, hypertension, coronary heart disease, cancer and other disorders. The role of white adipose tissue is to store lipids, and it is associated with obesity. The role of brown adipose tissue ("BAT") is effectively the opposite. It is specialized in lipid combustion and the dissipation of energy as heat. Indeed, the brown adipocyte contains numerous mitochondria (in which cellular combustion occurs) and uniquely expresses uncoupling protein-1 ("UCP1"). UCP1 acts as an uncoupler of oxidative phosphorylation, resulting in dissipation of energy as heat. The sympathetic nervous system stimulates mitochondriogenesis and UCP1 expression and activity. BAT-associated thermogenesis in rodents is increased upon exposure to low temperature (e.g., preventing hypothermia) or as a result of overeating, burning excess absorbed fat and preventing weight gain. BAT, by modifying susceptibility to weight gain and by consuming large amounts of glucose, also improves insulin sensitivity. It therefore plays an important role in the maintenance of body temperature, energy balance and glucose metabolism.

Experiments with transgenic animals support the potential anti-obesity properties of BAT. For example, the genetic ablation of BAT has been reported to cause obesity, while genetic increase in the amount and/or function of BAT (and/or UCP1 expression) reportedly promotes a lean and healthy phenotype. Specifically, mice with a higher amount of BAT gain less weight and are more insulin-sensitive than control mice. Recently, ectopic BAT depots were evidenced in the mouse muscle, which have been shown to provide a genetic mechanism of protection from weight gain and metabolic syndrome.

Although UCP1 is reported to play a role in the control of energy balance in rodents and UCP1-expressing BAT is present in human neonates, it has long been thought that there was no physiologically relevant UCP1 expression in adult humans. Indeed, UCP1-expressing BAT was thought to disappear early in life, and adult humans were thought to be devoid of BAT. Recently however, numerous studies have demonstrated that BAT is indeed maintained in most adult humans, albeit at considerably lower levels than in neonates and children.

As such, a need exists to carefully identify and study ways to provide more BAT in the adult body and/or stimulate UCP1 expression, for the study, prevention and treatment of various metabolic diseases such as obesity, type 2 diabetes, insulin-resistance, dyslipidemia and type 1 diabetes.

SUMMARY

The present disclosure provides compositions for recruiting brown adipocytes in vitro and in vivo from BAT progenitor cells found in human skeletal muscle. These agents, or combinations thereof, can be used to promote the differentiation of BAT progenitor cells into brown adipocytes and/or induce the expression of UCP1, FABP4 (αP2), PPARγ2, mtTFA, PGC-1α, and/or COX IV in BAT progenitor cells in vitro, in vivo, or both. Furthermore, these agents can be used to treat metabolic disease, including obesity, excess body fat, overweight, diabetes, hyperglycemia, insulin resistance, hyperlipidemia, and others conditions in a patient.

The present disclosure is based, in part, on the discovery that various mechanisms are involved in the differentiation of BAT progenitor cells and the hypothesis that screening diverse compounds could identify some that effectively recruit brown adipocytes. In particular, it has been found that the various compounds disclosed herein markedly induce differentiation of BAT progenitor cells isolated from human skeletal muscle into mature, functional brown adipocytes. Treatment of BAT progenitor cells with one or more of these various compounds triggers commitment of these cells to brown adipocyte differentiation.

In addition, it has been found that two different compounds used together can have additive or synergistic effects on the differentiation of the progenitor cells into brown adipocytes, such that the effect is greater than the effect that can be obtained with either compound alone.

In some cases, treatment with one or more compounds for 3 days prior to the introduction of an adipogenic medium results in brown adipocyte differentiation. In other cases, treatment with one or more compounds for 3 days contemporaneously with the introduction of adipogenic medium results in brown adipocyte differentiation.

Since brown adipose tissue (BAT) is specialized for energy expenditure, the methods described herein are useful for the treatment of obesity and related disorders, such as diabetes. The methods can also be used to decrease fat stores in subjects including food animals, e.g., to improve the quality of the meat derived therefrom.

Accordingly, in one aspect, the disclosure features methods of treating a subject, e.g., decreasing fat stores or weight in a subject such as a human. The methods include administering to the subject a compound or combination of compounds disclosed herein. In a further aspect, the disclosure features methods of administering a population of compound-activated BAT progenitor cells, wherein said population of compound-activated progenitor cells undergo brown adipogenesis. The methods can optionally include identifying a subject in need of decreasing fat stores or weight. In a further aspect, the disclosure includes methods of enhancing insulin sensitivity in a subject, e.g., a subject that is insulin-resistant. The methods include administering to the subject a compound, or a population of compound-activated BAT progenitor cells, wherein said population of compound-activated BAT progenitor cells undergo brown adipogenesis. The methods can optionally include identifying a subject in need of enhanced insulin sensitivity.

In another aspect, the disclosure features methods of modulating brown adipose tissue function or development, e.g., promoting BAT adipogenesis, in a subject. The methods include administering to the subject a compound or population of compound-activated BAT progenitor cells, wherein said population of compound-activated progenitor cells undergo brown adipogenesis.

As used herein, “compound-activated” means that the BAT progenitor cell or cells have been treated with the compound as described herein. The cells can be autologous, allogeneic, or xenogeneic.

In some embodiments, methods described herein can include implanting a population of compound-activated BAT progenitor cells into a subject. The compound-activated cells can be implanted directly or can be administered in a scaffold, matrix, or other implantable device to which the cells can attach (examples include carriers made of, e.g., collagen, fibronectin, elastin, cellulose acetate, cellulose nitrate, polysaccharide, fibrin, gelatin, self-assembling small peptides, and combinations thereof). In general, the methods include implanting a population of compound-activated BAT progenitor cells comprising a sufficient number of cells to promote increased brown adipocyte mass in the subject, e.g., to increase the amount of brown adipocytes in the subject by at least 1%, e.g., 2%, 5%, 7%, 10%, 15%, 20%, 25% or more.

In some embodiments, the methods include evaluating the level of BAT adipogenesis in a subject, by contacting isolated BAT progenitor cells from a subject with one or more of the compounds disclosed herein. BAT differentiation can be evaluated by measuring any of, e.g., a BAT marker, such as uncoupling protein (UCP), e.g., UCP-I, expression; BAT morphology (e.g., using visual, e.g., microscopic, inspection of the cells); or BAT thermodynamics, e.g., cytochrome oxidase activity, Na+–K+– ATPase enzyme units, or other enzymes involved in BAT thermogenesis.

In general, the subject is a mammal. In some embodiments, the subject is a human subject, e.g., an obese human subject. In some embodiments, the subject is a non-human mammal, e.g., an experimental animal, a companion animal, or a food animal, e.g., a cow, pig, or sheep that is raised for food. In some embodiments, the methods include evaluating the subject for one or more of: weight, white adipose tissue stores, brown adipose tissue stores, adipose tissue morphology, insulin levels, insulin metabolism, glucose levels, thermogenic capacity, and cold sensitivity. The evaluation can be performed before, during, and/or after the administration of the compound or compound-activated BAT progenitor cells. For example, the evaluation can be performed at least 1 day, 2 days, 4, 7, 14, 21, 30 or more days before and/or after the administration.

In some embodiments, the methods include one or more additional rounds of treatment with a compound or implantation of compound-activated BAT progenitor cells, e.g., to increase brown adipocyte mass, e.g., to maintain or further reduce obesity in the subject.

In some embodiments, the disclosure features a composition that includes (a) bezafibrate or an analog thereof and (b) oxaprozin or an analog thereof, wherein the bezafibrate and oxaprozin or analogs thereof are present in amounts that, when administered to a patient, are sufficient to treat, prevent, or reduce a metabolic disorder (e.g., obesity or diabetes).

In other embodiments, the disclosure features a composition that includes (a) bezafibrate or an analog thereof and (b) zaltoprofen or an analog thereof, wherein the bezafibrate and zaltoprofen or analogs thereof are present in amounts that, when administered to a patient, are sufficient to treat, prevent, or reduce a metabolic disorder (e.g., obesity or diabetes).

In still other embodiments, the disclosure features a composition that includes (a) bezafibrate or an analog thereof and (b) ozagrel or an analog thereof, wherein the bezafibrate and ozagrel or analogs thereof are present in amounts that, when administered to a patient, are sufficient to treat, prevent, or reduce a metabolic disorder (e.g., obesity or diabetes).

The compositions of the disclosure may be formulated for local administration or systemic administration. If more than one agent is employed, therapeutic agents may be delivered separately or may be admixed into a single formulation. When agents are present in different pharmaceutical compositions, different routes of administration may be employed. Routes of administration for the various embodiments include, but are not limited to, topical, transdermal, and systemic administration (such as, intravenous, intramuscular, Subcutaneous, inhalation, rectal, buccal, vaginal, intraperitoneal, intraarticular, ophthalmic or oral administration). As used herein, “systemic administration” refers to all nondermal routes of administration, and specifically excludes topical and transdermal routes of administration. Desirably, the agent of the disclosure and additional therapeutic agents are administered within at least 1, 2, 4, 6, 10, 12, 18, 24 hours, 3 days, 7 days, 10 days, or 14 days apart. The dosage and frequency of administration of each component of the combination can be controlled independently. For example, one compound may be administered three times per day, while the second compound may be administered once per day. Combination therapy may be given in on-and-off cycles that include rest periods so that the patient’s body has a chance to recover from any as yet unforeseen side effects. The compounds may also be formulated together such that one administration delivers both compounds. Optionally, any of the agents of the combination may be administered in a low dosage or in a high dosage, each of which is defined herein.

Generally, when administered to a human, the dosage of any of the agents of the combination of the disclosure will depend on the nature of the agent, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 2000 mg per day may be necessary. Administration of each drug in the combination can, independently, be one to four times daily for one day to one year, and may even be for the life of the patient. Chronic, long-term administration will be indicated in many cases. In various embodiments, a therapeutically effective amount of bezafibrate ranges from about 100 mg to about 400 mg, about 100 mg to about 300 mg, or about 5 mg to about 500 mg, and a therapeutically effective amount of oxaprozin ranges from about 300 mg to about 900 mg, about 300 mg to about 1200 mg, or about 5 mg to about 500 mg.

The therapeutic agents of the disclosure may be admixed with additional active or inert ingredients, e.g., in conventional pharmaceutically acceptable carriers. A pharmaceutical carrier can be any compatible, non-toxic substance suitable for the administration of the compositions of the present disclosure to a mammal. Pharmaceutically acceptable carriers include, for example, water, saline, buffers, and other compounds described for example in the Merck Index, Merck & Co., Rahway, N.J. Slow release formulation or a slow release apparatus may also be used for continuous administration.

If more than one agent is employed, each agent may be formulated in a variety of ways that are known in the art. Desirably, the agents are formulated together for the simultaneous or near simultaneous administration of the agents. Such co-formulated compositions can include the two agents formulated together in the same pill, capsule, liquid, etc. It is to be understood that, when referring to the formulation of such combinations, the formulation technology employed is also useful for the formulation of the individual agents of the combination, as well as other combinations of the disclosure. By using different formulation strategies for different agents, the pharmacokinetic profiles for each agent can be suitably matched.

The methods of this disclosure may also be used prophylactically, in patients who are an increased risk of developing obesity, diabetes or a condition associated with obesity or diabetes such as insulin resistance. Risk factors include for example, family history of diabetes or obesity or associated conditions, quality of nutrition, level of physical activity, presence of molecular markers of obesity or diabetes, age, race, or sex. Patients affected with other non-related disorders may also be predisposed to secondary obesity or diabetes.

The disclosure also features a method for treating, preventing, or reducing a metabolic disorder in a patient in need thereof by administering to the patient (i) bezafibrate or an analog thereof and (ii) oxaprozin or an analog thereof, wherein the bezafibrate and oxaprozin or analogs thereof are administered in amounts that together are sufficient to treat, prevent, or reduce a metabolic disorder.

The disclosure also features a method for treating, preventing, or reducing a metabolic disorder in a patient in need thereof by administering to the patient (i) bezafibrate or an analog thereof and (ii) zaltoprofen or an analog thereof, wherein the bezafibrate and zaltoprofen or analogs thereof are administered in amounts that together are sufficient to treat, prevent, or reduce a metabolic disorder.

The disclosure also features a method for treating, preventing, or reducing a metabolic disorder in a patient in need thereof by administering to the patient (i) bezafibrate or an analog thereof and (ii) ozagrel or an analog thereof, wherein the bezafibrate and ozagrel or analogs thereof are administered in amounts that together are sufficient to treat, prevent, or reduce a metabolic disorder.

The individually or separately formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blisterpacks, bottles, tubes, and the like.

The disclosure also features a kit that includes (i) bezafibrate or an analog thereof and (ii) instructions for administering bezafibrate and oxaprozin or analogs thereof to a patient having or at risk of having a metabolic disorder.

The disclosure also features a kit that includes (i) oxaprozin or an analog thereof and (ii) instructions for administering oxaprozin and bezafibrate or analogs thereof to a patient having or at risk of having a metabolic disorder.

The disclosure also features a kit that includes (i) bezafibrate or an analog thereof and (ii) instructions for administering bezafibrate and zaltoprofen or analogs thereof to a patient having or at risk of having a metabolic disorder.

The disclosure also features a kit that includes (i) zaltoprofen or an analog thereof and (ii) instructions for administering zaltoprofen and bezafibrate or analogs thereof to a patient having or at risk of having a metabolic disorder.

The disclosure also features a kit that includes (i) bezafibrate or an analog thereof and (ii) instructions for administering bezafibrate and ozagrel or analogs thereof to a patient having or at risk of having a metabolic disorder.

The disclosure also features a kit that includes (i) ozagrel or an analog thereof and (ii) instructions for administering ozagrel and bezafibrate or analogs thereof to a patient having or at risk of having a metabolic disorder.

The disclosure also features a kit that includes (i) a composition containing bezafibrate or an analog thereof and oxaprozin or an analog thereof and (ii) instructions for administering the composition to a patient having or at risk of having a metabolic disorder.

The disclosure also features a kit that includes (i) a composition containing bezafibrate or an analog thereof and zaltoprofen or an analog thereof and (ii) instructions for administering the composition to a patient having or at risk of having a metabolic disorder.

The disclosure also features a kit that includes (i) a composition containing bezafibrate or an analog thereof and ozagrel or an analog thereof and (ii) instructions for administering the composition to a patient having or at risk of having a metabolic disorder.

The disclosure also features a kit that includes (i) bezafibrate or an analog thereof (ii) oxaprozin or an analog thereof, and (iii) instructions for administering bezafibrate and oxaprozin or analogs thereof to a patient having or at risk of having a metabolic disorder.

The disclosure also features a kit that includes (i) bezafibrate or an analog thereof (ii) zaltoprofen or an analog thereof, and (iii) instructions for administering bezafibrate and zaltoprofen or analogs thereof to a patient having or at risk of having a metabolic disorder.

The disclosure also features a kit that includes (i) bezafibrate or an analog thereof (ii) ozagrel or an analog thereof, and (iii) instructions for administering bezafibrate and ozagrel tor analogs thereof to a patient having or at risk of having a metabolic disorder.

The disclosure also features a composition that includes (a) a PPAR agonist (activator); and (b) oxaprozin, wherein the PPAR activator and oxaprozin are present in amounts that, when administered to a patient, are sufficient to treat, prevent, or reduce a metabolic disorder.

The disclosure also features a composition that includes (a) a PPAR agonist and (b) zaltoprofen or an analog thereof, wherein the PPAR activator and zaltoprofen or analog thereof are present in amounts that, when administered to a patient, are sufficient to treat, prevent, or reduce a metabolic disorder.

The disclosure also features a composition that includes (a) a PPAR activator agonist and (b) ozagrel or an analog thereof, wherein the PPAR activator and ozagrel or analog thereof are present in amounts that, when administered to a patient, are sufficient to treat, prevent, or reduce a metabolic disorder.

The disclosure also features a method for treating, preventing, or reducing a metabolic disorder in a patient in need thereof by administering to the patient (i) a PPAR agonist; and (ii) oxaprozin or an analog thereof, wherein the PPAR agonist and oxaprozin or analog thereof are administered in amounts that together are sufficient to treat, prevent, or reduce a metabolic disorder.

The disclosure also features a method for treating, preventing, or reducing a metabolic disorder in a patient in need thereof by administering to the patient (i) a PPAR agonist; and (ii) zaltoprofen or an analog thereof, wherein the PPAR agonist and zaltoprofen or analog thereof are administered in amounts that together are sufficient to treat, prevent, or reduce a metabolic disorder.

The disclosure also features a method for treating, preventing, or reducing a metabolic disorder in a patient in need thereof by administering to the patient (i) a PPAR agonist; and (ii) ozagrel or an analog thereof, wherein the PPAR agonist and ozagrel or analog thereof are administered in amounts that together are sufficient to treat, prevent, or reduce a metabolic disorder.

The disclosure features a kit that includes (i) a PPAR agonist; and (ii) instructions for administering the PPAR agonist and oxaprozin or an analog thereof to a patient having or at risk of having a metabolic disorder.

The disclosure features a kit that includes (i) oxaprozin or an analog thereof and (ii) instructions for administering oxaprozin or analog thereof and a PPAR agonist to a patient having or at risk of having a metabolic disorder.

The disclosure features a kit that includes (i) a PPAR agonist; and (ii) instructions for administering the PPAR agonist and zaltoprofen or an analog thereof to a patient having or at risk of having a metabolic disorder.

The disclosure features a kit that includes (i) zaltoprofen or an analog thereof and (ii) instructions for administering zaltoprofen or an analog thereof and a PPAR agonist to a patient having or at risk of having a metabolic disorder.

The disclosure features a kit that includes (i) a PPAR agonist; and (ii) instructions for administering the PPAR agonist and ozagrel or an analog thereof to a patient having or at risk of having a metabolic disorder.

The disclosure features a kit that includes (i) ozagrel or an analog thereof and (ii) instructions for administering ozagrel or an analog thereof and a PPAR agonist to a patient having or at risk of having a metabolic disorder.

The disclosure also features a kit that includes (i) a composition containing a PPAR agonist and oxaprozin or an analog thereof, and (ii) instructions for administering the composition to a patient having or at risk of having a metabolic disorder.

The disclosure also features a kit that includes (i) a composition containing a PPAR agonist and zaltoprofen or an analog thereof, and (ii) instructions for administering the composition to a patient having or at risk of having a metabolic disorder.

The disclosure also features a kit that includes (i) a composition containing a PPAR agonist and ozagrel or an analog thereof, and (ii) instructions for administering the composition to a patient having or at risk of having a metabolic disorder.

The disclosure also features a kit that includes (i) a PPAR agonist; (ii) oxaprozin or an analog thereof; and (iii) instructions for administering the PPAR agonist and oxaprozin or analog thereof to a patient having or at risk of having a metabolic disorder.

The disclosure also features a kit that includes (i) a PPAR agonist; (ii) zaltoprofen or an analog thereof; and (iii) instructions for administering the PPAR agonist and zaltoprofen or analog thereof to a patient having or at risk of having a metabolic disorder.

The disclosure also features a kit that includes (i) a PPAR agonist; (ii) ozagrel or an analog thereof; and (iii) instructions for administering the PPAR agonist and ozagrel or analog thereof to a patient having or at risk of having a metabolic disorder.

a. Adipocyte scores as determined by light microscopy of multilocular lipid-containing cells (on a per-well basis) at the end of the differentiation of the cells, approximately 6 to 12 days following the end of compound treatment and switch into MDM media. Concentrations are in μM.
b. Expression of PPARγ2 mRNA (on a per-well basis) at the end of the differentiation of the cells, approximately 6 to 12 days following the end of compound treatment and switch into MDM media. Concentrations are in μM. Y axis units are percent of vehicle-treated cells.
c. Expression of UCP1 mRNA (on a per-well basis) at the end of the differentiation of the cells, approximately 6 to 12 days following the end of compound treatment and switch into MDM media. Concentrations are in μM.

Figure 1:
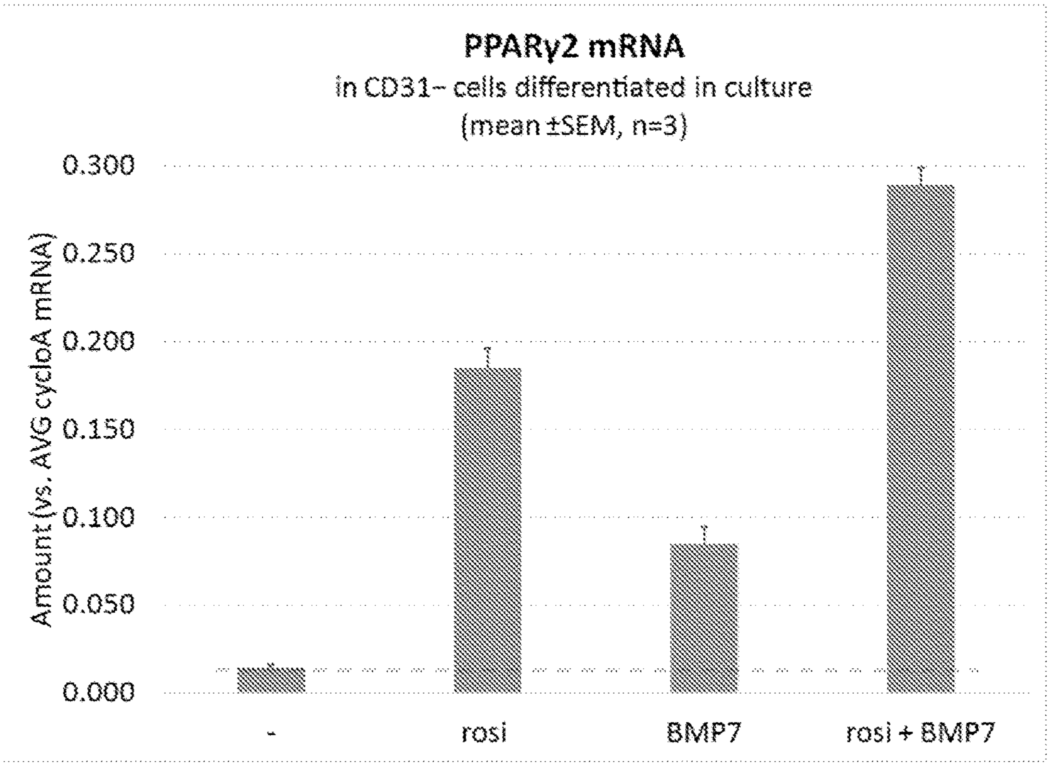
FIG. 1 shows the effects of a maximally efficacious concentration of rosiglitazone (1 μM), BMP7 (6 nM) or the combination of both agents (incubated with brown adipocyte progenitor cells at day −3 to d0) on the expression of PPARγ2 mRNA. p=0.0001 for rosi vs.−(vehicle), p=0.0025 for BMP7 vs.−(vehicle), p=0.0001 for rosi+BMP7 vs.−(vehicle), p=0.0024 for rosi+BMP7 vs. rosi, p=0.0001 for rosi+BMP7 vs. BMP7. (unpaired t test, two-tailed).
Figure 2:
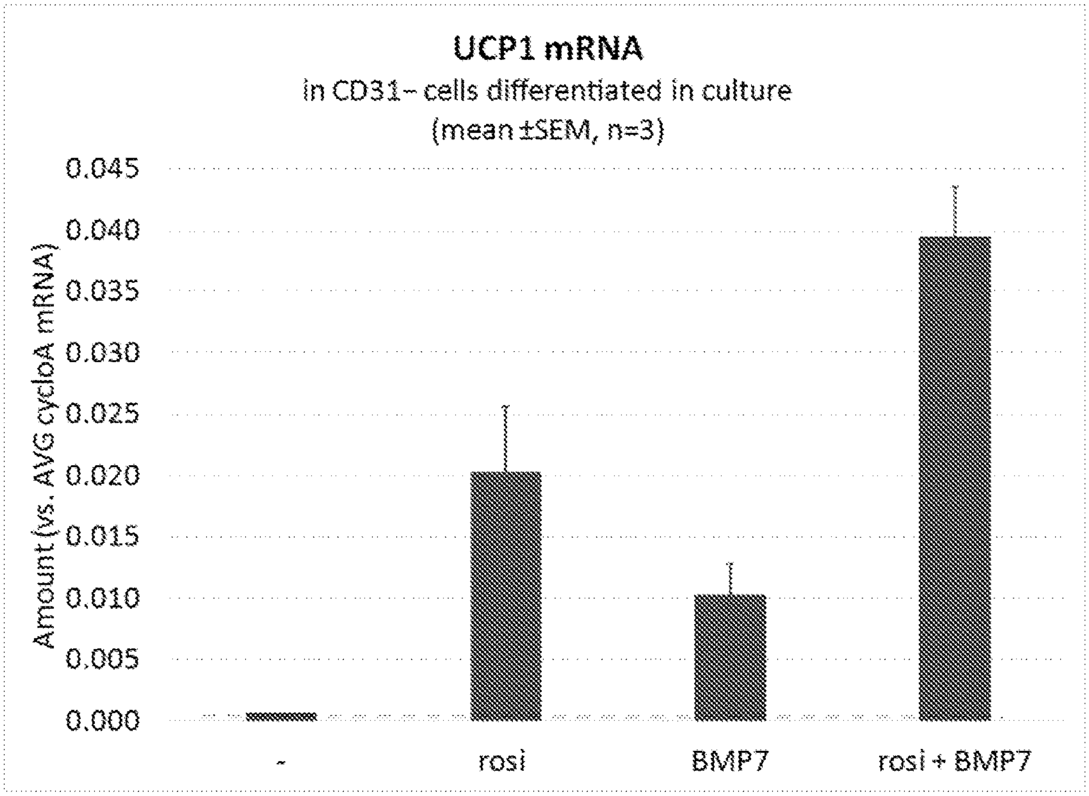
FIG. 2 shows the effects of a maximally efficacious concentration of rosiglitazone (1 μM), BMP7 (6 nM) or the combination of both agents (incubated with brown adipocyte progenitor cells at day −3 to d0) on the expression of UCP1 mRNA. p=0.021 for rosi vs.−(vehicle), p=0.018 for BMP7 vs.−(vehicle), p=0.0006 for rosi+BMP7 vs.−(vehicle), p=0.045 for rosi+BMP7 vs. rosi, p=0.004 for rosi+BMP7 vs. BMP7.
Figure 3A:
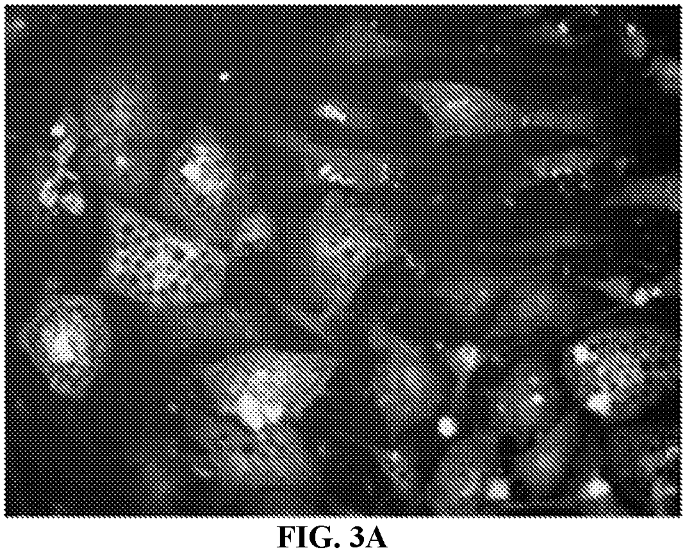
FIGS. 3A-3C show fluorescence microscopy illustrating the immmuno-histo-chemistry (IHC) assay results for UCP1 protein expression (FITC, green) and cell nuclei numbers (DAPI, blue). CD34+ cells differentiated for 8 days in minimal differentiation medium (MDM) after exposure to rosiglitazone (1 μM) differentiate profoundly into brown adipocytes expressing high levels of UCP1 (FIG. 3A), whereas cells not exposed to rosiglitazone show a much lower level of differentiation and UCP1 expression (FIG. 3B). Cells maintained in proliferation medium (EGM-2) do not differentiate and express no UCP1 (FIG. 3C).
Figure 3B:
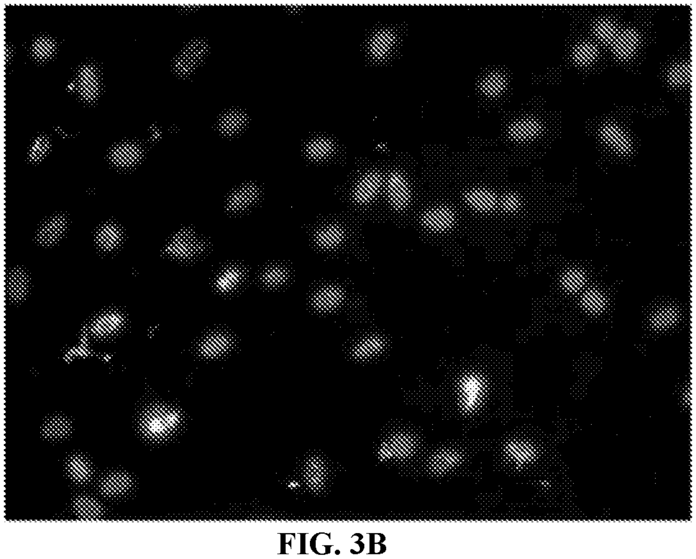
Figure 3C:
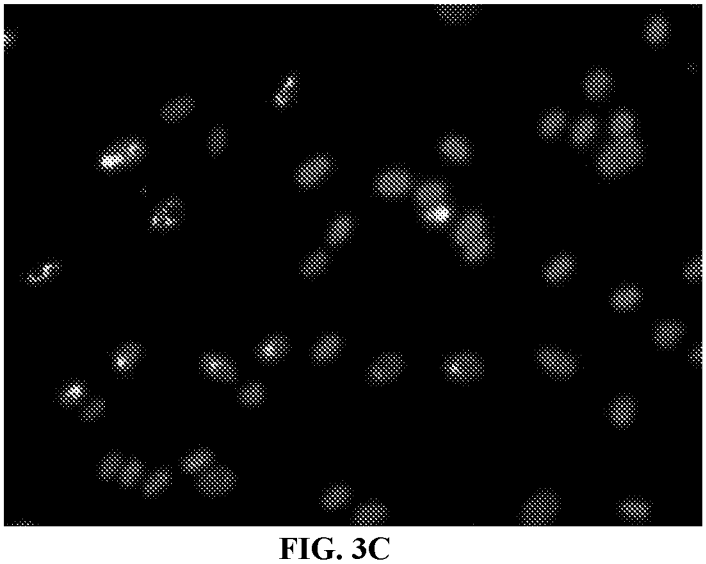
Figure 4:
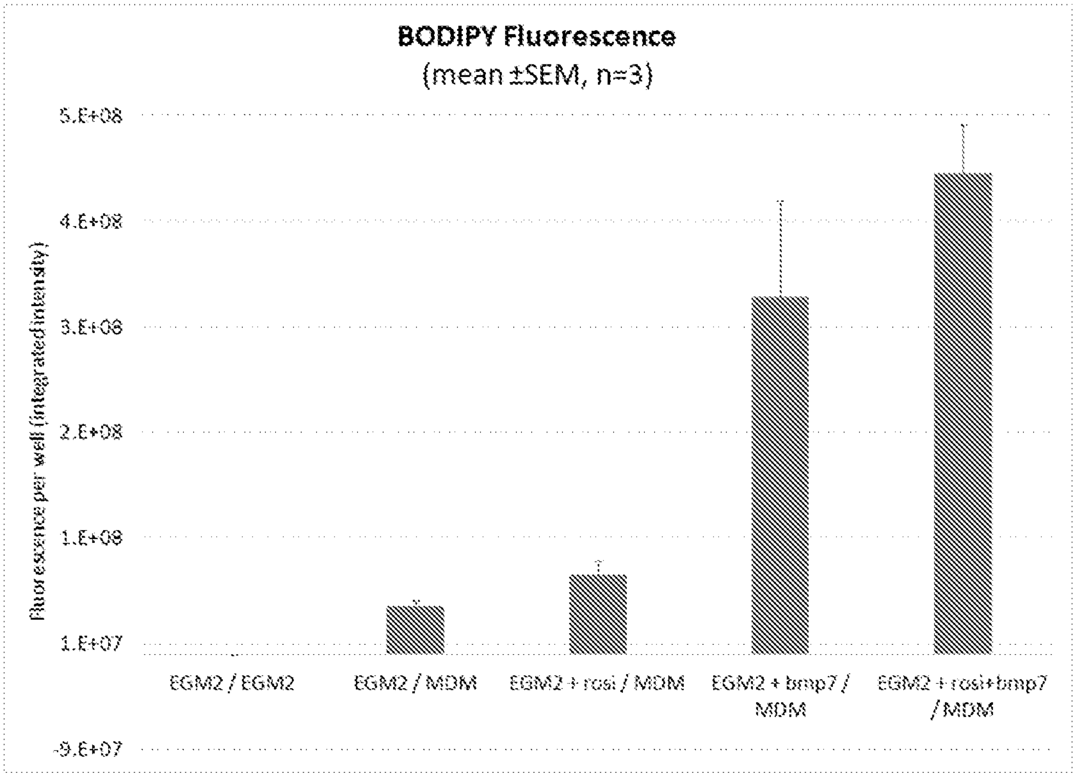
FIG. 4 shows BODIPY 500/510 C1, C12 fluorescence signal after brown adipocyte progenitor cells were induced to differentiate in culture for 9 days in various conditions (rosiglitazone and BMP7 were used from day −3 to d0).
Figure 5:
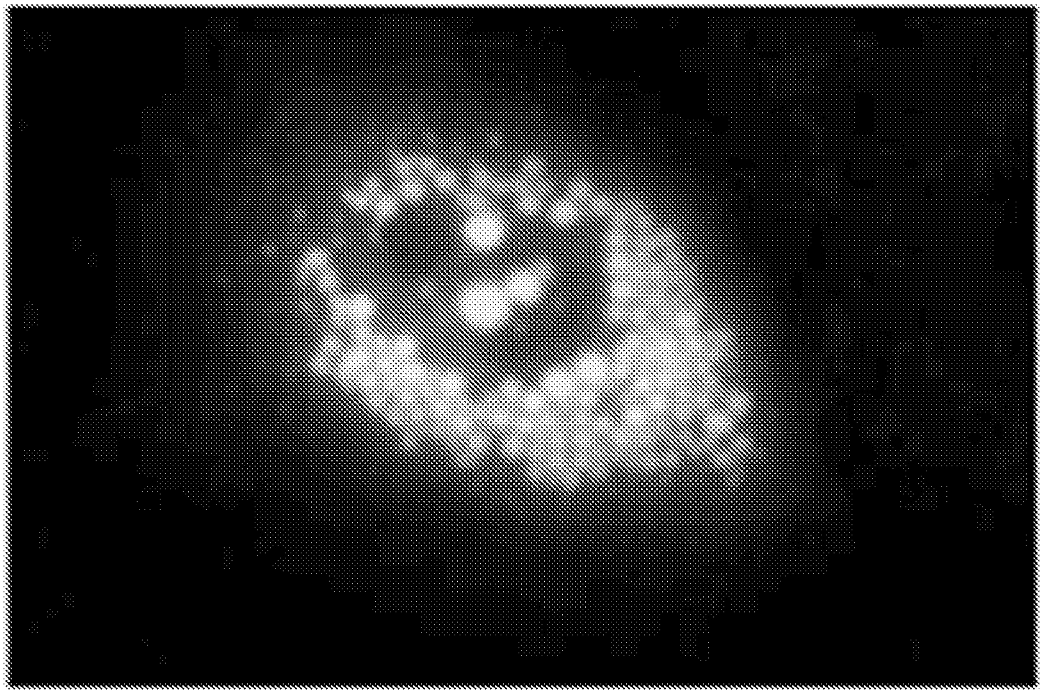
FIG. 5 shows fluorescence microscopy pictures illustrating the BODIPY assay results for intracellular lipid droplets (BODIPY 500/510 C1, C12, green). CD34+ cells were differentiated for 8 days in minimal differentiation medium (MDM) after exposure to rosiglitazone (1 μM) for 3 days (day −3 to day 0).
Figure 6A:
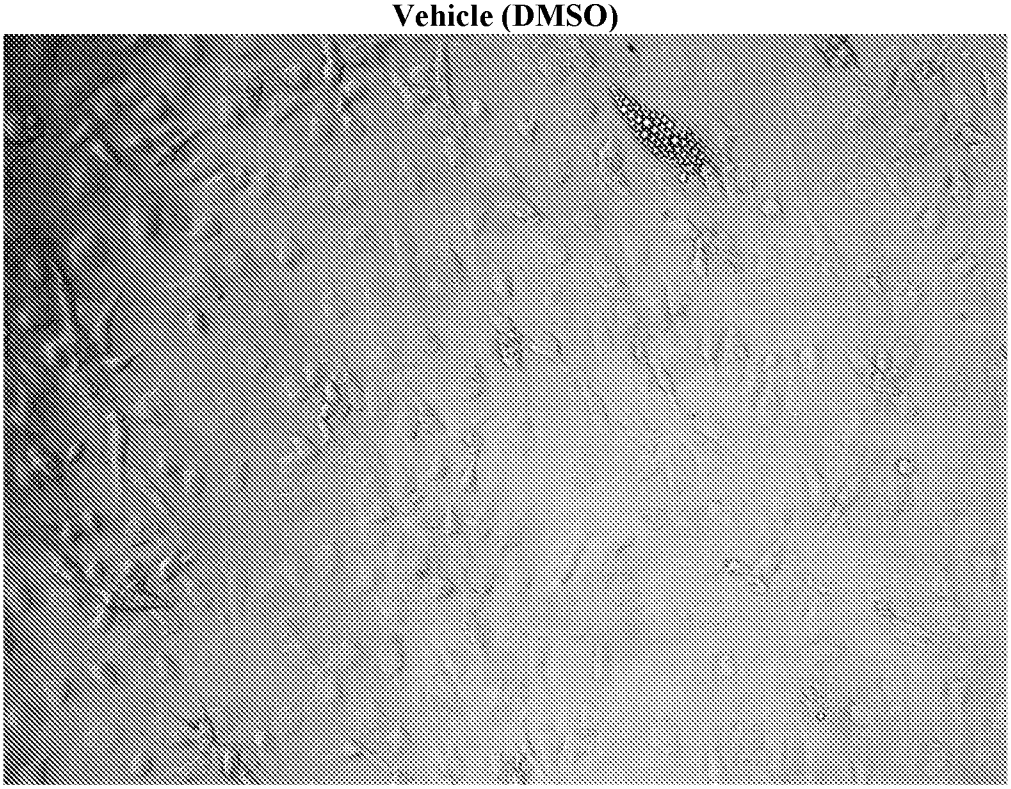
FIGS. 6A-6G show light microscopy of CD34+ cells and brown adipocyte differentiation following treatment with several compounds (FIG. 6A) vehicle, rosiglitazone, (FIG. 6B) BMP7, the combination of rosiglitazone and BMP7, (FIG. 6C) diflunisal, probenecid, (FIG. 6D) tianeptine, zaltoprofen, (FIG. 6E) ozagrel, gliquidone, (FIG. 6F) bezafibrate, alprostadil, (FIG. 6G) oxaprozin that promote brown adipocyte formation. All feature CD34+ cells 6 days following the end of compound treatment and switch into MDM media.
Figure 6A:
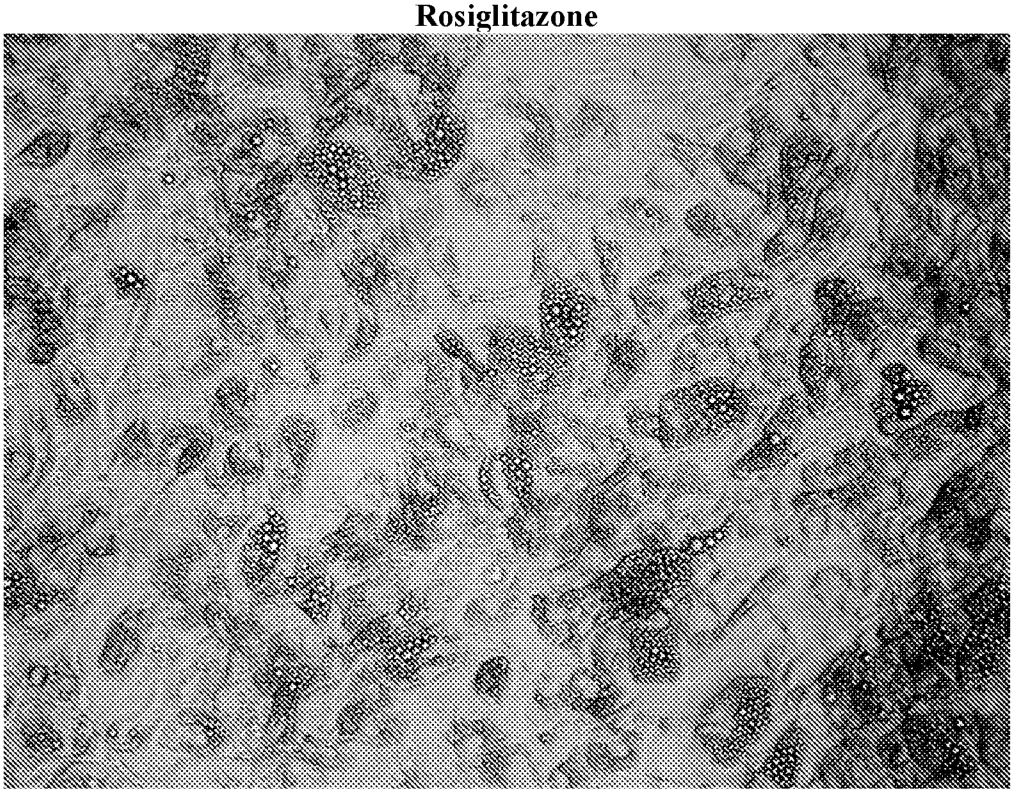
Figure 6B:
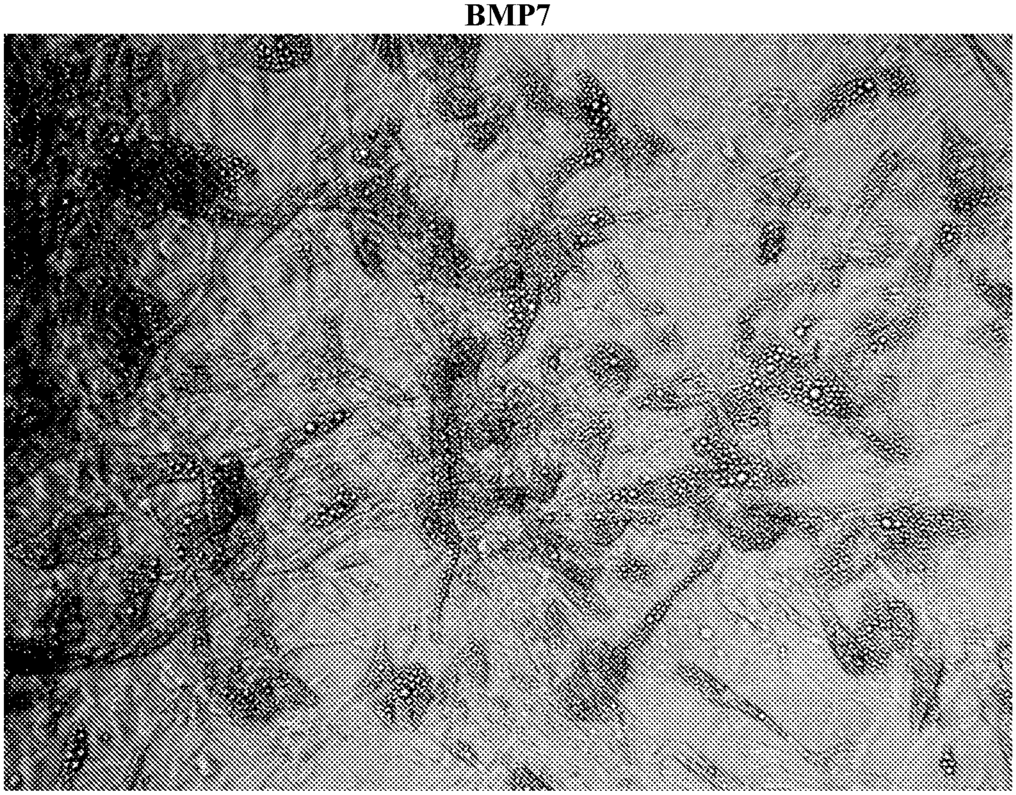
Figure 6B:
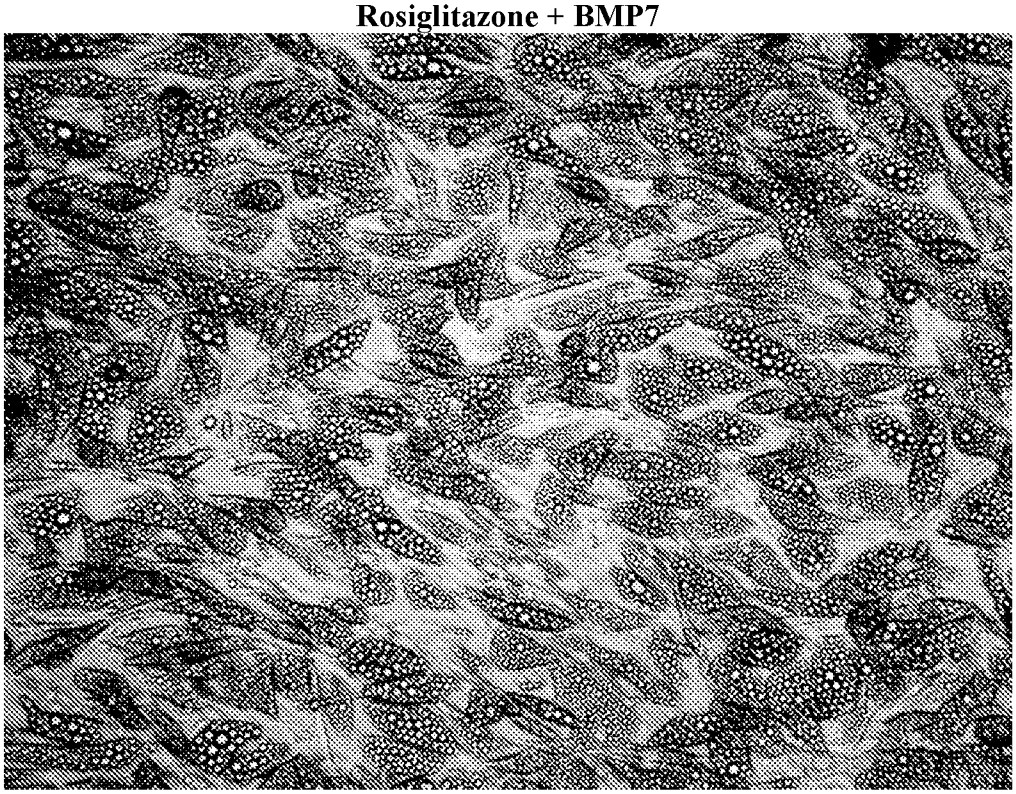
Figure 6C:
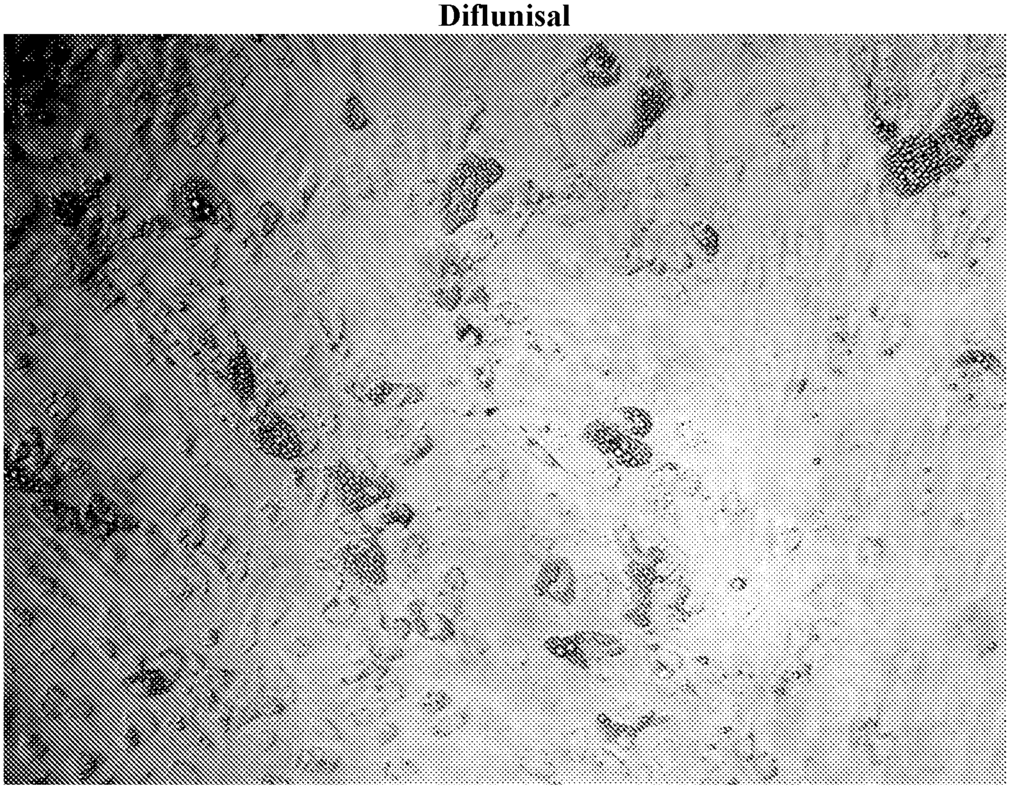
Figure 6C:
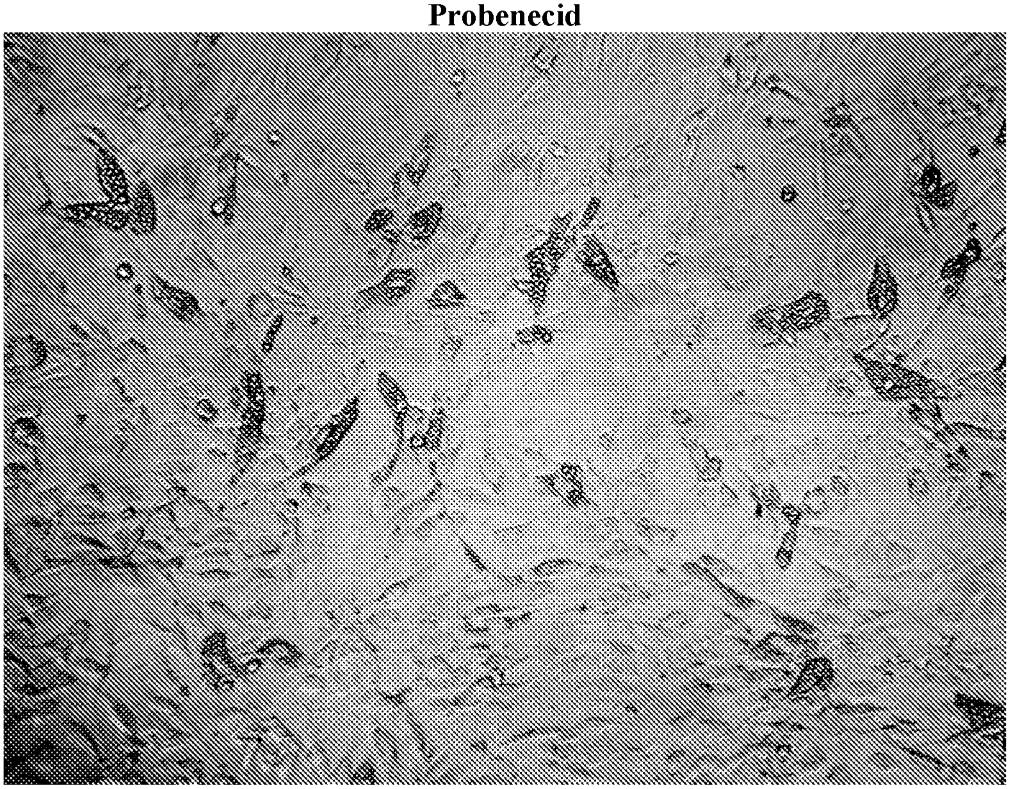
Figure 6D:
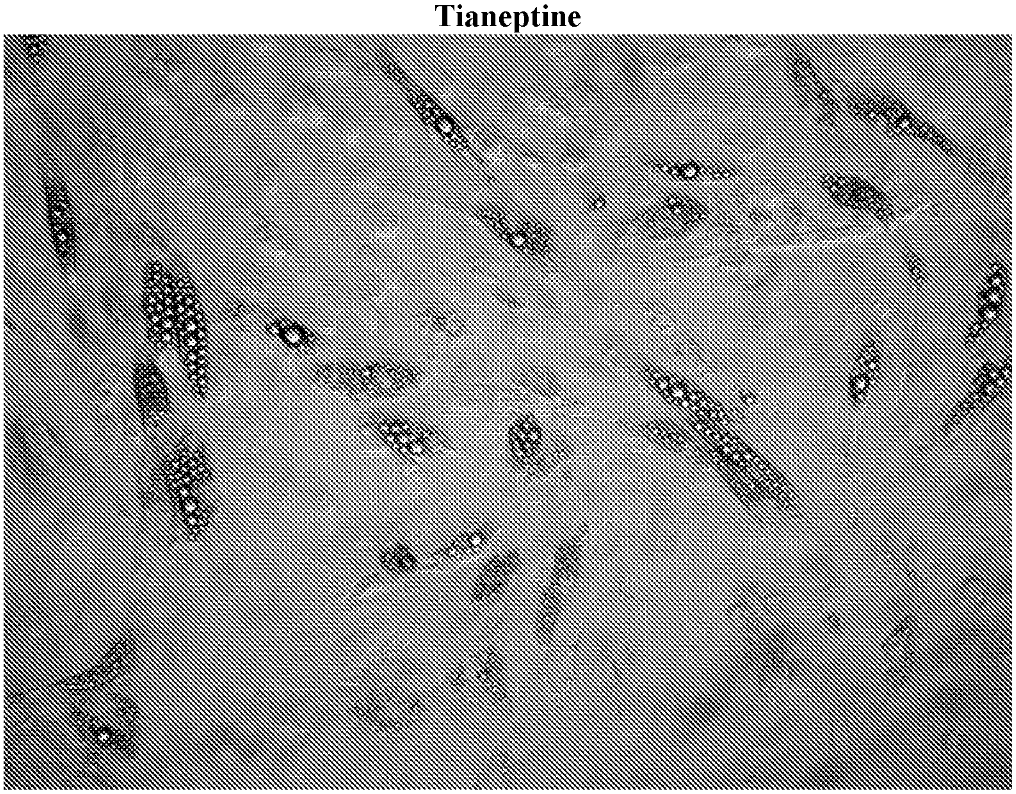
Figure 6D:
Figure 6E:
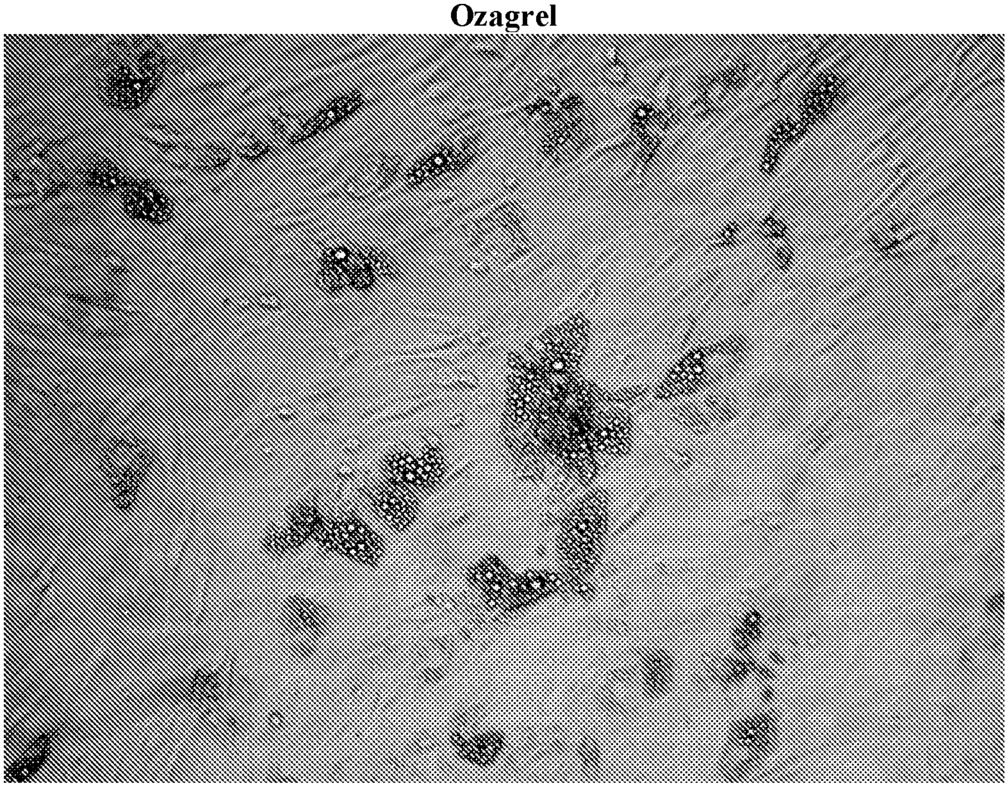
Figure 6E:
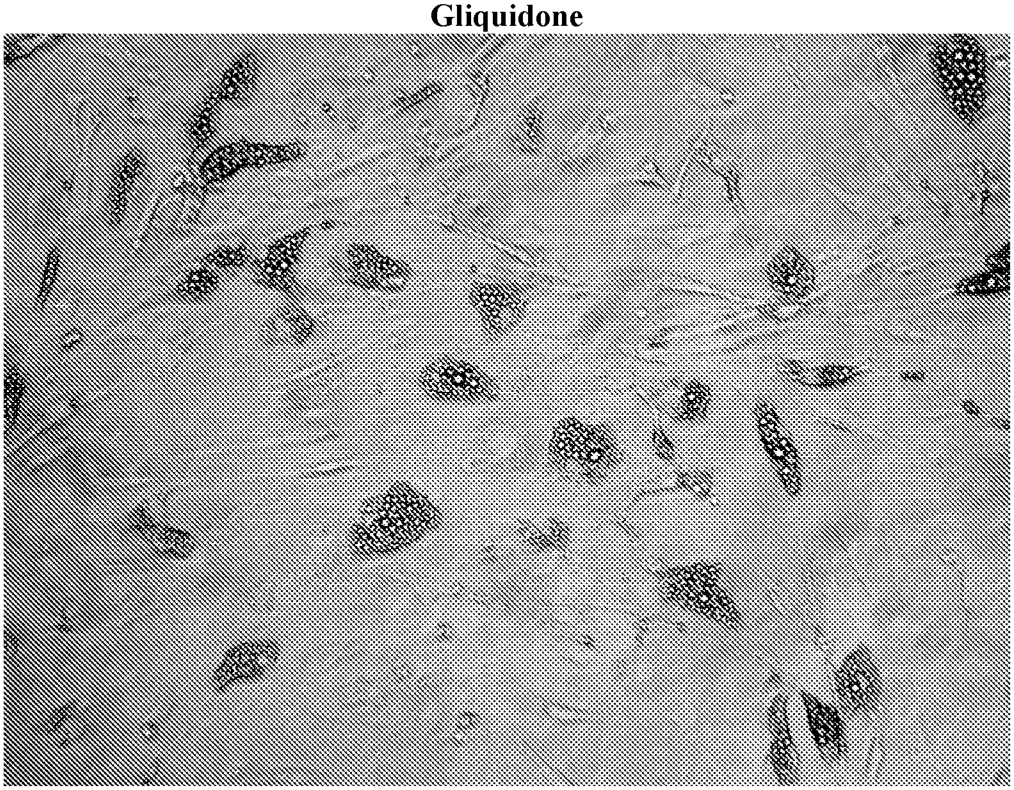
Figure 6F:
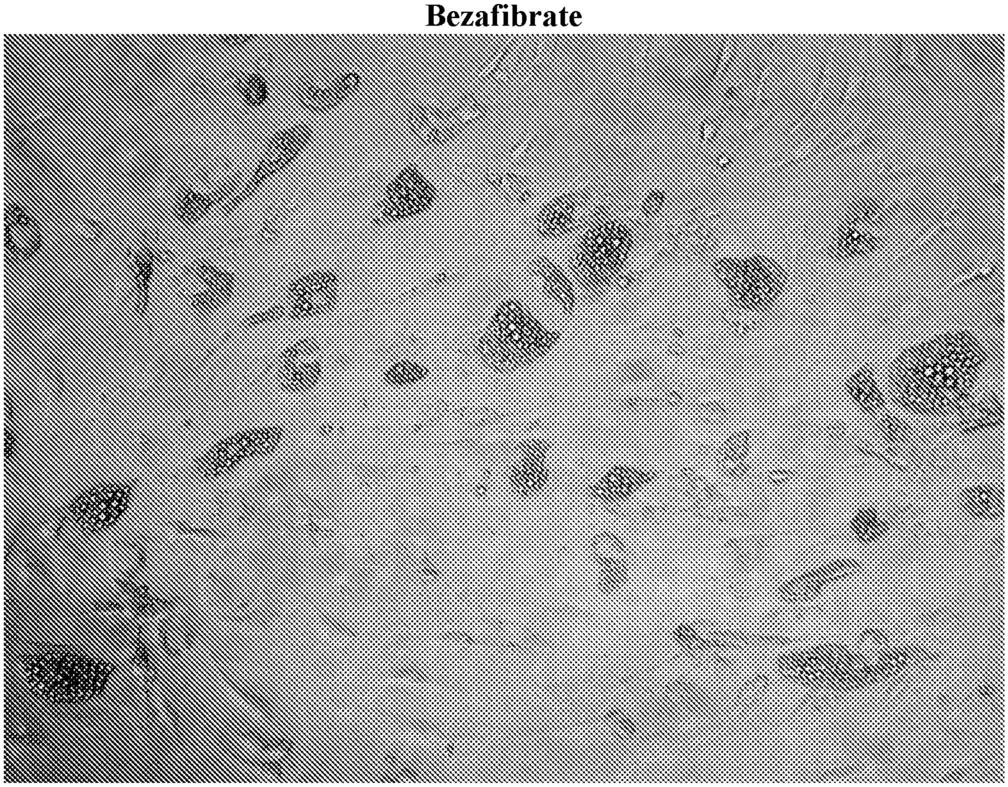
Figure 6F:
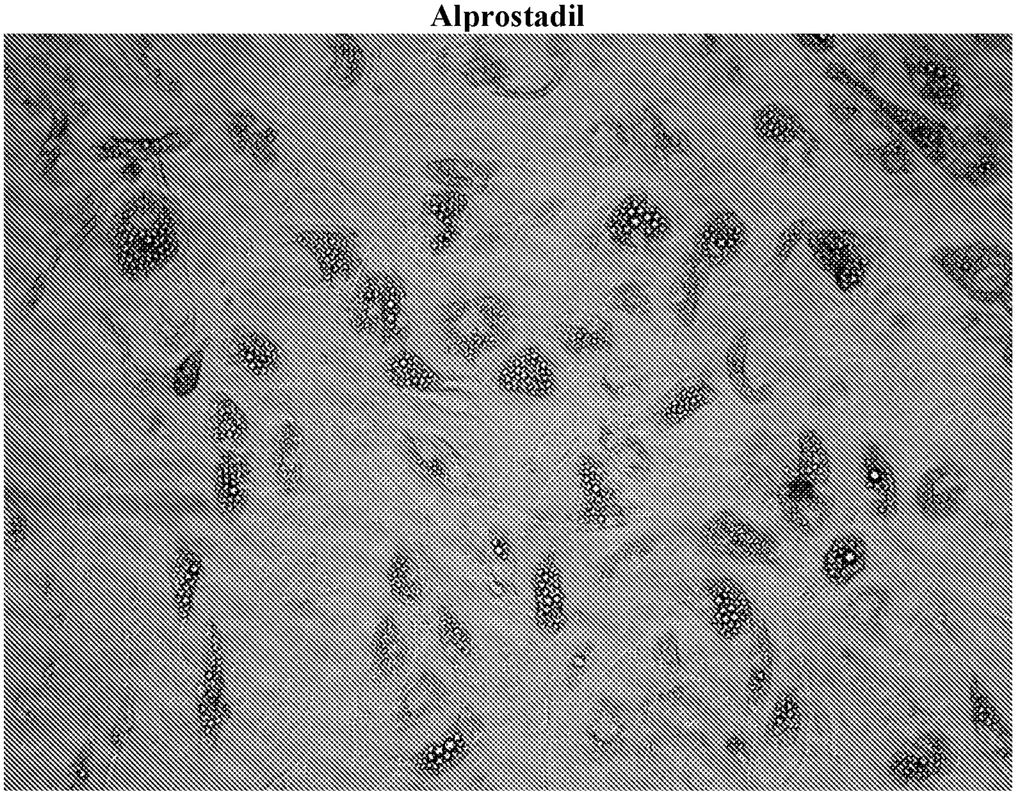
Figure 6G:
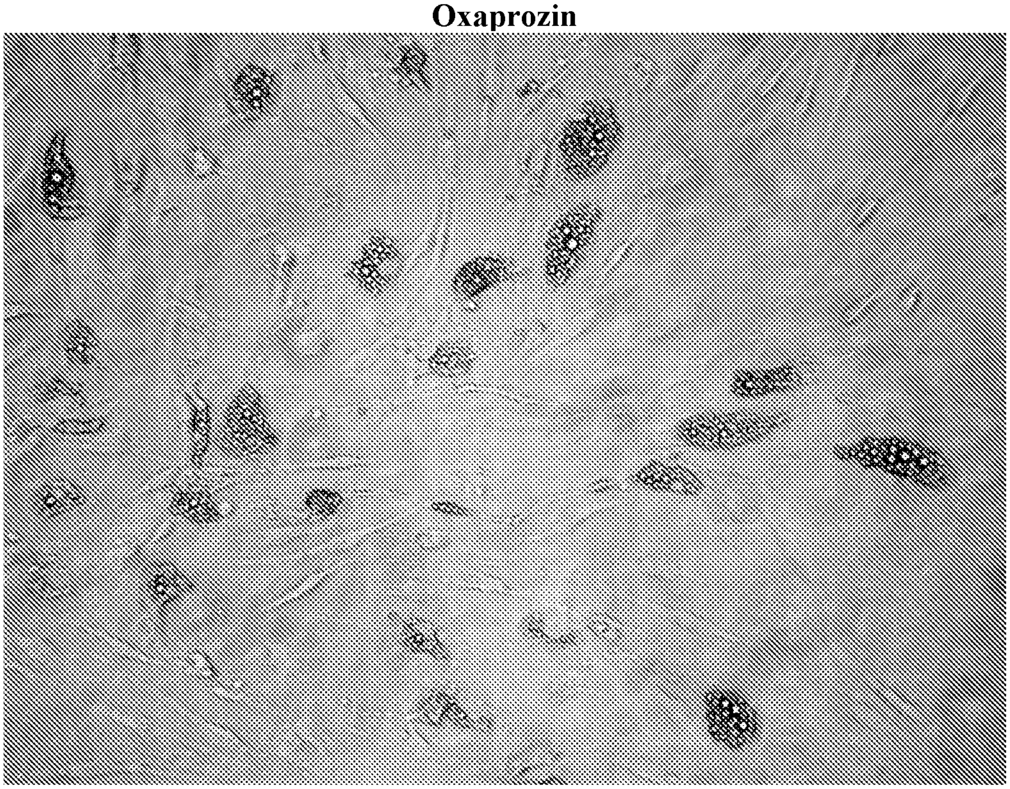
Figure 7:
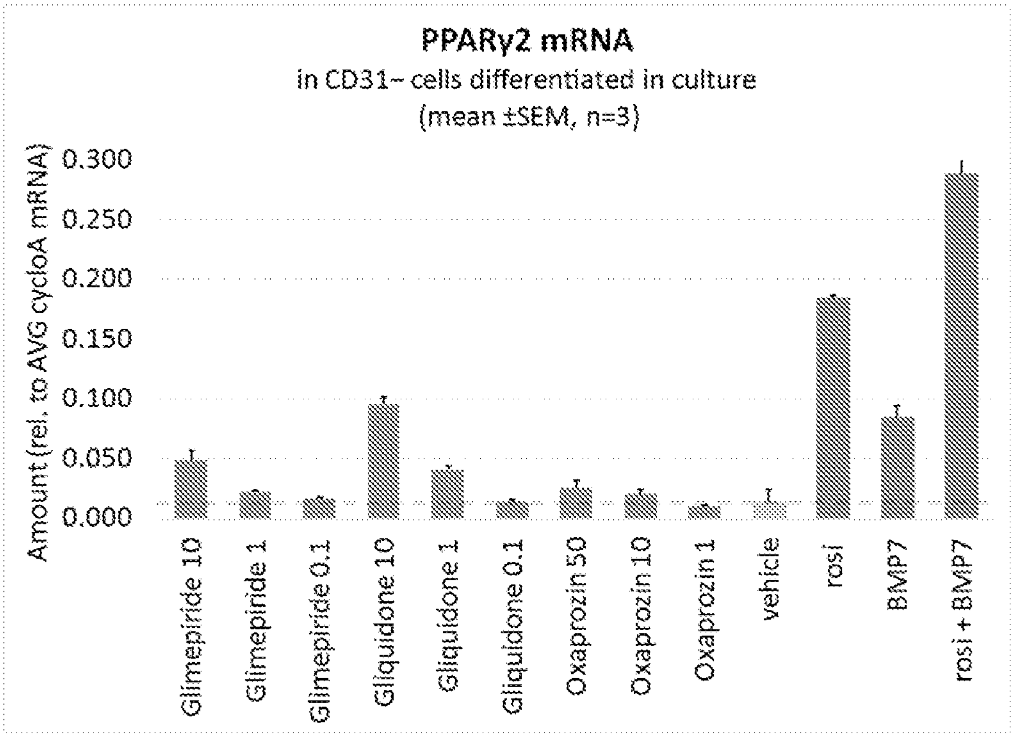
FIG. 7 shows the effects of glimepiride (0.1-10 μM), gliquidone (0.1-10 μM) or oxaprozin (1-50 μM) incubated with brown adipocyte progenitor cells at day −3 to d0 on the expression of PPARγ2 mRNA. Rosiglitazone (1 μM), BMP7 (6 nM), or the combination of both agents, are used as references.
Figure 8:
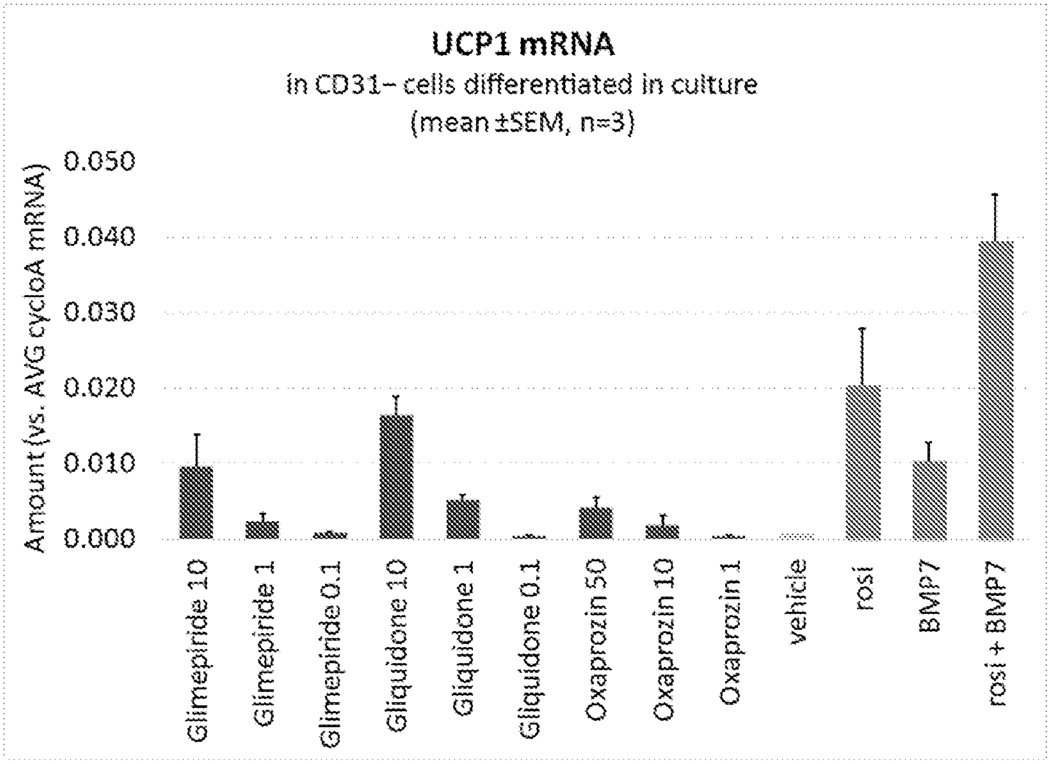
FIG. 8 shows the effects of glimepiride (0.1-10 μM), gliquidone (0.1-10 μM) or oxaprozin (1-50 μM) incubated with brown adipocyte progenitor cells at day −3 to d0 on the expression of UCP1 mRNA. Rosiglitazone (1 μM), BMP7 (6 nM), or the combination of both agents, are used as references.
Figure 9:
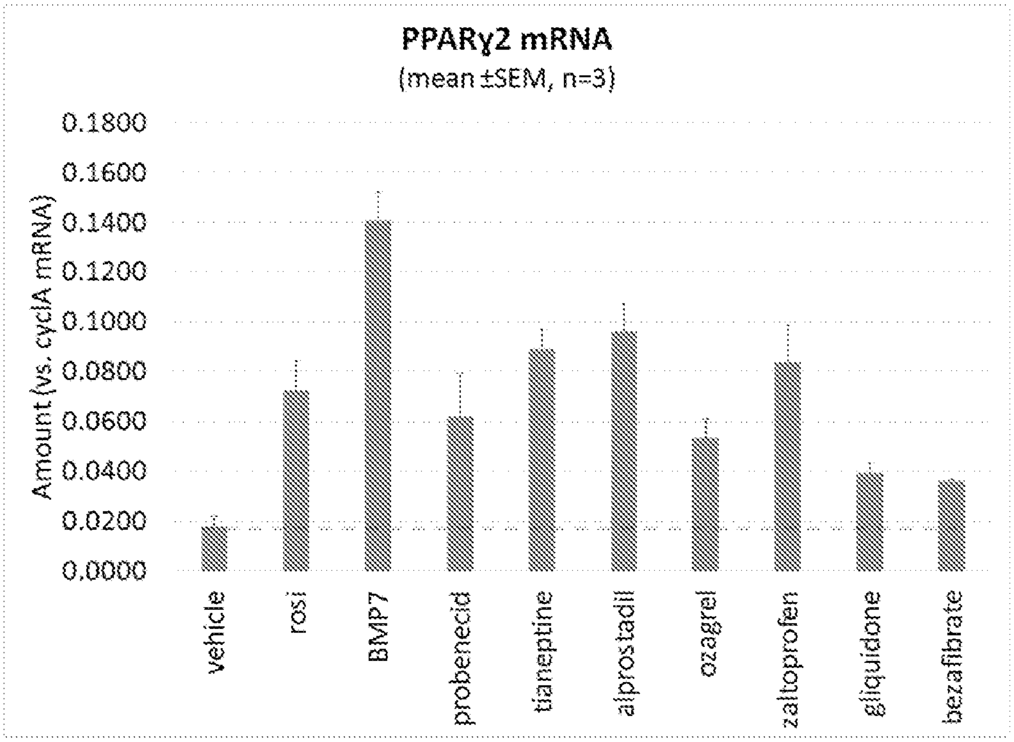
FIG. 9 shows the effects of probenecid (50 μM), tianeptine (50 μM), alprostadil (10 μM), ozagrel (50 μM), zaltoprofen (50 μM), gliquidone (10 μM) or bezafibrate (50 μM) (incubated with brown adipocyte progenitor cells at day −3 to d0) on the expression of PPARγ2 mRNA.
Figure 10:
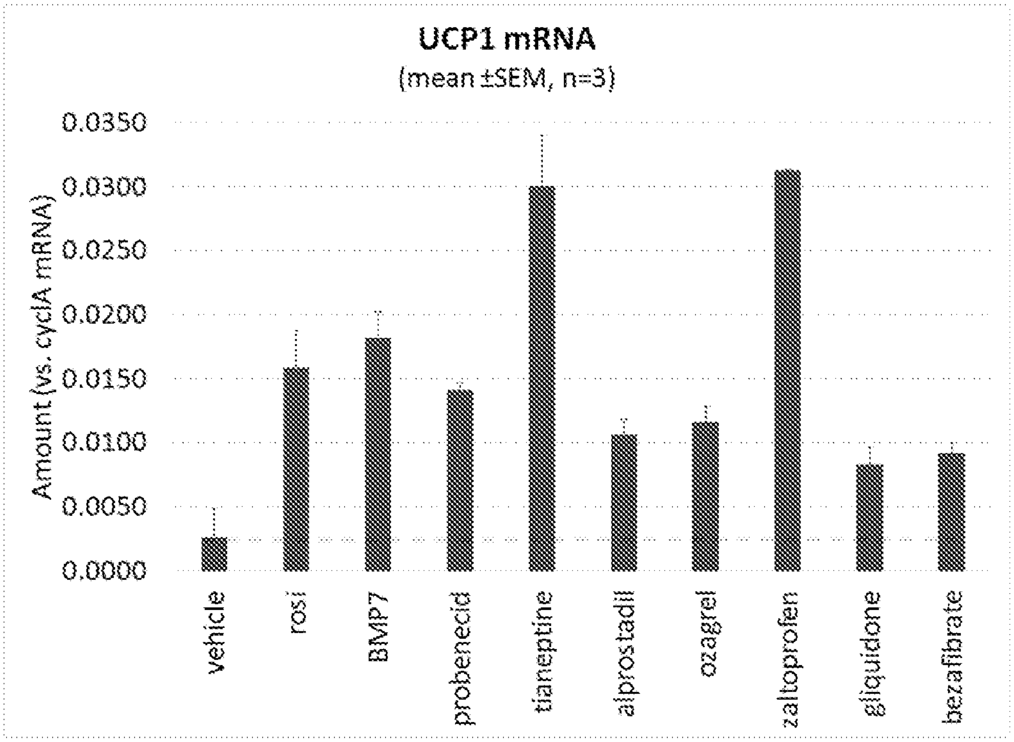
FIG. 10 shows the effects of probenecid (50 μM), tianeptine (50 μM), alprostadil (10 μM), ozagrel (50 μM), zaltoprofen (50 μM), gliquidone (10 μM) or bezafibrate (50 μM) (incubated with brown adipocyte progenitor cells at day −3 to d0) on the expression of UCP1 mRNA.
Figure 11:
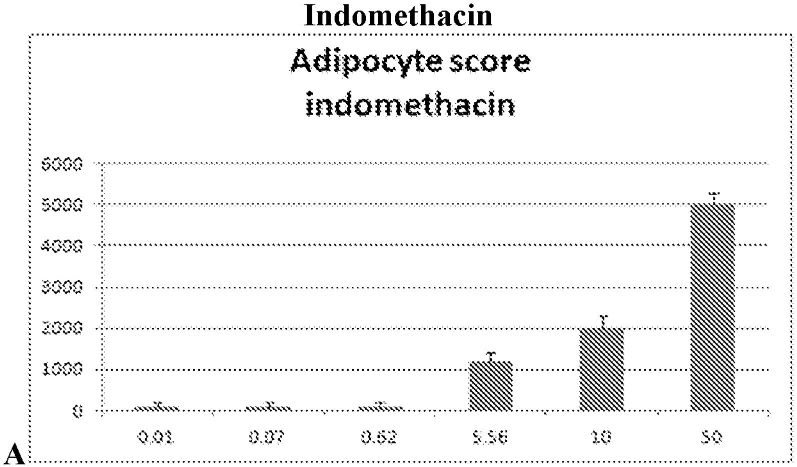
FIGS. 11-21 show dose-responses of compounds that promote brown adipocyte formation (recruitment of CD34+ cells into brown adipocytes) in culture.
Figure 11:
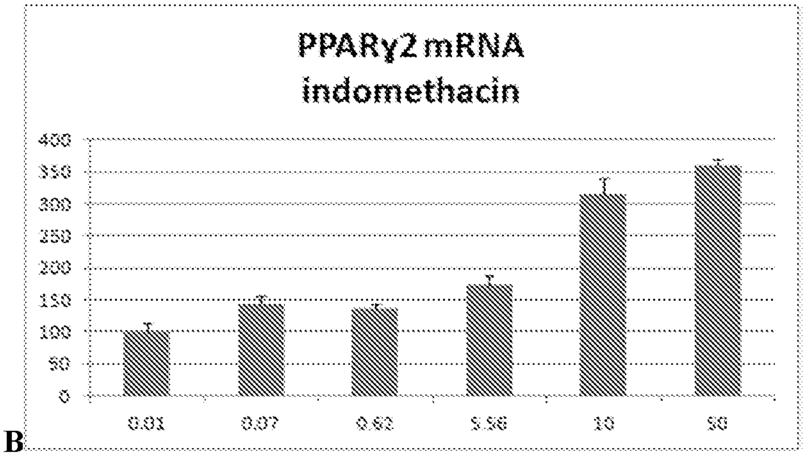
Figure 11:
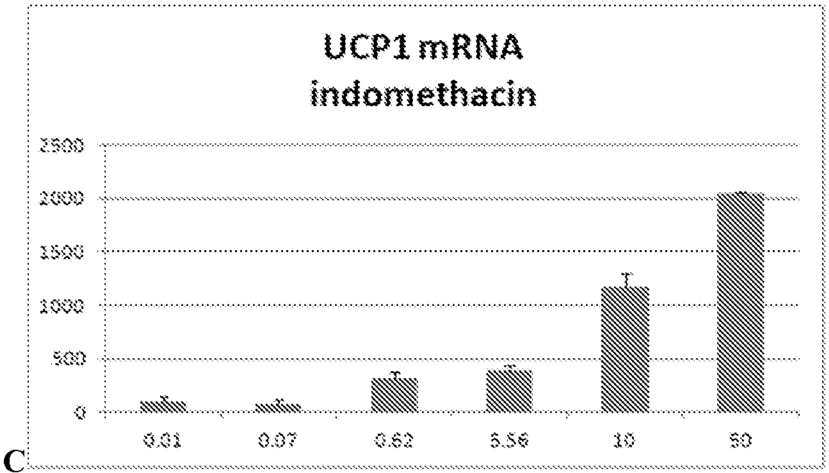
Figure 12:
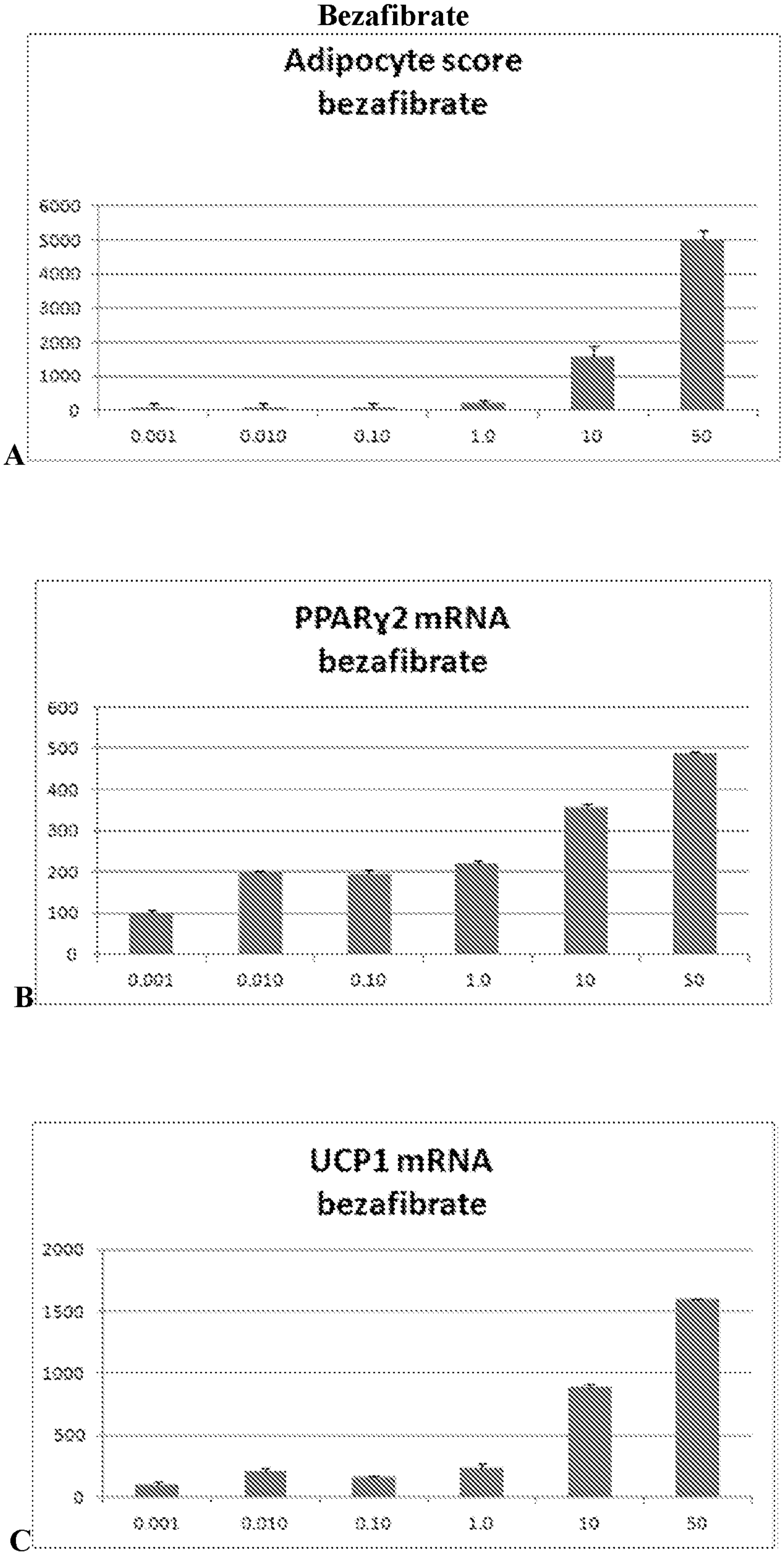
Figure 13:
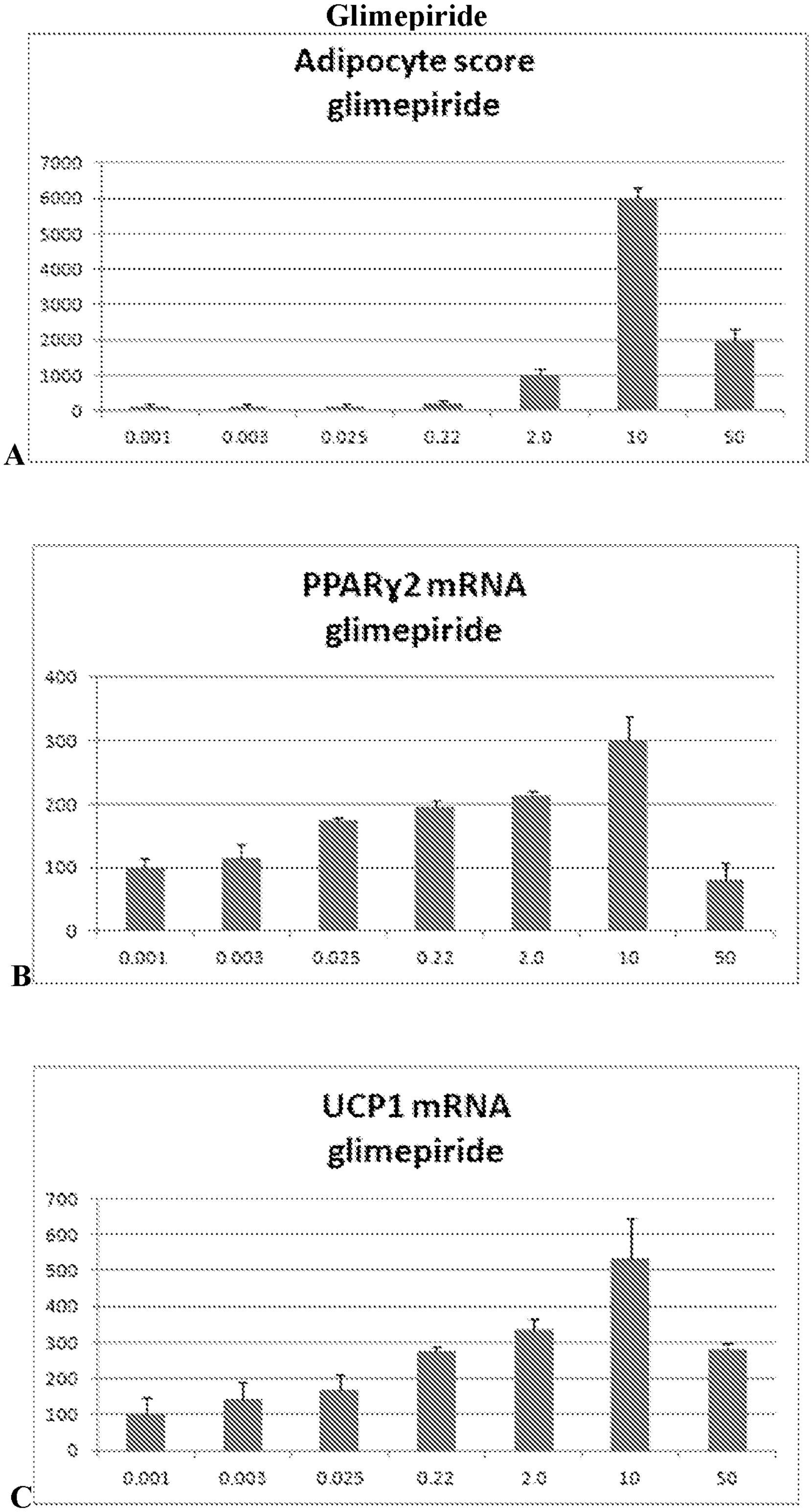
Figure 14:
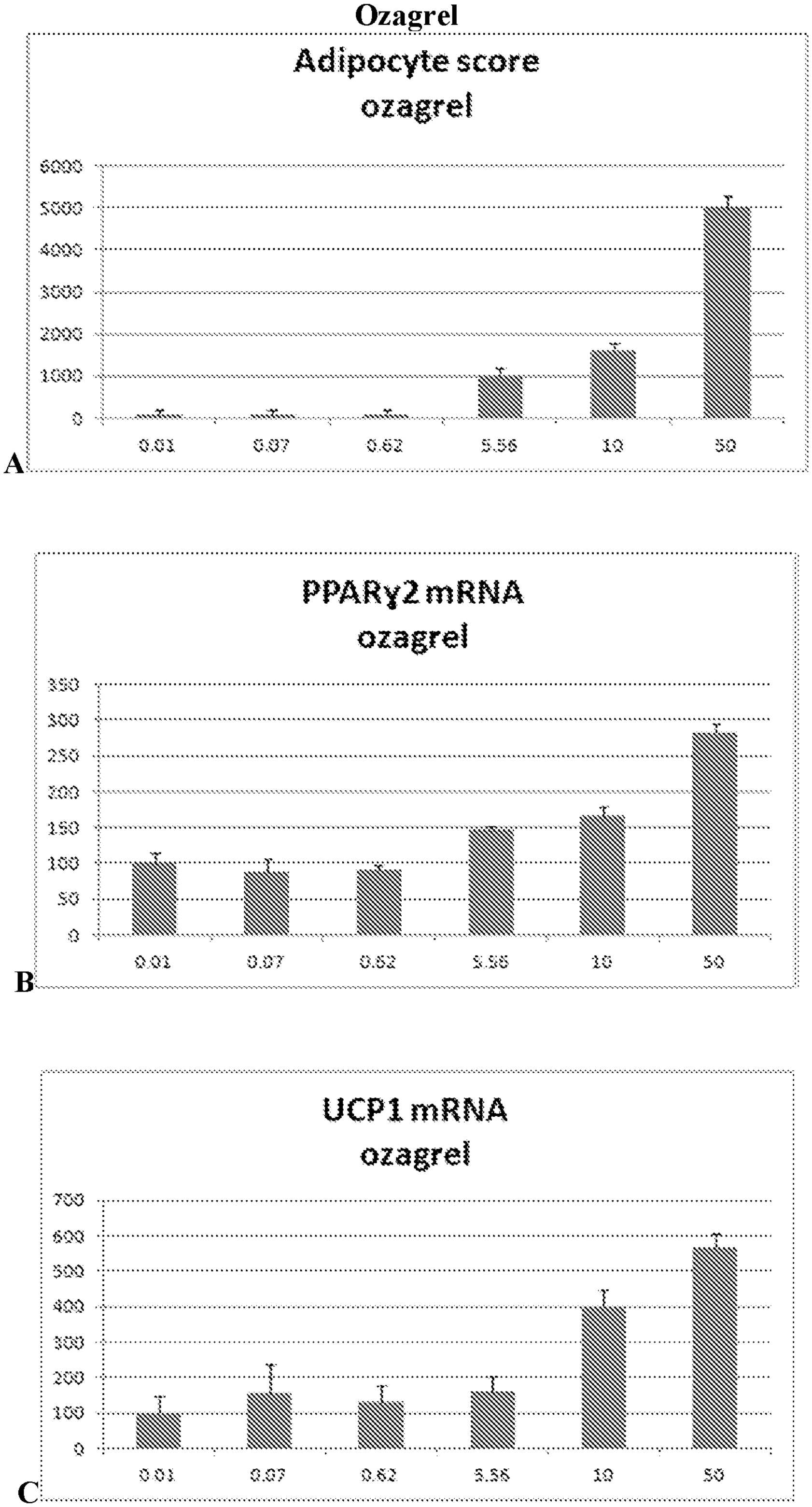
Figure 15:
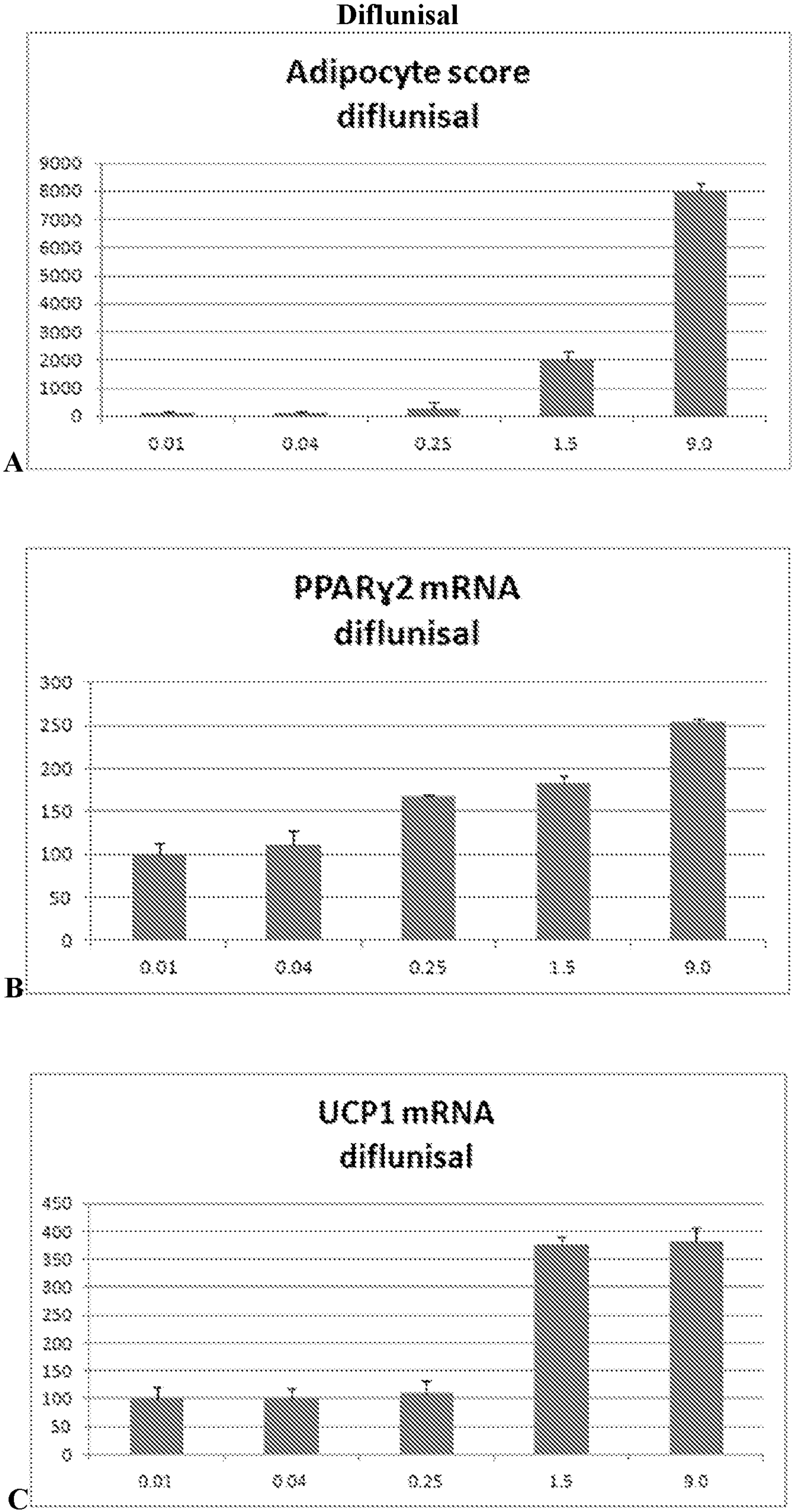
Figure 16:
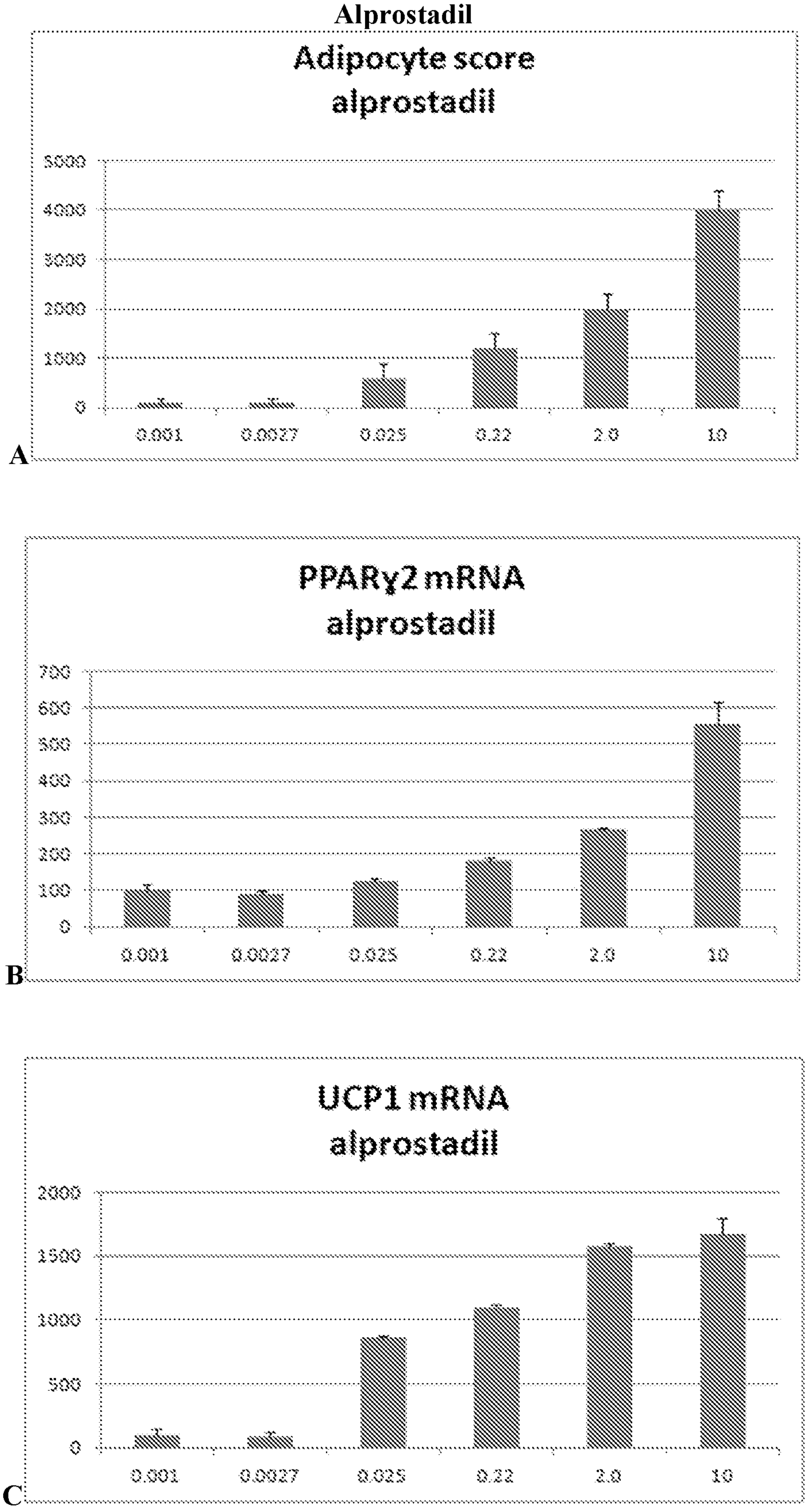
Figure 17:
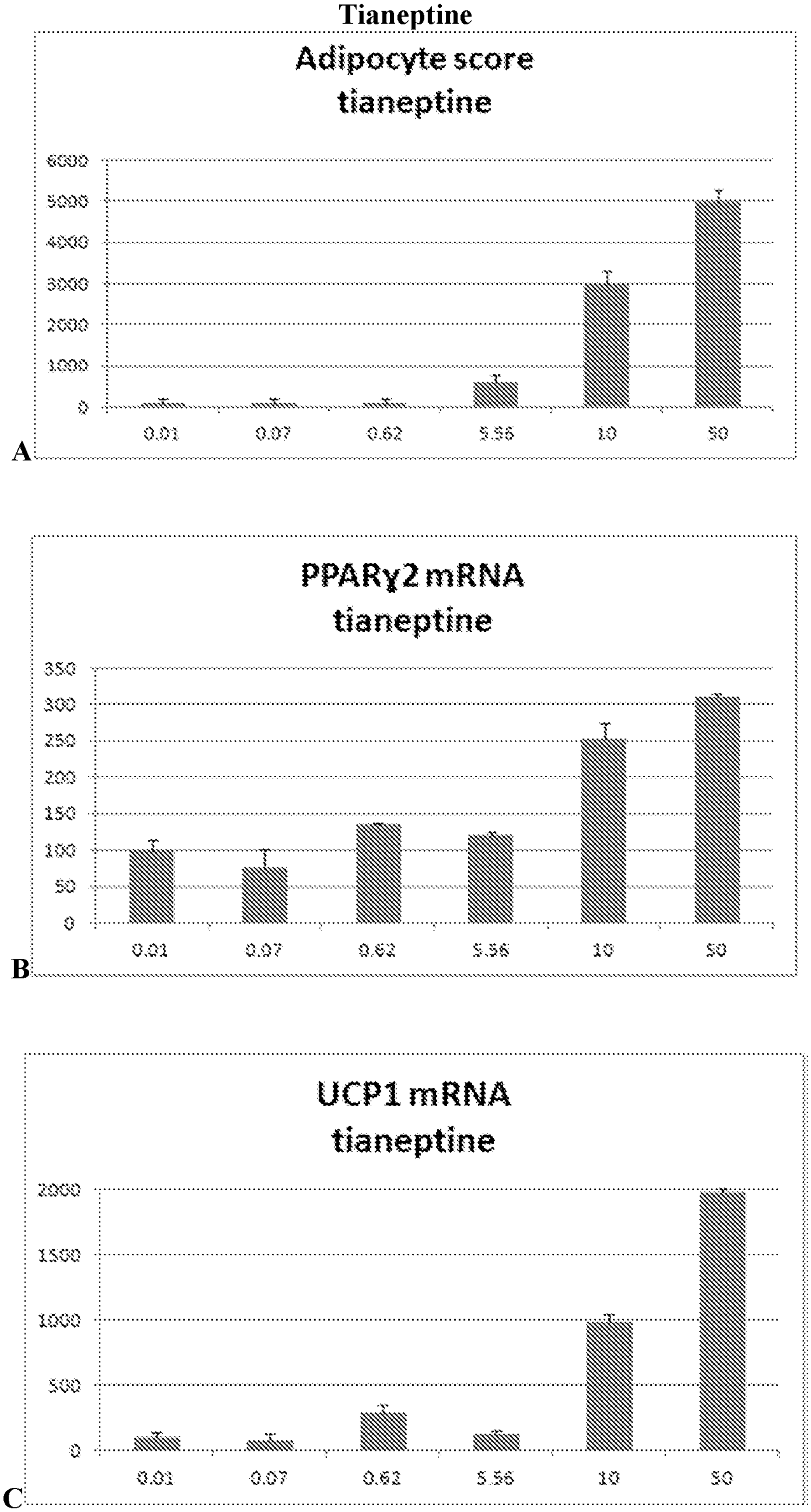
Figure 18:
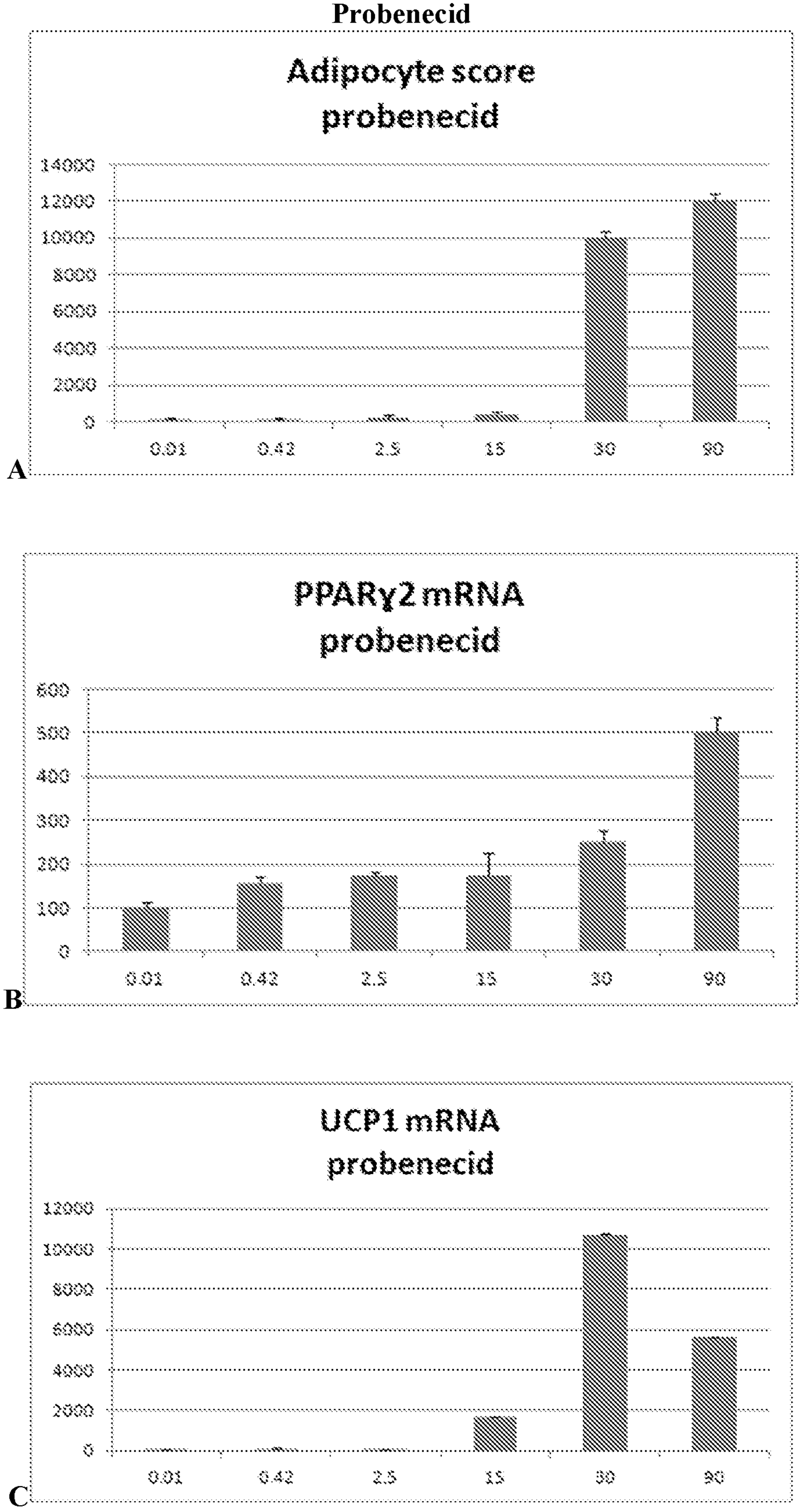
Figure 19:
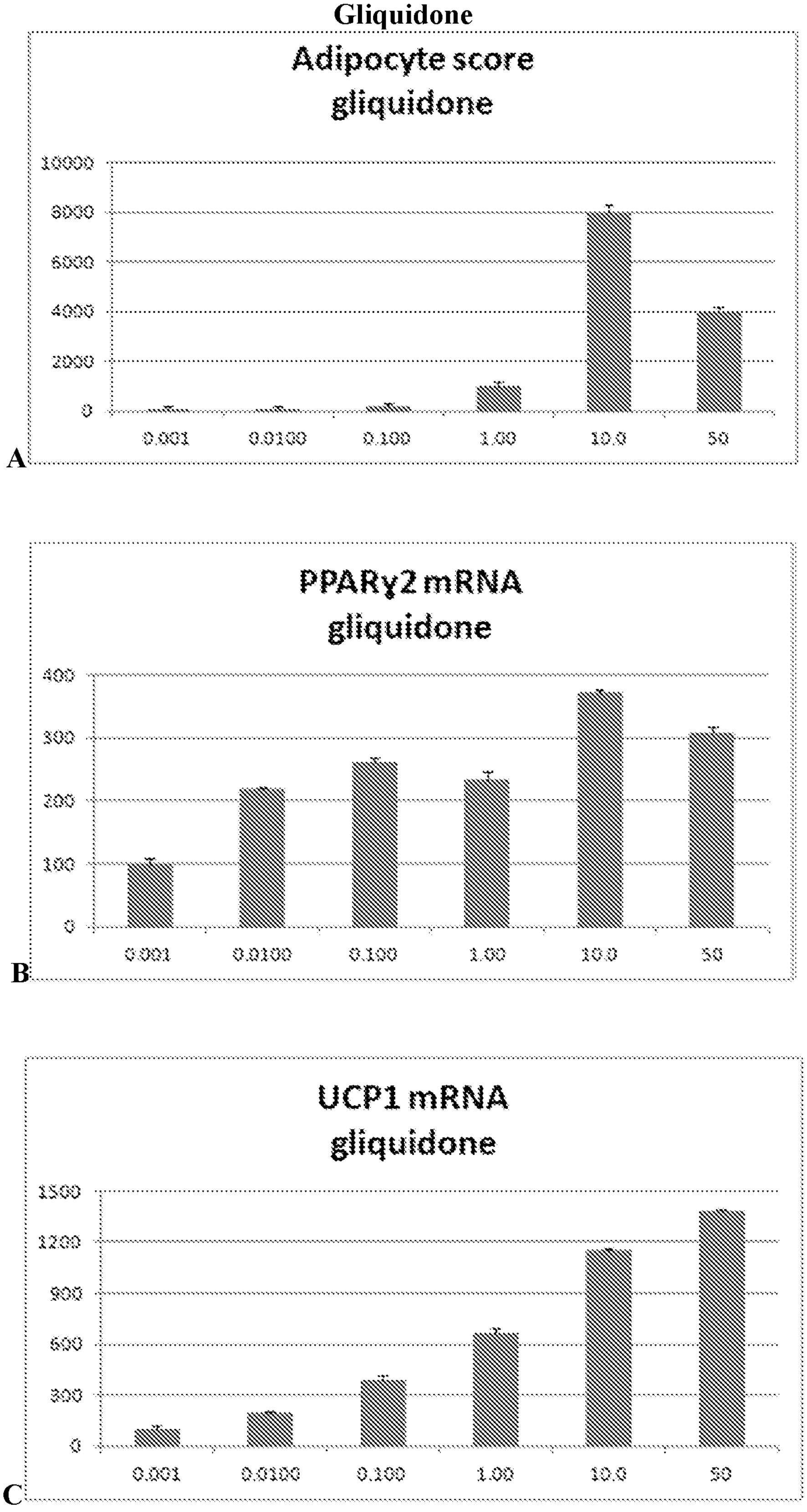
Figure 20:
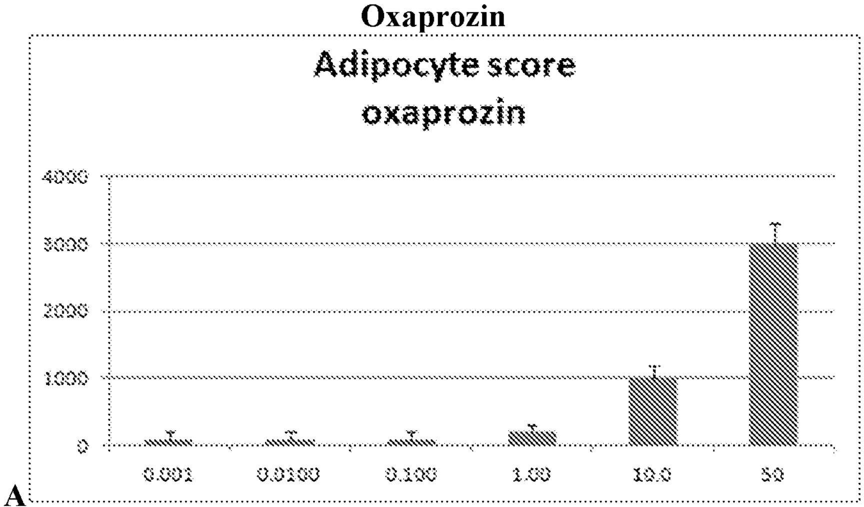
Figure 20:
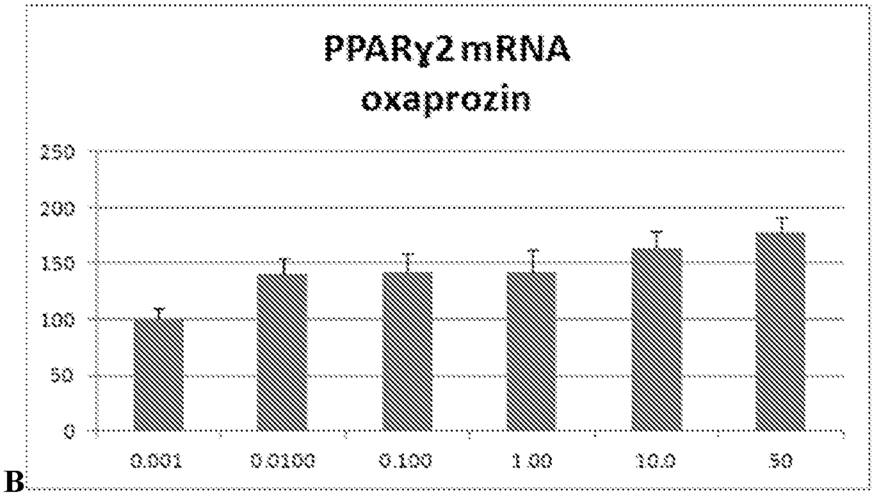
Figure 20:
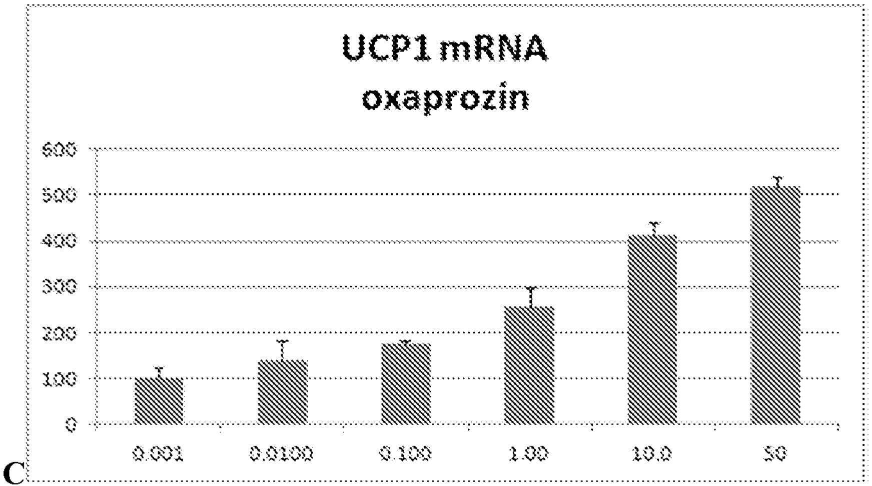
Figure 21:
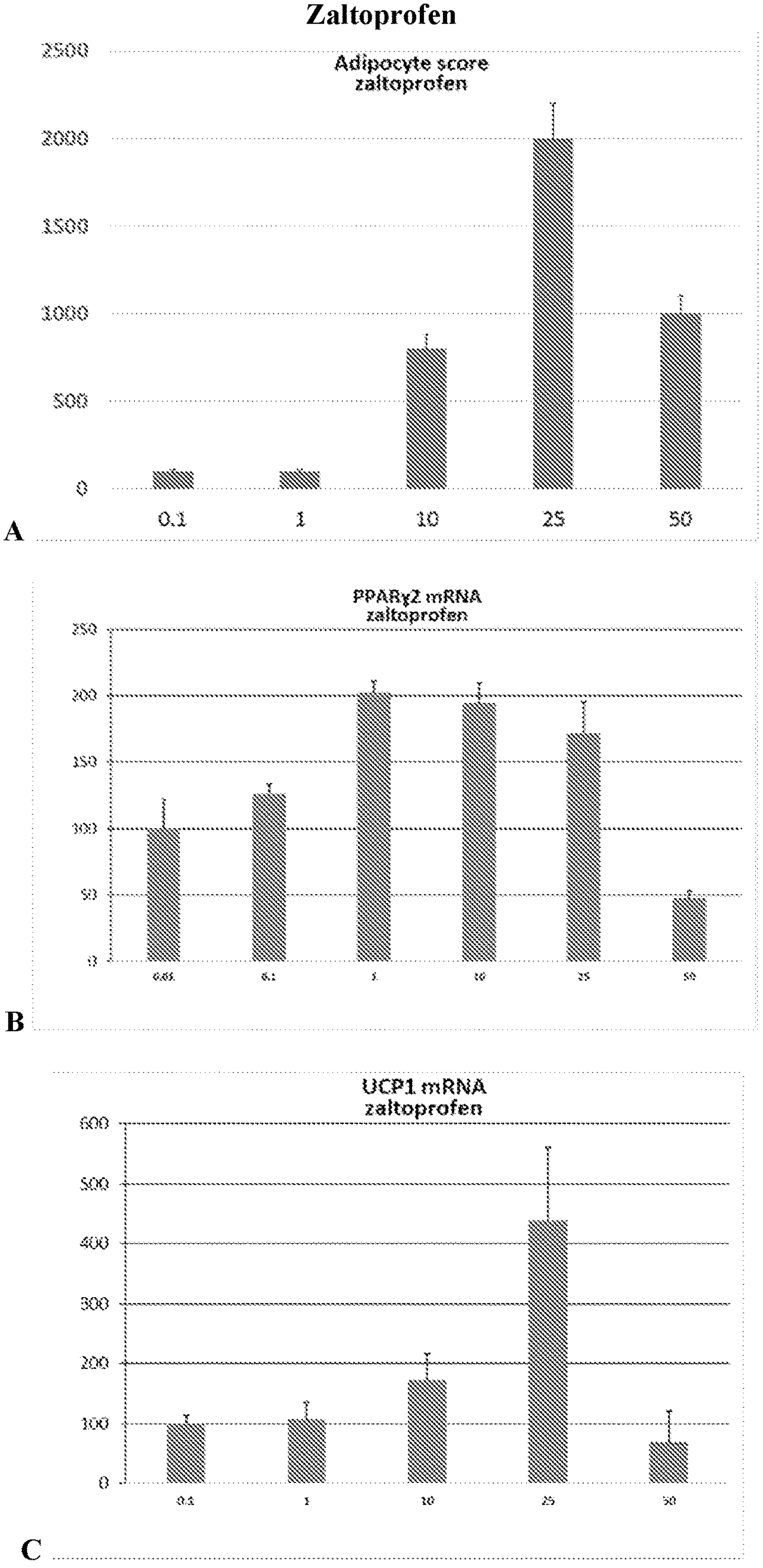

FIG. 11. Indomethacin.
FIG. 12. Bezafibrate.
FIG. 13. Glimepiride.
FIG. 14. Ozagrel.
FIG. 15. Diflunisal.
FIG. 16. Alprostadil.
FIG. 17. Tianeptine.
FIG. 18. Probenecid.
FIG. 19. Gliquidone.
FIG. 20. Oxaprozin.
FIG. 21. Zaltoprofen.

Figure 22:
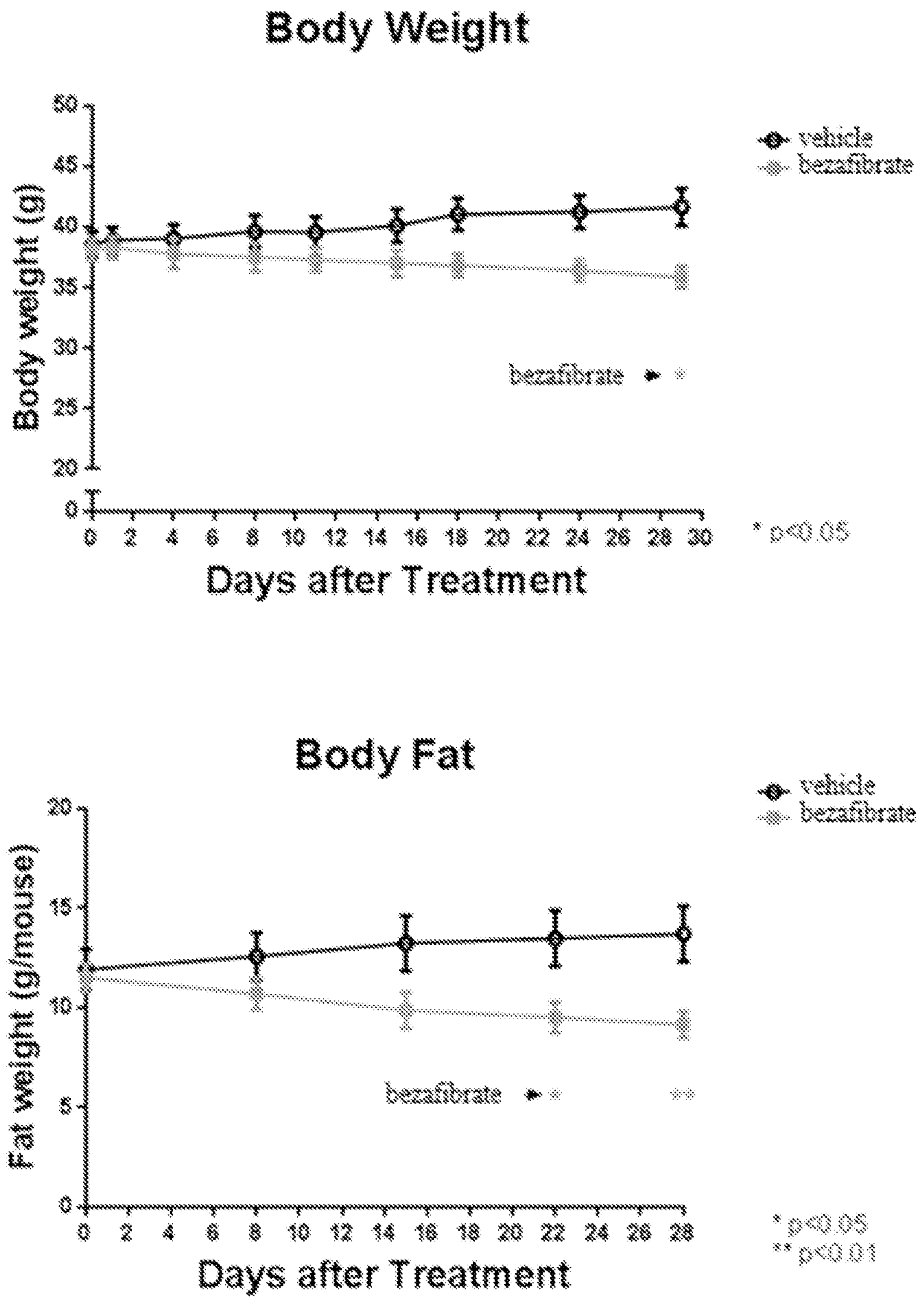

FIG. 22 shows the effects of bezafibrate (115 mg/kg BW by oral gavage once a day) on body weight and body fat in DIO mice.

Figure 23:
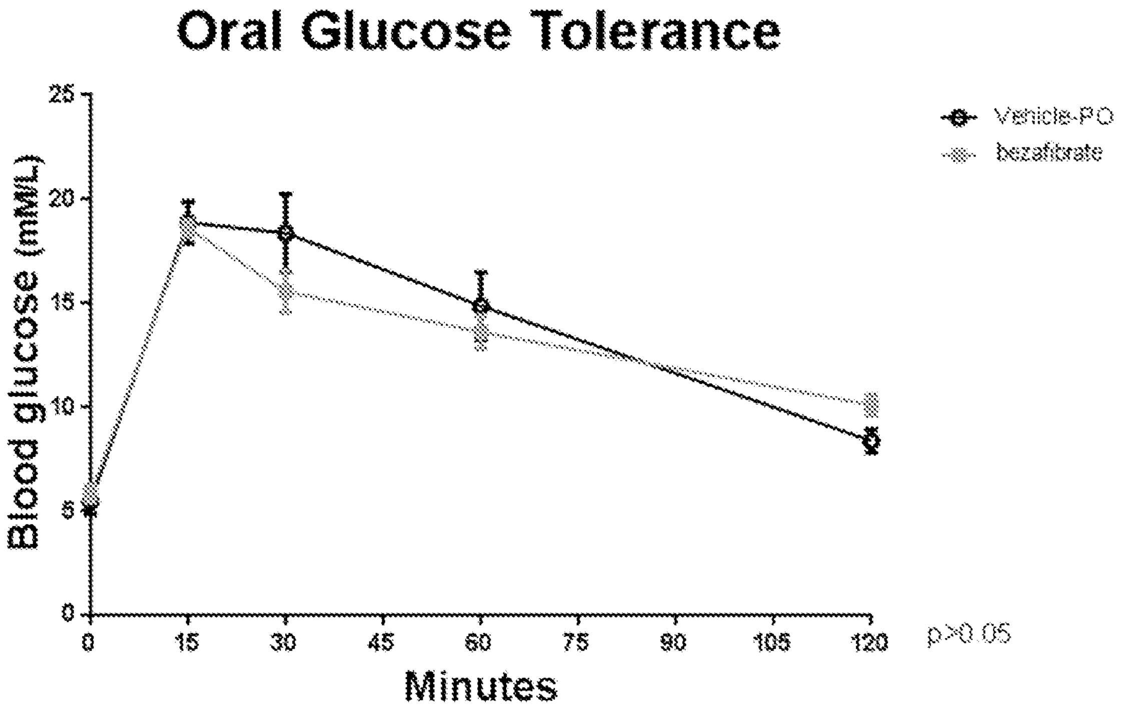

FIG. 23 shows the effects of bezafibrate (115 mg/kg BW by oral gavage once a day for 3 weeks) on glucose tolerance in DIO mice.

Figure 24:
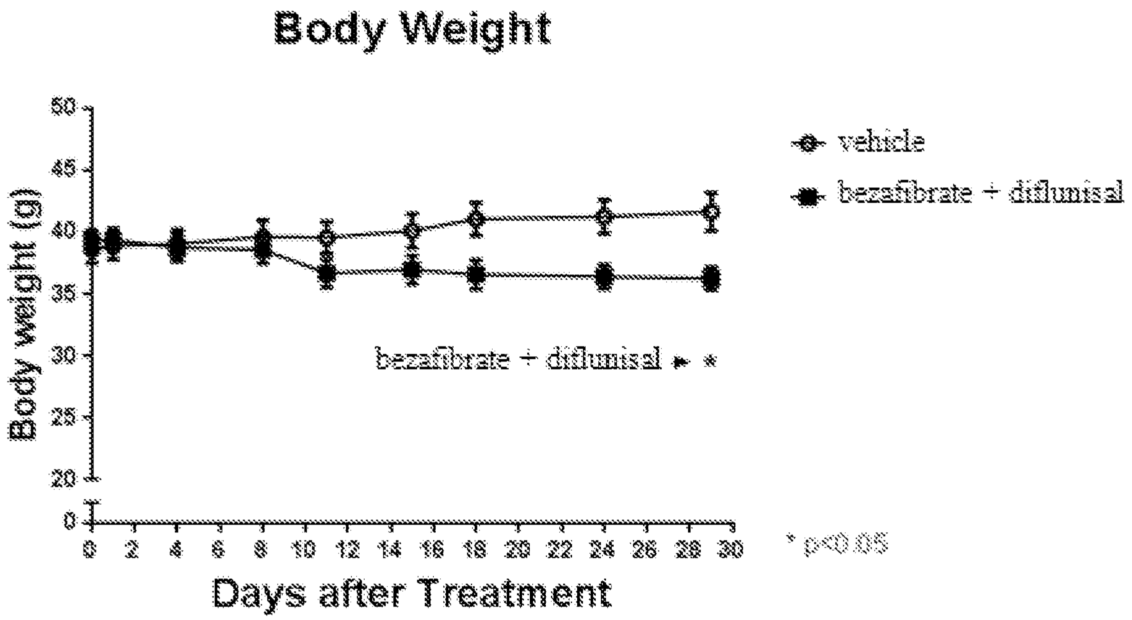
Figure 24:
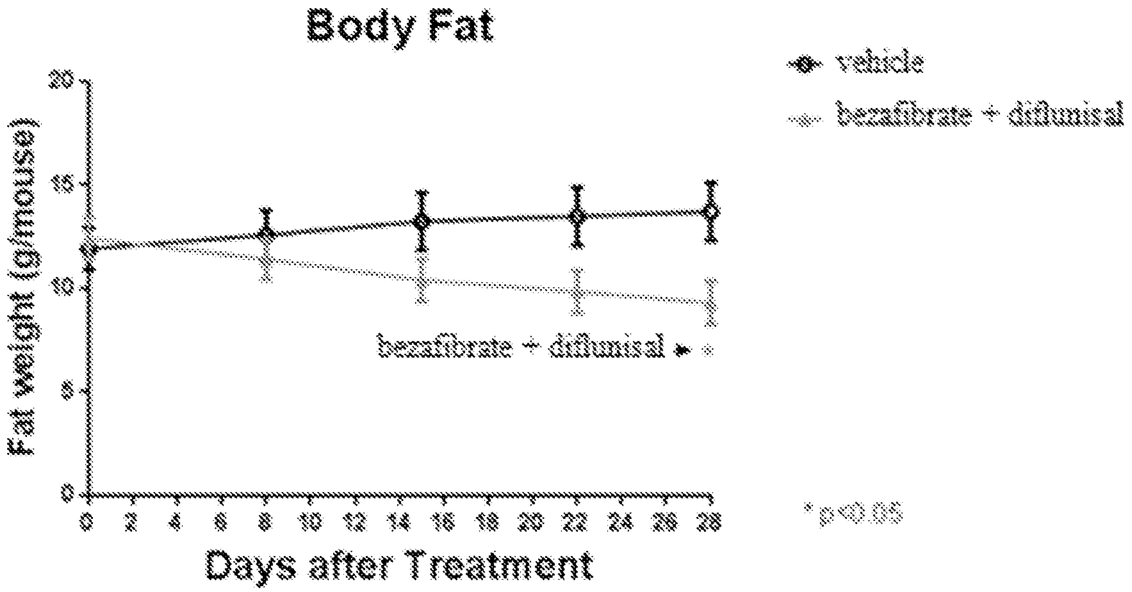

FIG. 24 shows the effects of bezafibrate (115 mg/kg BW by oral gavage once a day) in combination with diflunisal (100 mg/kg BW) on body weight and body fat in DIO mice.

Figure 25:
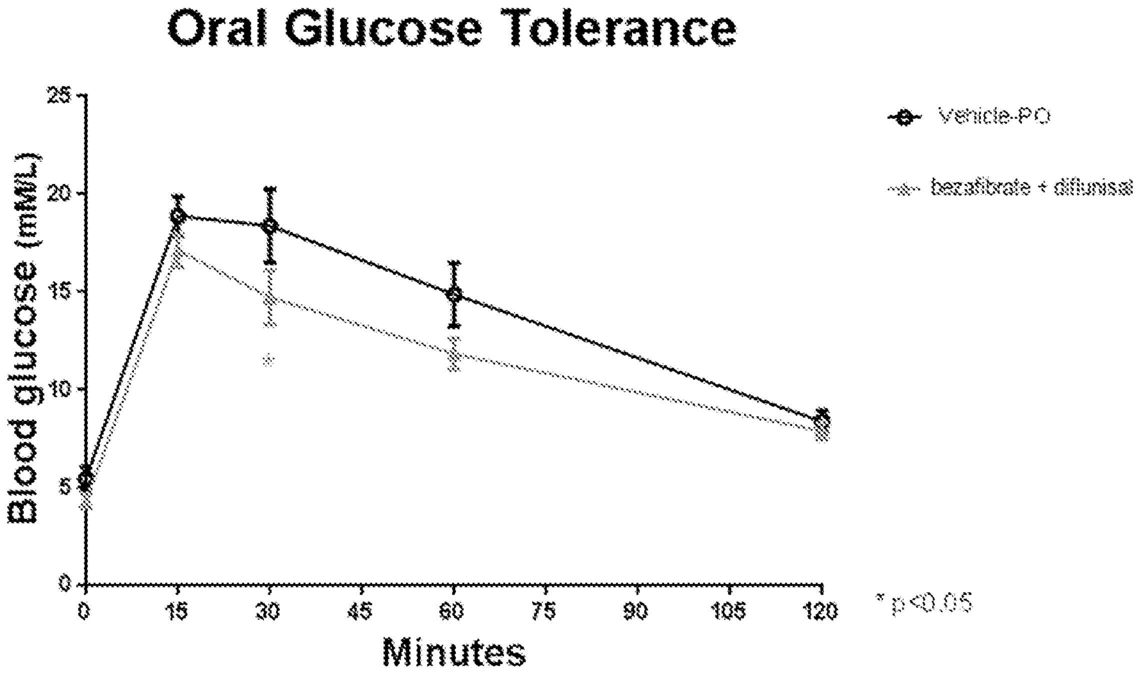

FIG. 25 shows the effects of bezafibrate (115 mg/kg BW by oral gavage once a day for 3 weeks) in combination with diflunisal (100 mg/kg BW) on glucose tolerance in DIO mice.

Figure 26:
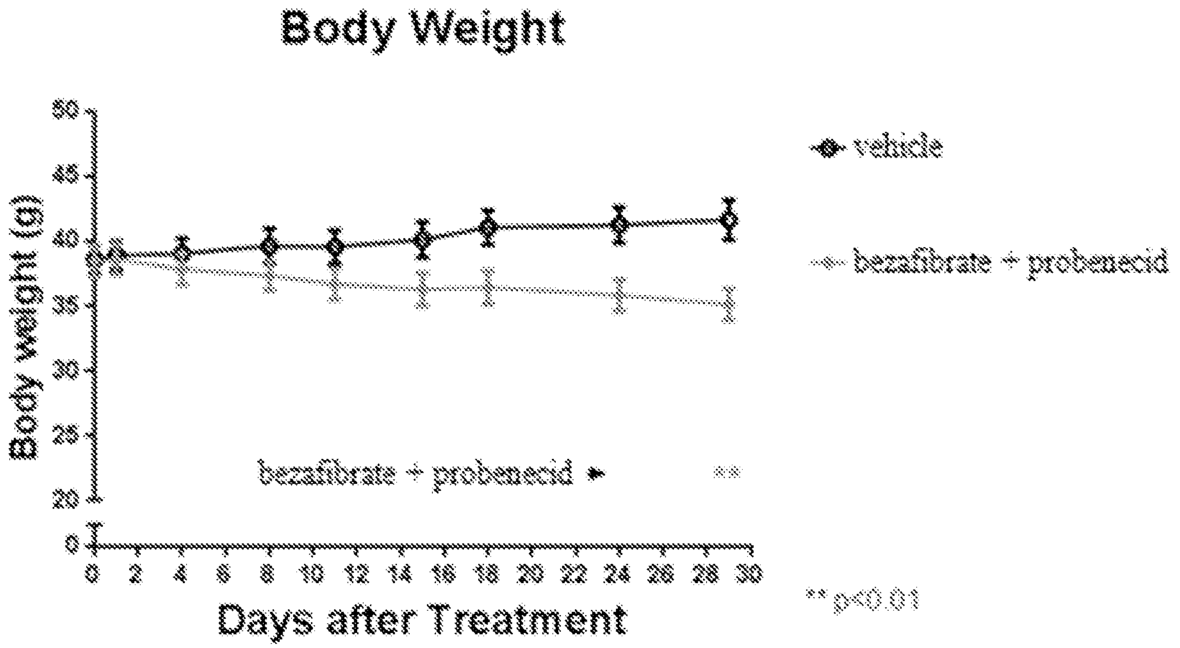
Figure 26:
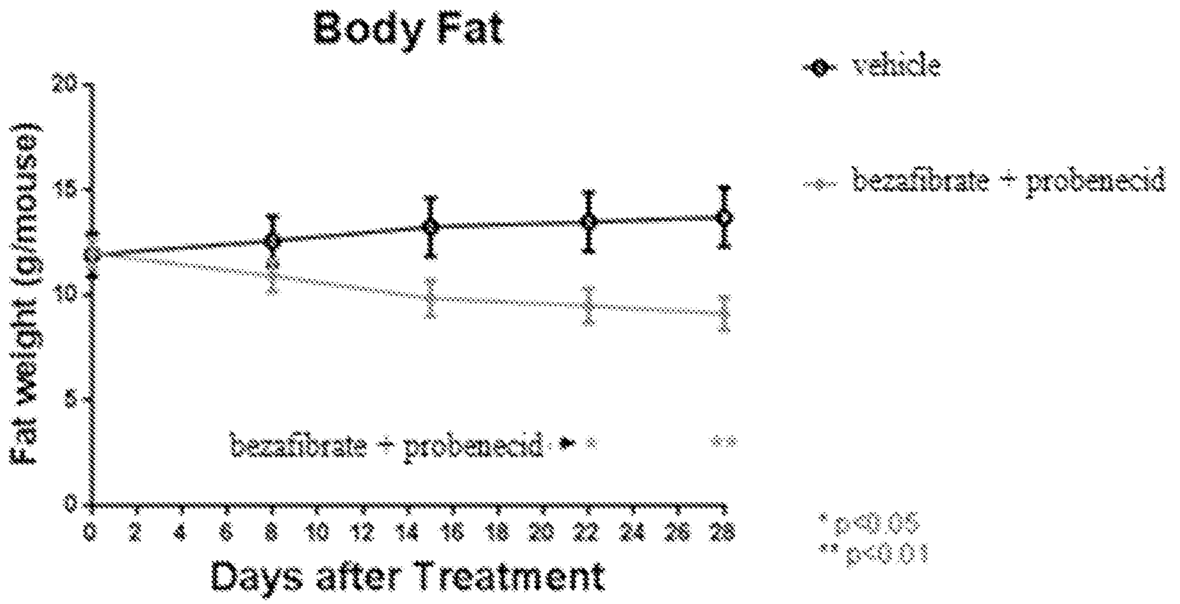

FIG. 26 shows the effects of bezafibrate (115 mg/kg BW by oral gavage once a day) in combination with probenecid (100 mg/kg BW) on body weight and body fat in DIO mice.

Figure 27:
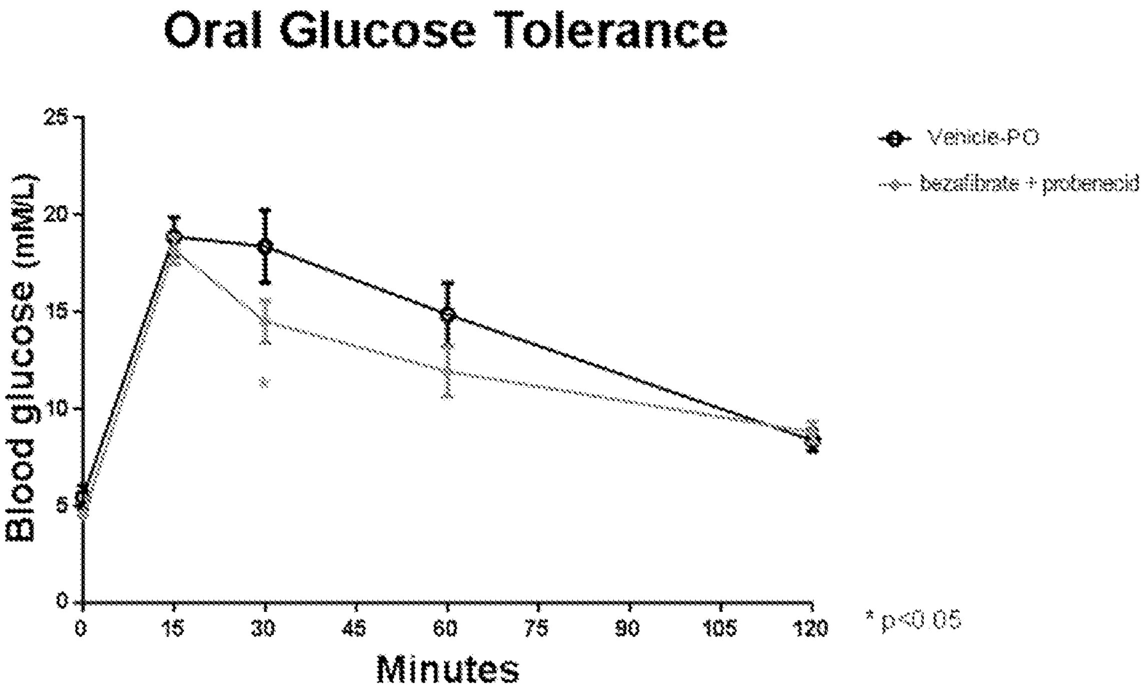

FIG. 27 shows the effects of bezafibrate (115 mg/kg BW by oral gavage once a day for 3 weeks) in combination with probenecid (100 mg/kg BW) on glucose tolerance in DIO mice.

Figure 28:
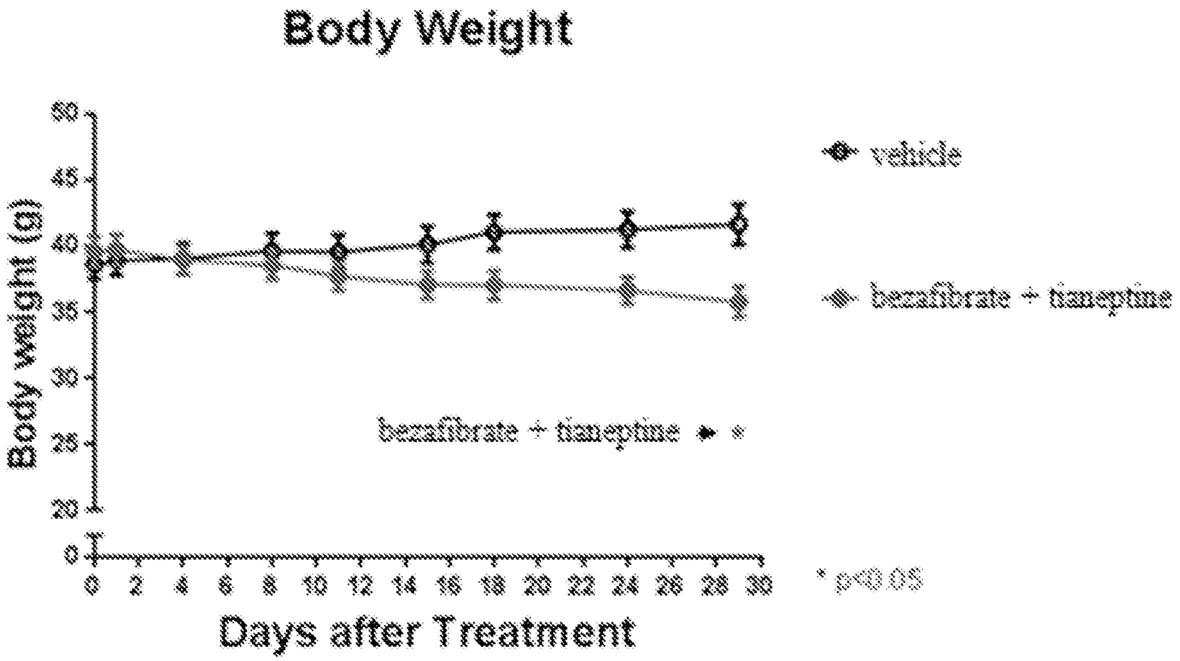
Figure 28:
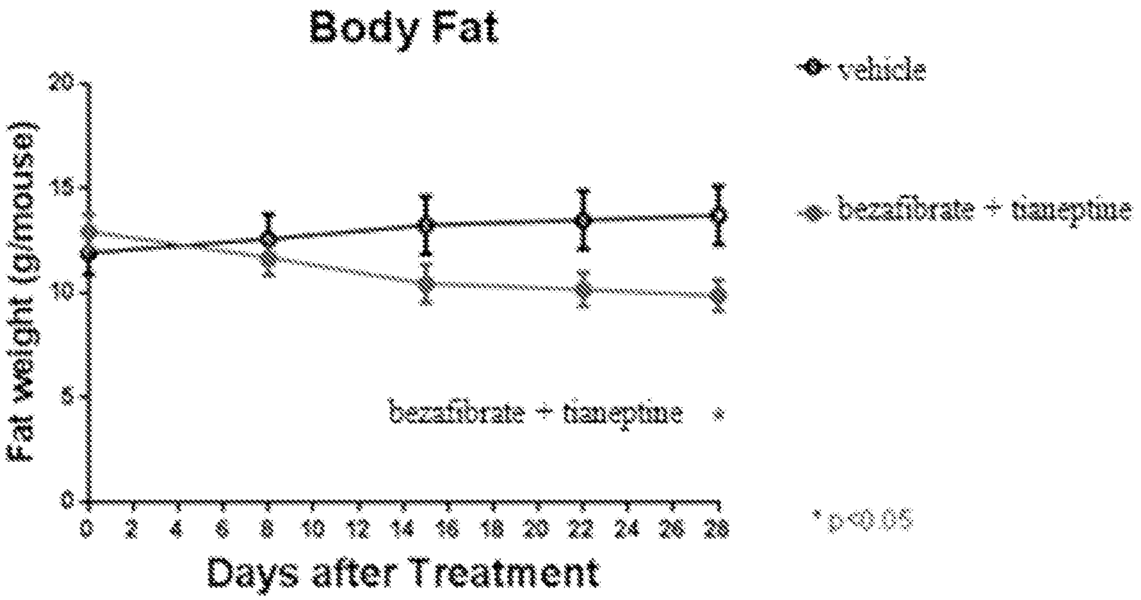

FIG. 28 shows the effects of bezafibrate (115 mg/kg BW by oral gavage once a day) in combination with tianeptine (10 mg/kg BW) on body weight and body fat in DIO mice.

Figure 29:
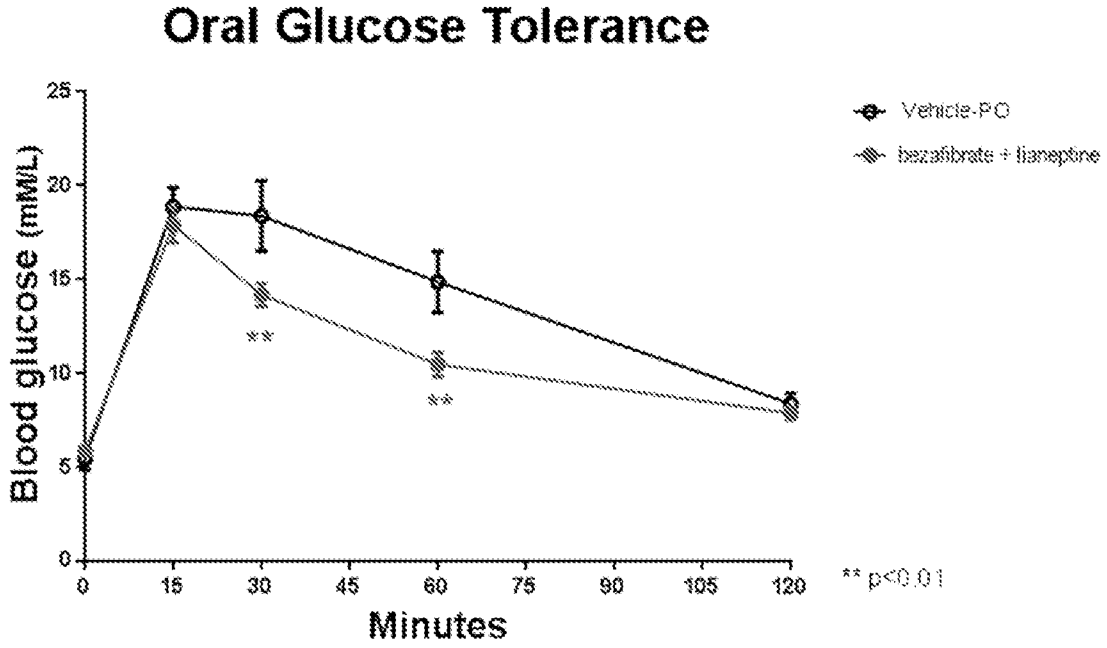

FIG. 29 shows the effects of bezafibrate (115 mg/kg BW by oral gavage once a day for 3 weeks) in combination with tianeptine (10 mg/kg BW) on glucose tolerance in DIO mice.

Figure 30:
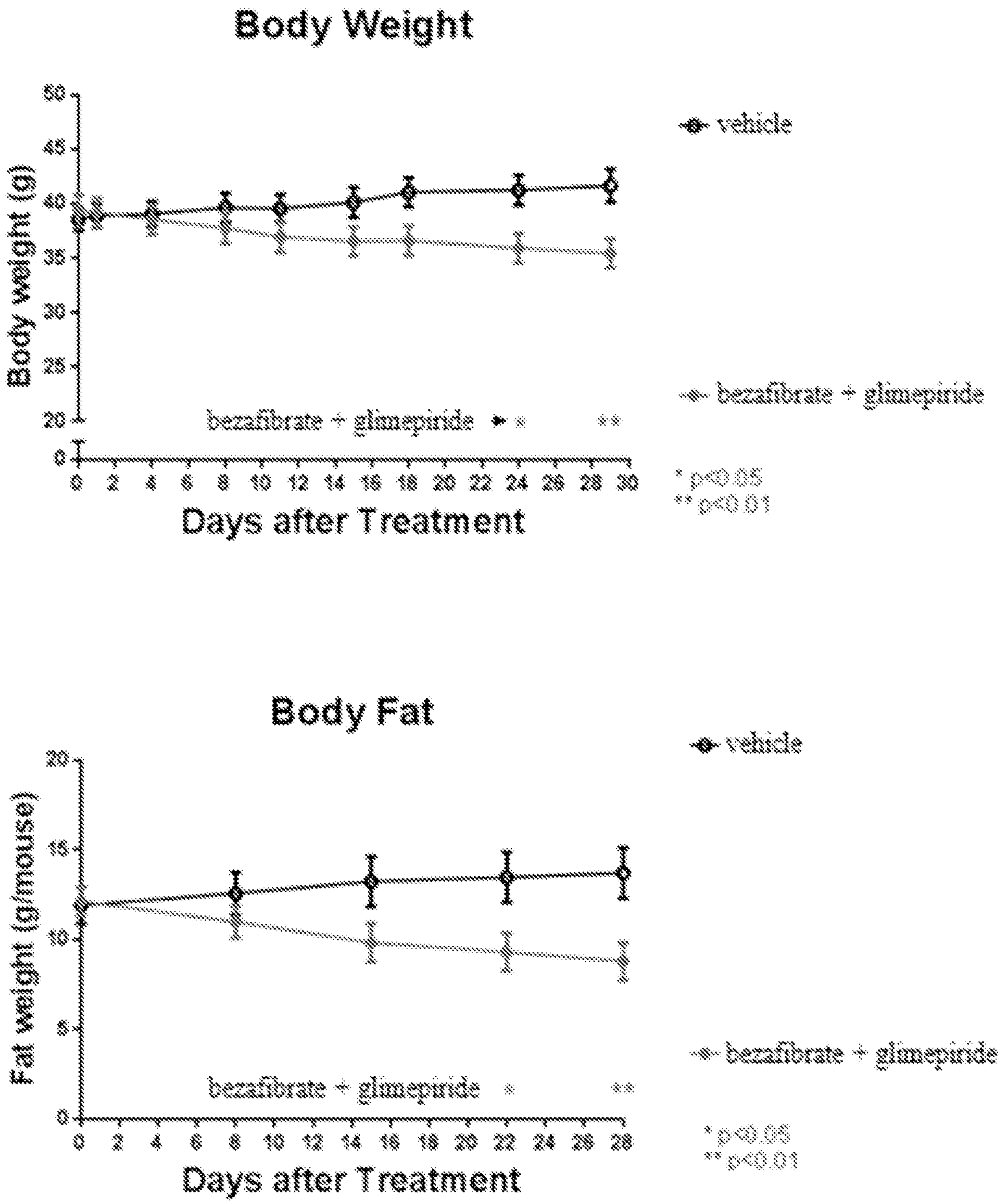

FIG. 30 shows the effects of bezafibrate (115 mg/kg BW by oral gavage once a day) in combination with glimepiride (0.6 mg/kg BW) on body weight and body fat in DIO mice.

Figure 31:
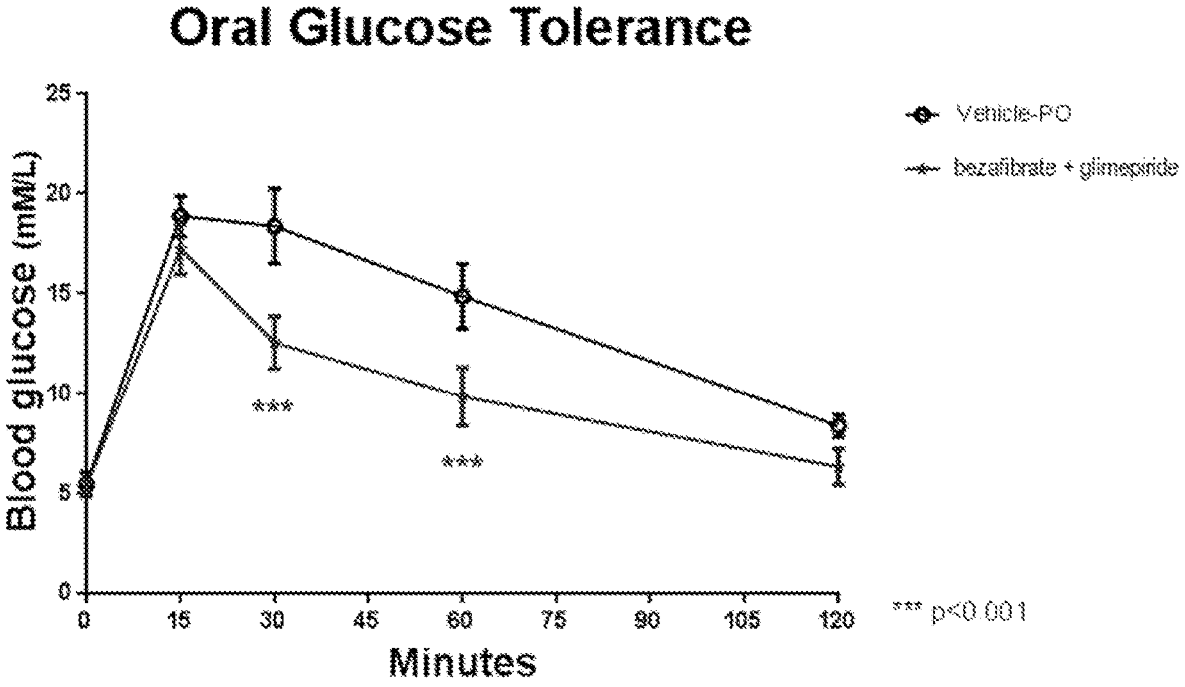

FIG. 31 shows the effects of bezafibrate (115 mg/kg BW by oral gavage once a day for 3 weeks) in combination with glimepiride (0.6 mg/kg BW) on glucose tolerance in DIO mice.

Figure 32:
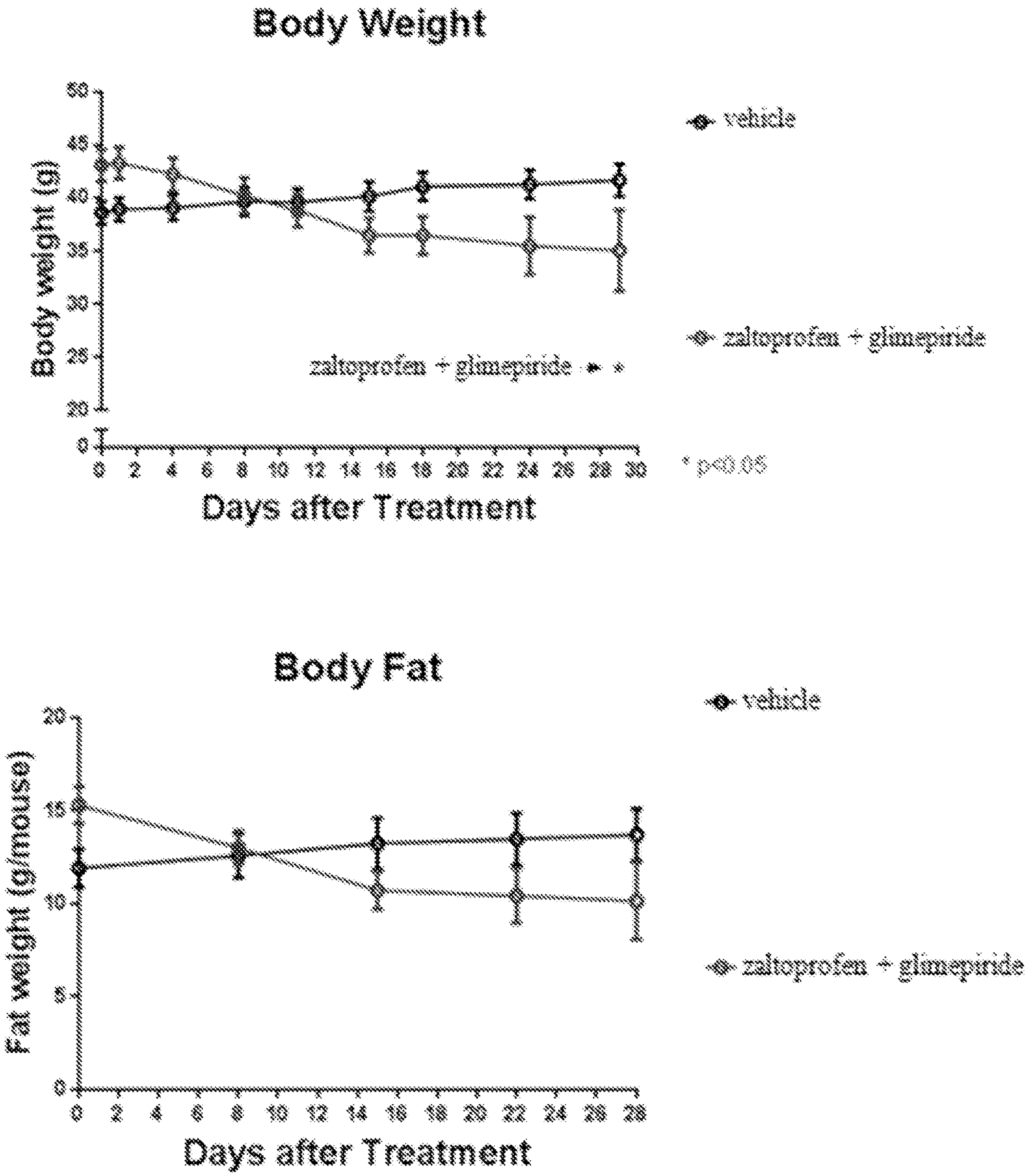

FIG. 32 shows the effects of zaltoprofen (50 mg/kg BW by oral gavage once a day) in combination with glimepiride (0.6 mg/kg BW) on body weight and body fat in DIO mice.

Figure 33:
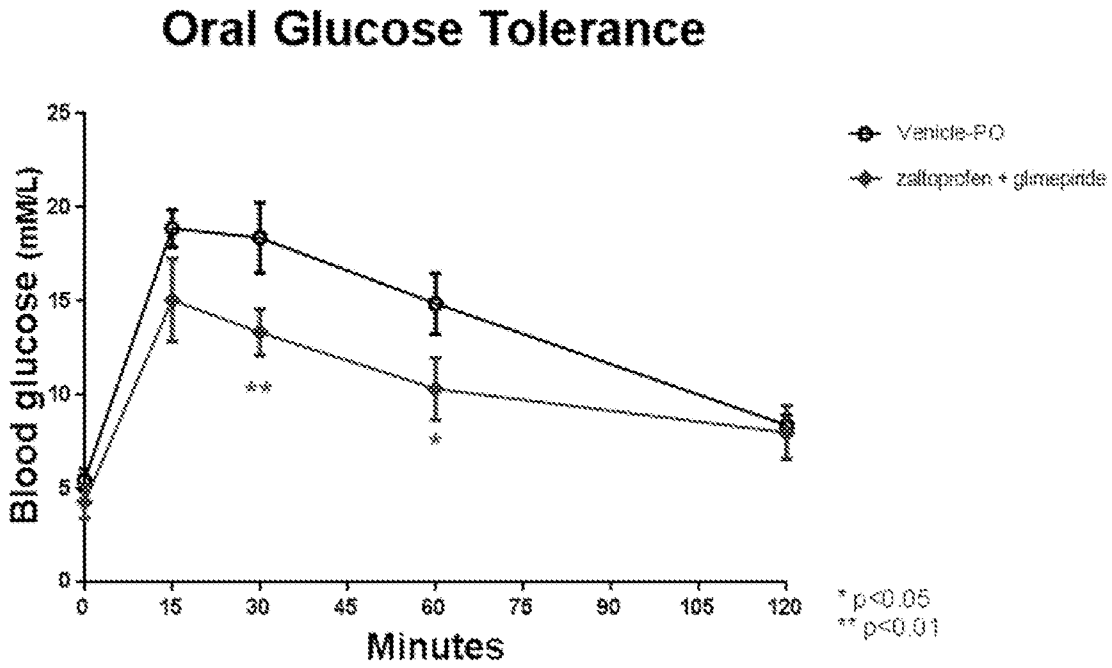

FIG. 33 shows the effects of zaltoprofen (50 mg/kg BW by oral gavage once a day for 3 weeks) in combination with glimepiride (0.6 mg/kg BW) on glucose tolerance in DIO mice.

Figure 34:
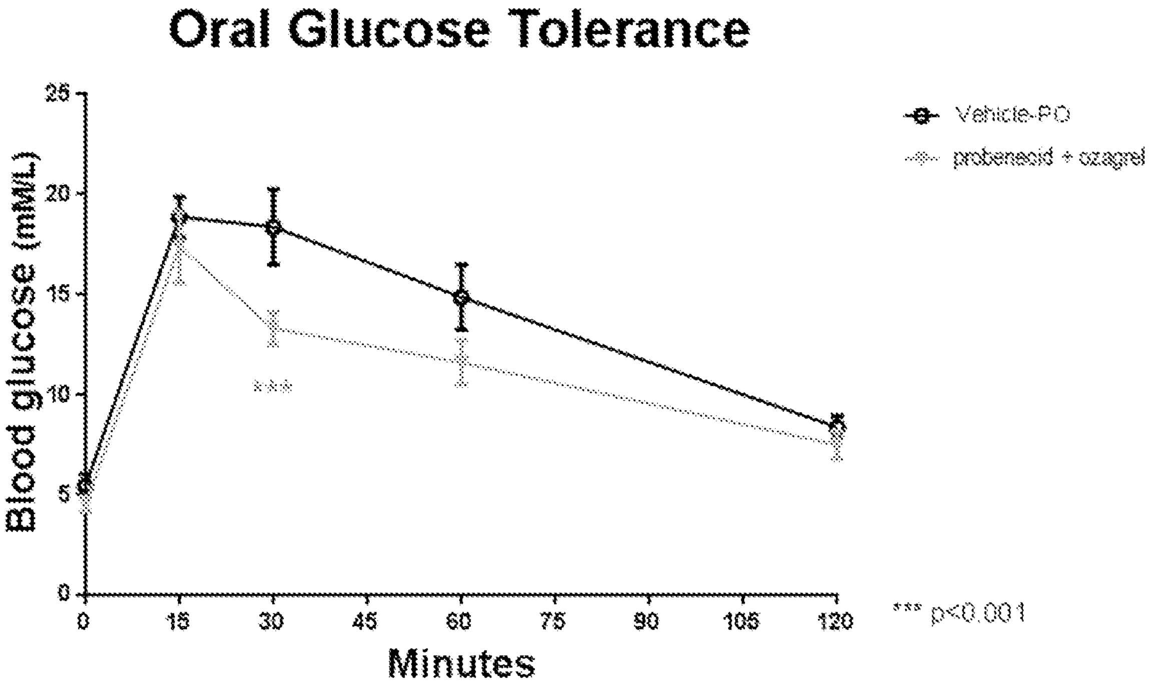

FIG. 34 shows the effects of probenecid (100 mg/kg BW by oral gavage once a day for 3 weeks) in combination with ozagrel (30 mg/kg BW) on glucose tolerance in DIO mice.

Figure 35:
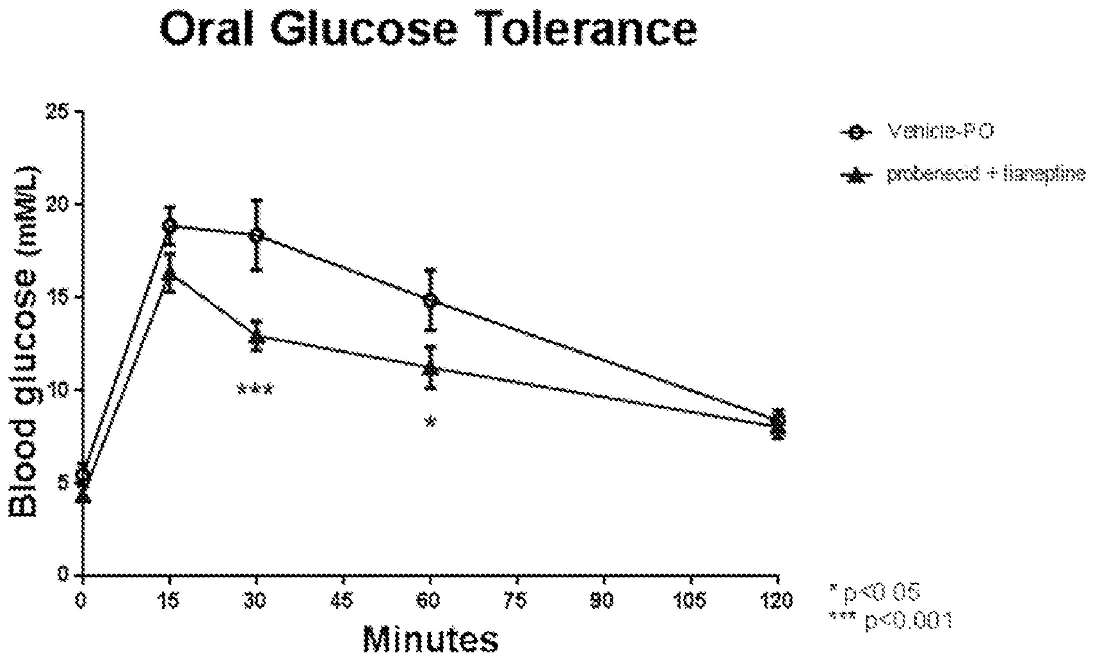

FIG. 35 shows the effects of probenecid (100 mg/kg BW by oral gavage once a day for 3 weeks) in combination with tianeptine (10 mg/kg BW) on glucose tolerance in DIO mice.

Figure 36:
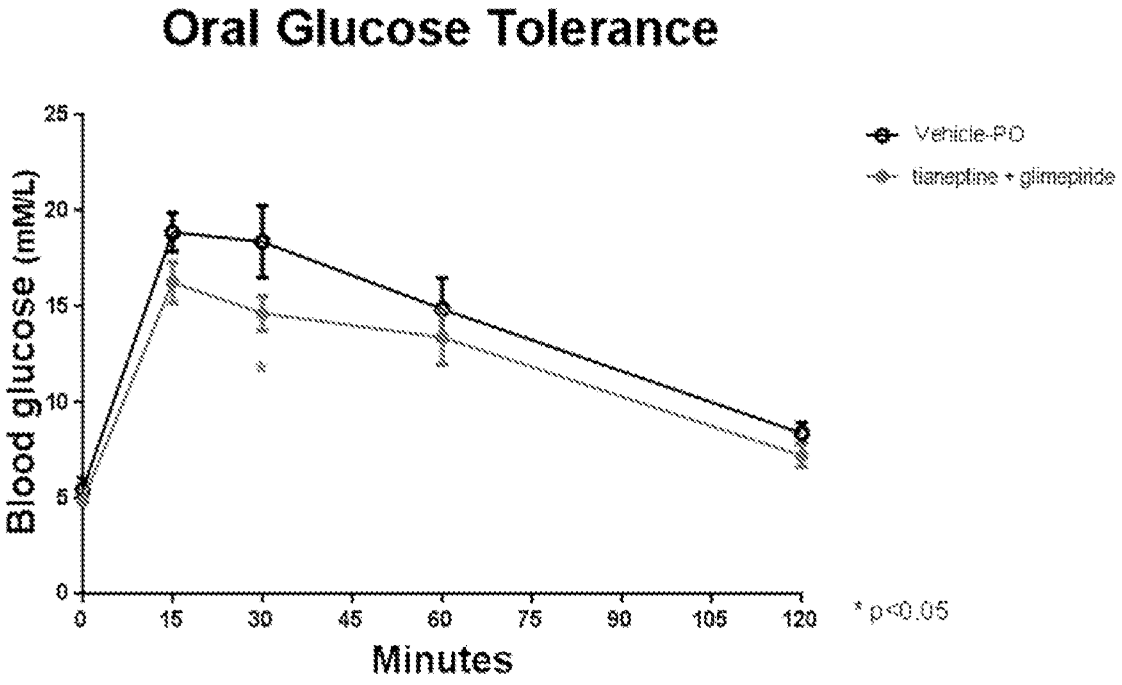

FIG. 36 shows the effects of tianeptine (10 mg/kg BW by oral gavage once a day for 3 weeks) in combination with glimepiride (0.6 mg/kg BW) on glucose tolerance in DIO mice.

Figure 37:
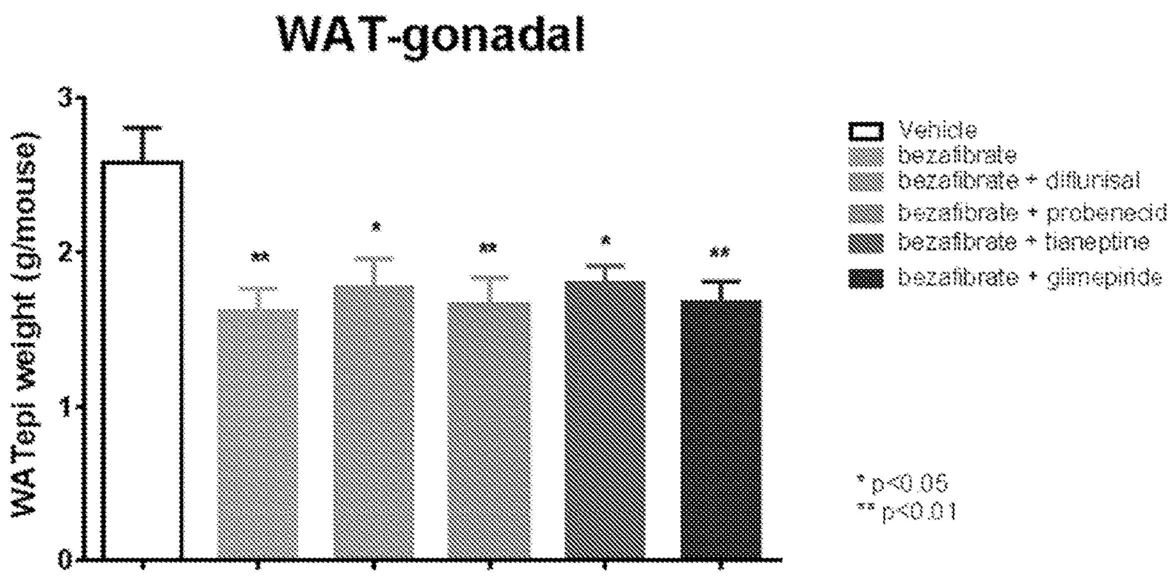

FIG. 37 shows the effects of bezafibrate (115 mg/kg BW by oral gavage once a day for 28 days) alone or in combination with diflunisal (100 mg/kg BW), probenecid (100 mg/kg BW), tianeptine (10 mg/kg BW) or glimepiride (0.6 mg/kg BW) on perigonadal (epididymal) adipose depot size in DIO mice.

Figure 38:
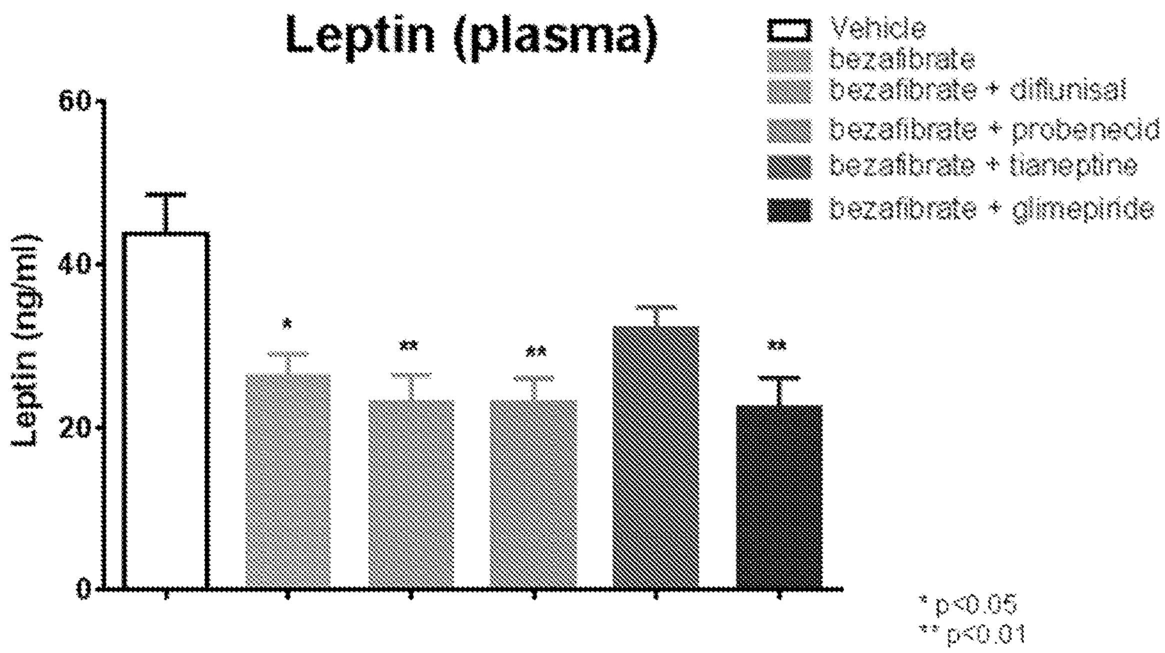

FIG. 38 shows the effects of bezafibrate (115 mg/kg BW by oral gavage once a day for 28 days) alone or in combination with diflunisal (100 mg/kg BW), probenecid (100 mg/kg BW), tianeptine (10 mg/kg BW) or glimepiride (0.6 mg/kg BW) on plasma leptin levels in DIO mice.

Figure 39:
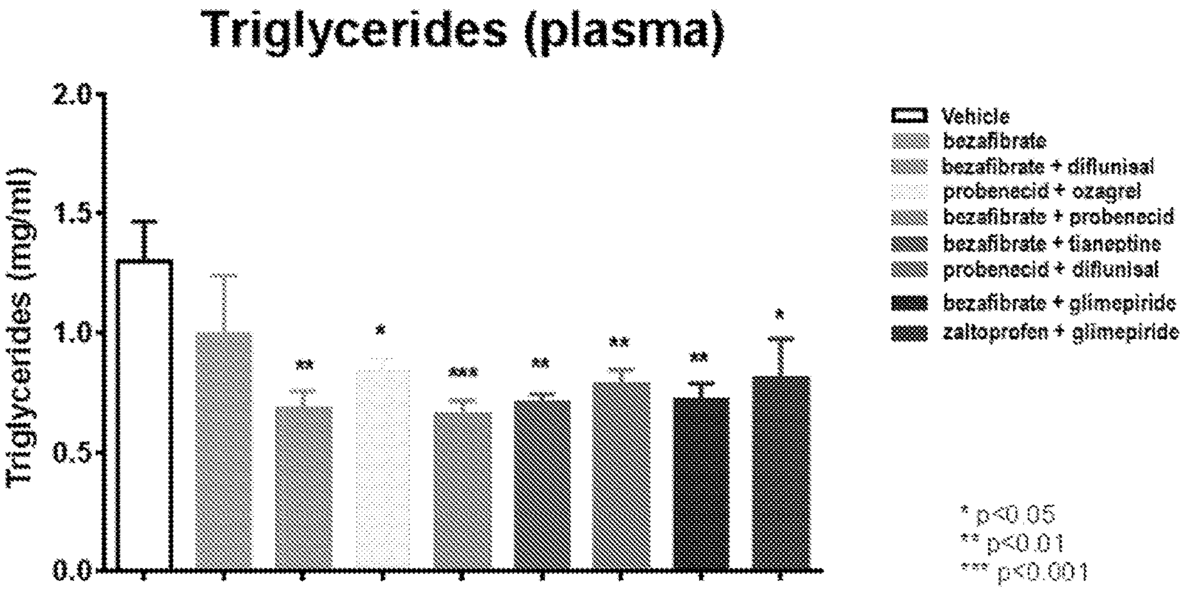

FIG. 39 shows the effects of bezafibrate (115 mg/kg BW by oral gavage once a day for 28 days) alone or in combination with diflunisal (100 mg/kg BW), probenecid (100 mg/kg BW), tianeptine (10 mg/kg BW) or glimepiride (0.6 mg/kg BW) or probenecid (100 mg/kg BW) in combination with ozagrel (30 mg/kg BW) or diflunisal (100 mg/kg BW), or zaltoprofen (50 mg/kg BW) in combination with glimepiride (0.6 mg/kg BW) on plasma triglyceride levels in DIO mice.

Figure 40:
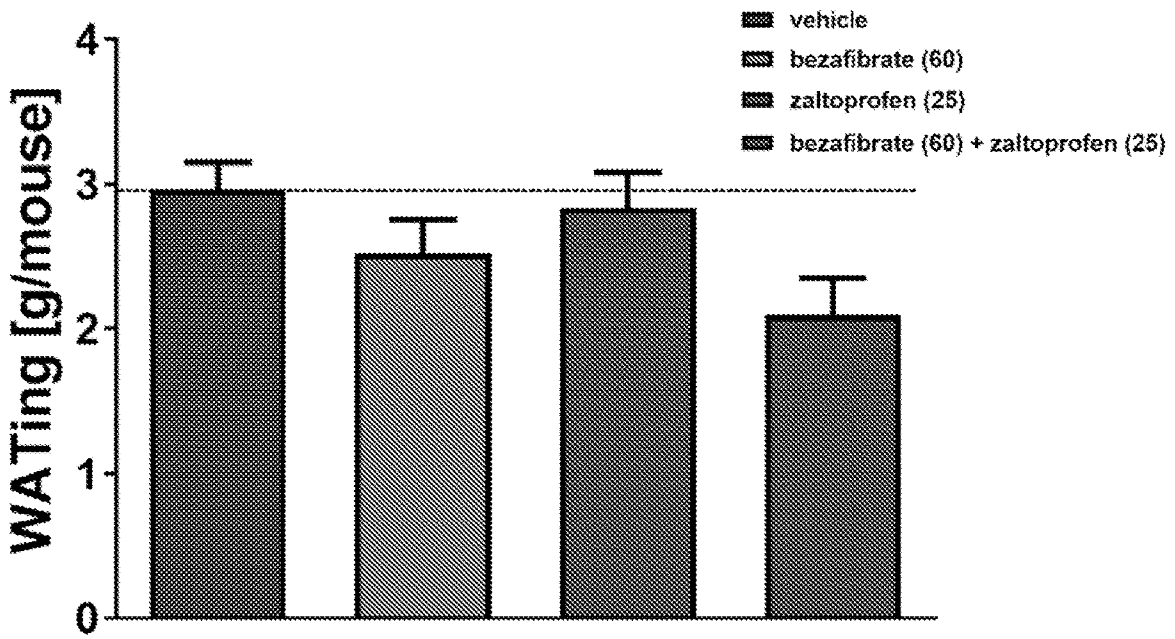

FIG. 40 shows the effects of the combination of bezafibrate (60 mg/kg BW by oral gavage once a day) and zaltoprofen (25 mg/kg BW by oral gavage once a day) on inguinal subcutaneous fat pad mass (WATing) in DIO mice.

Figure 41:
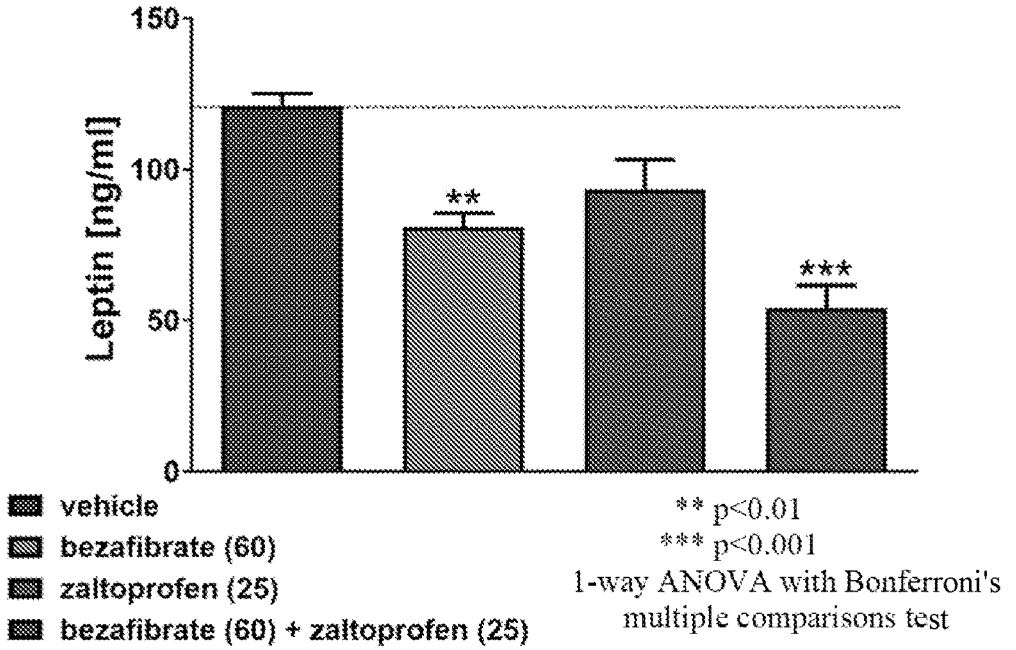

FIG. 41 shows the effects of the combination of bezafibrate (60 mg/kg BW by oral gavage once a day) and zaltoprofen (25 mg/kg BW by oral gavage once a day) on plasma leptin levels in DIO mice.

Figure 42:
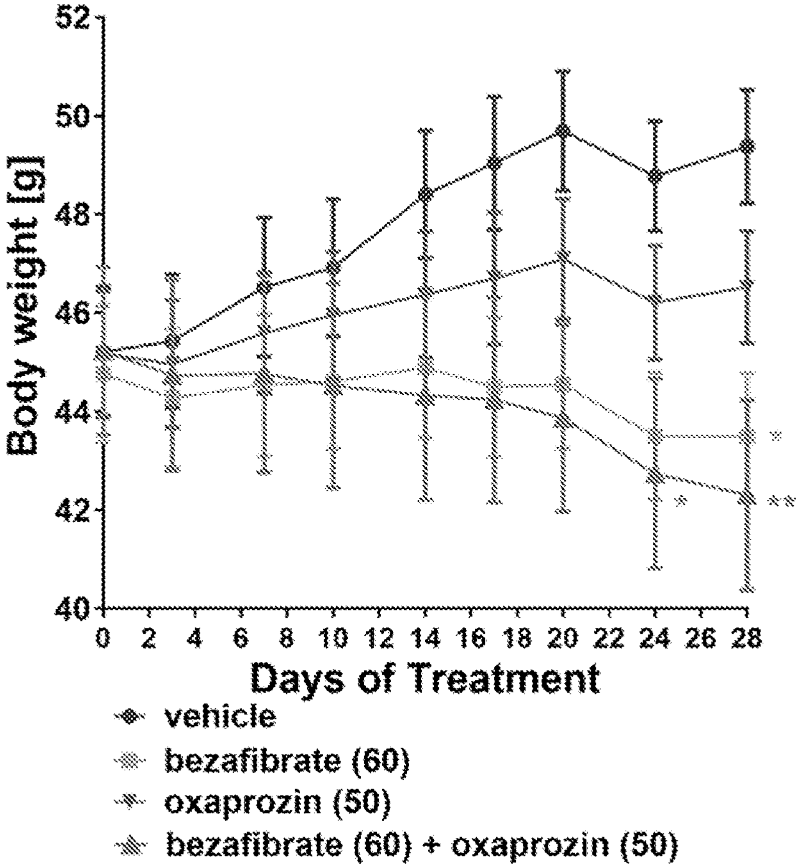

FIG. 42 shows the effects of the combination of bezafibrate (60 mg/kg BW by oral gavage once a day) and oxaprozin (50 mg/kg BW by oral gavage once a day) on body weight in DIO mice.

Figure 43:
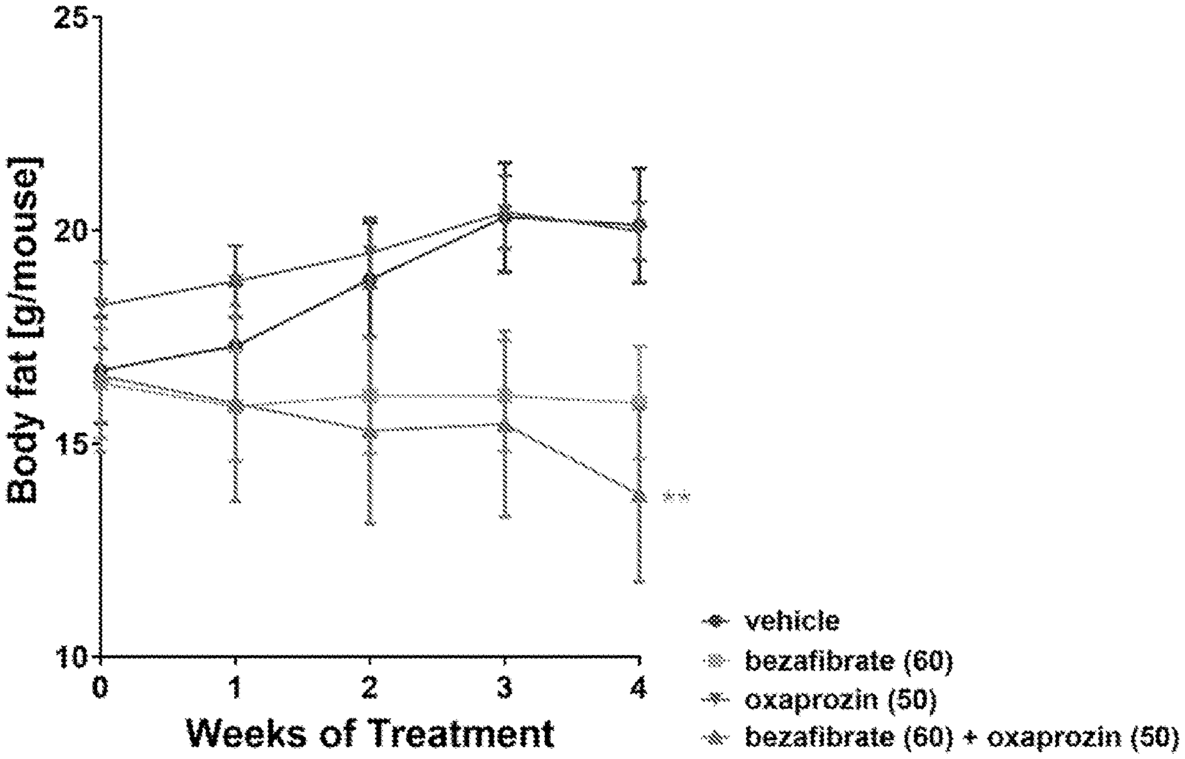

FIG. 43 shows the effects of the combination of bezafibrate (60 mg/kg BW by oral gavage once a day) and oxaprozin (50 mg/kg BW by oral gavage once a day) on body fat content in DIO mice.

Figure 44:
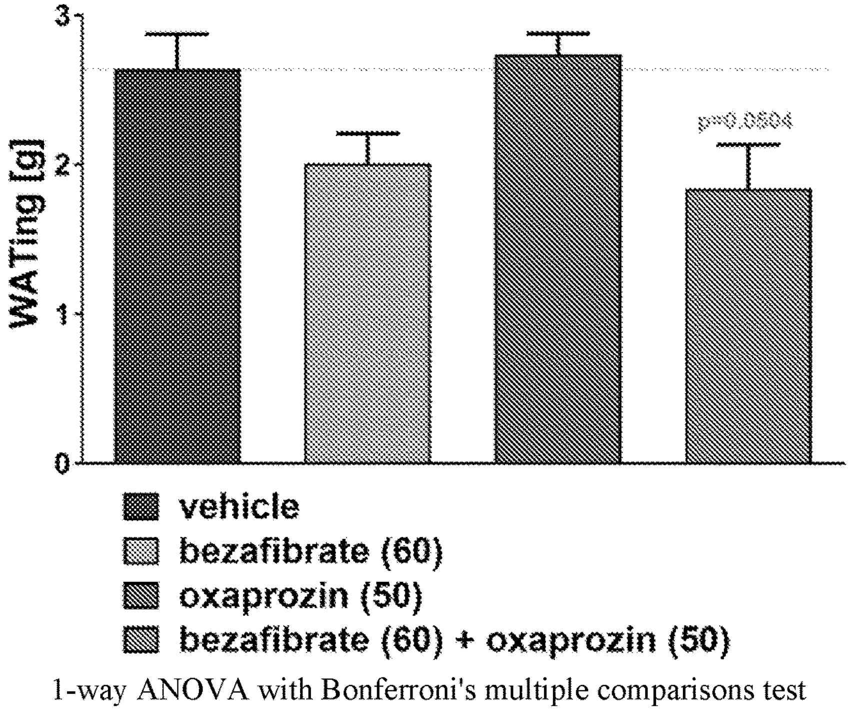

FIG. 44 shows the effects of the combination of bezafibrate (60 mg/kg BW by oral gavage once a day) and oxaprozin (50 mg/kg BW by oral gavage once a day) on inguinal subcutaneous fat pad mass (WATing) in DIO mice.

Figure 45:
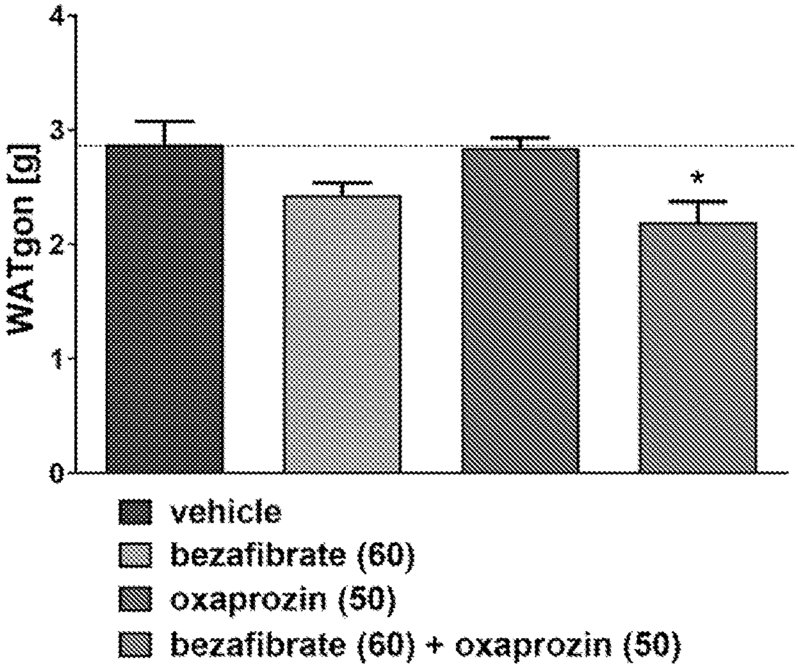

FIG. 45 shows the effects of the combination of bezafibrate (60 mg/kg BW by oral gavage once a day) and oxaprozin (50 mg/kg BW by oral gavage once a day) on gonadal visceral fat pad mass (WATing) in DIO mice.

Figure 46:
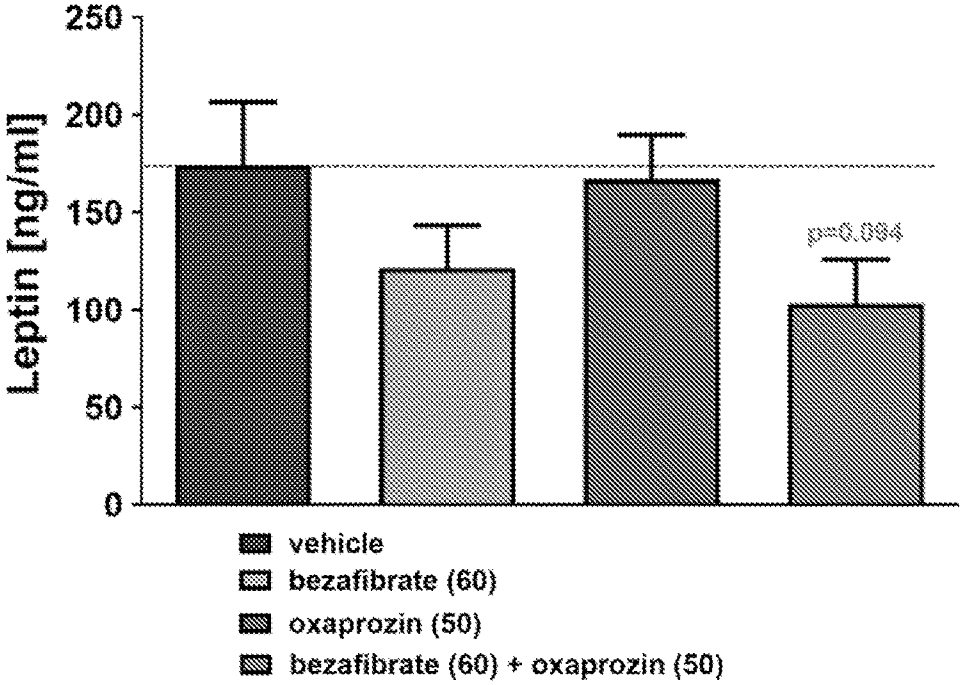

FIG. 46 shows the effects of the combination of bezafibrate (60 mg/kg BW by oral gavage once a day) and oxaprozin (50 mg/kg BW by oral gavage once a day) on plasma leptin levels in DIO mice.

Figure 47:
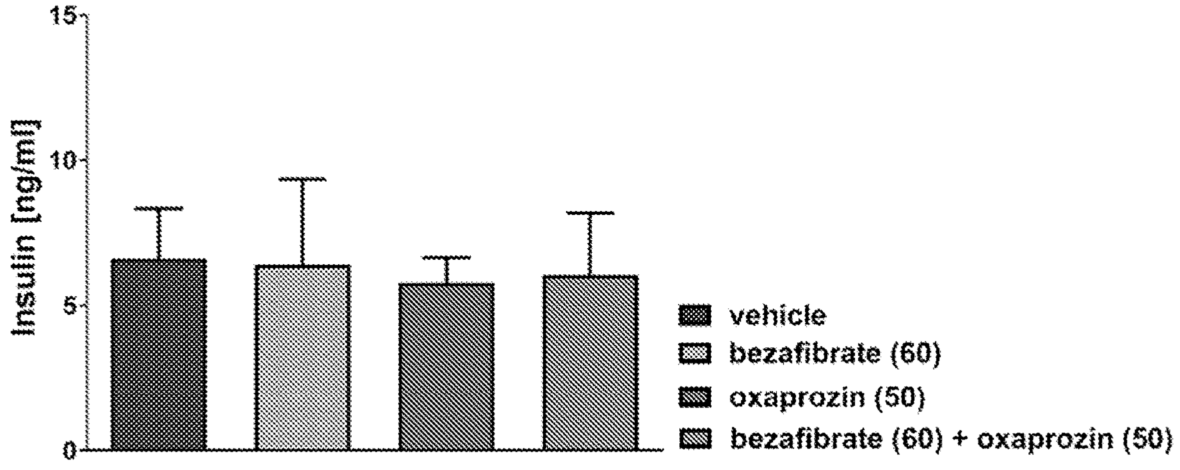

FIG. 47 shows baseline (predosing) levels of fed plasma insulin in the DIO mice used for dosing with the respective agents.

Figure 48:
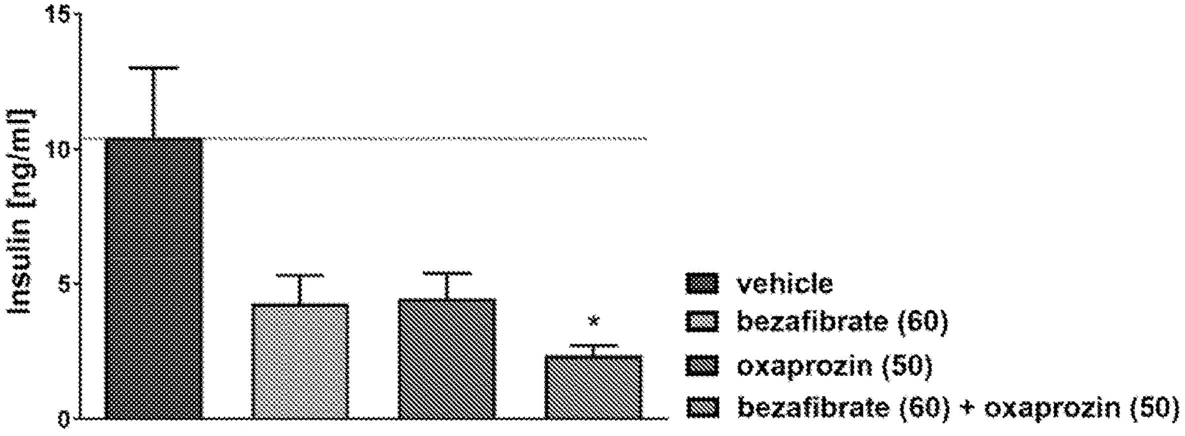

FIG. 48 shows the effects of the combination of bezafibrate (60 mg/kg BW by oral gavage once a day) and oxaprozin (50 mg/kg BW by oral gavage once a day) on fed plasma insulin levels in DIO mice.

Figure 49:
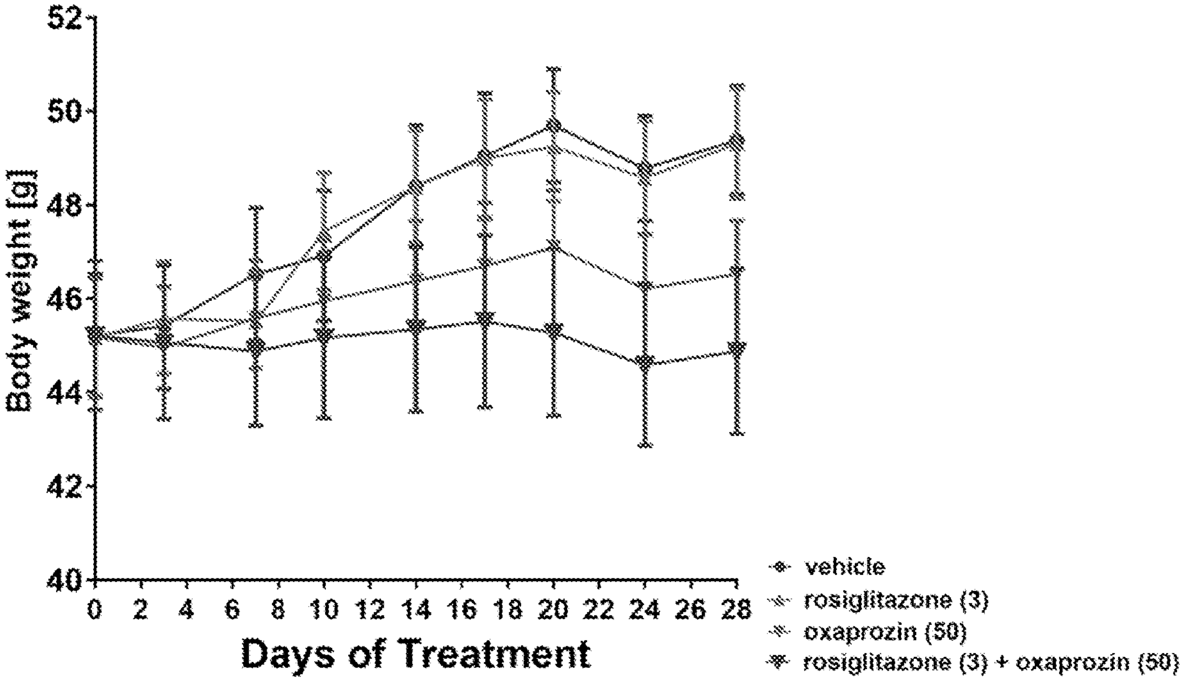

FIG. 49 shows the effects of the combination of rosiglitazone (3 mg/kg BW by oral gavage once a day) and oxaprozin (50 mg/kg BW by oral gavage once a day) on body weight in DIO mice.

Figure 50:
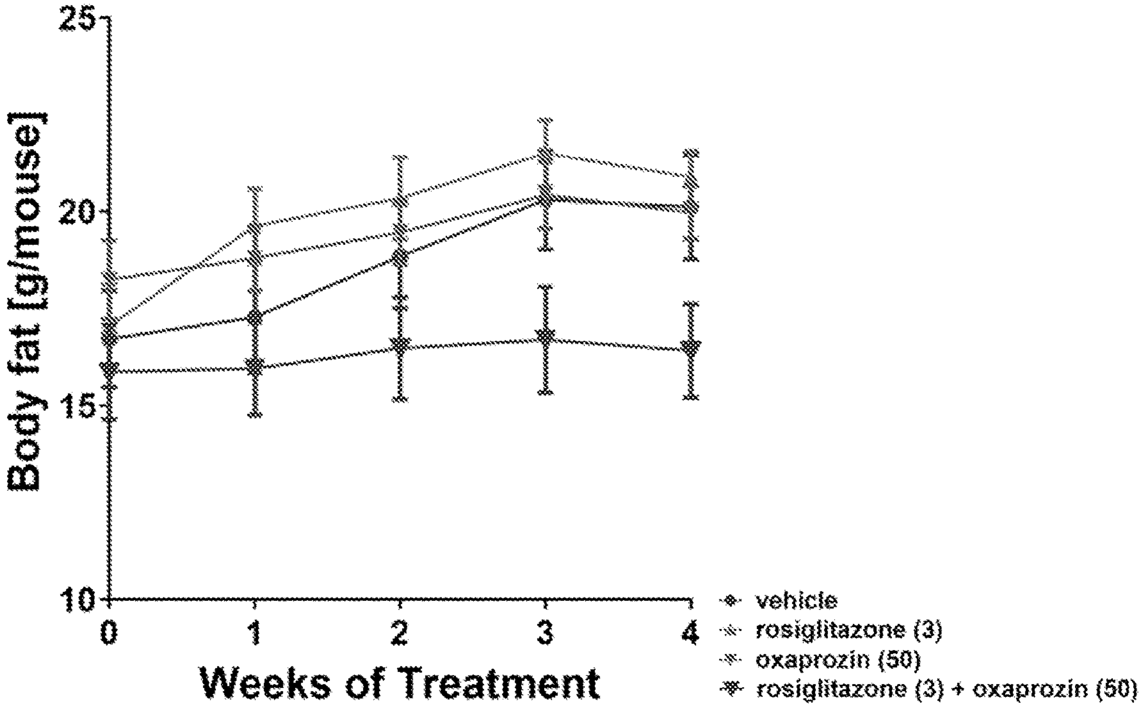

FIG. 50 shows the effects of the combination of rosiglitazone (3 mg/kg BW by oral gavage once a day) and oxaprozin (50 mg/kg BW by oral gavage once a day) on body fat content in DIO mice.

Figure 51:
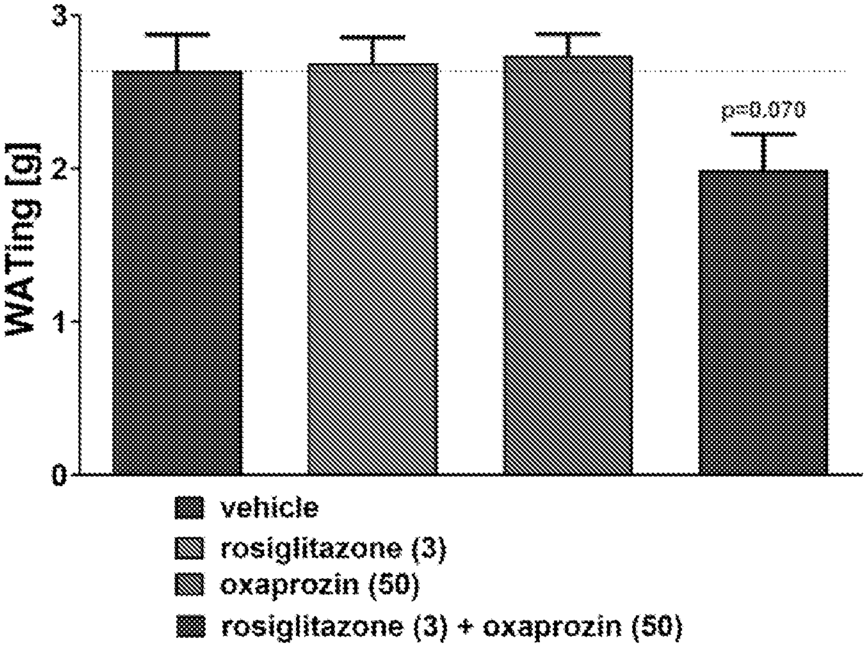

FIG. 51 shows the effects of the combination of rosiglitazone (3 mg/kg BW by oral gavage once a day) and oxaprozin (50 mg/kg BW by oral gavage once a day) on inguinal subcutaneous fat pad mass (WATing) in DIO mice.

Figure 52:
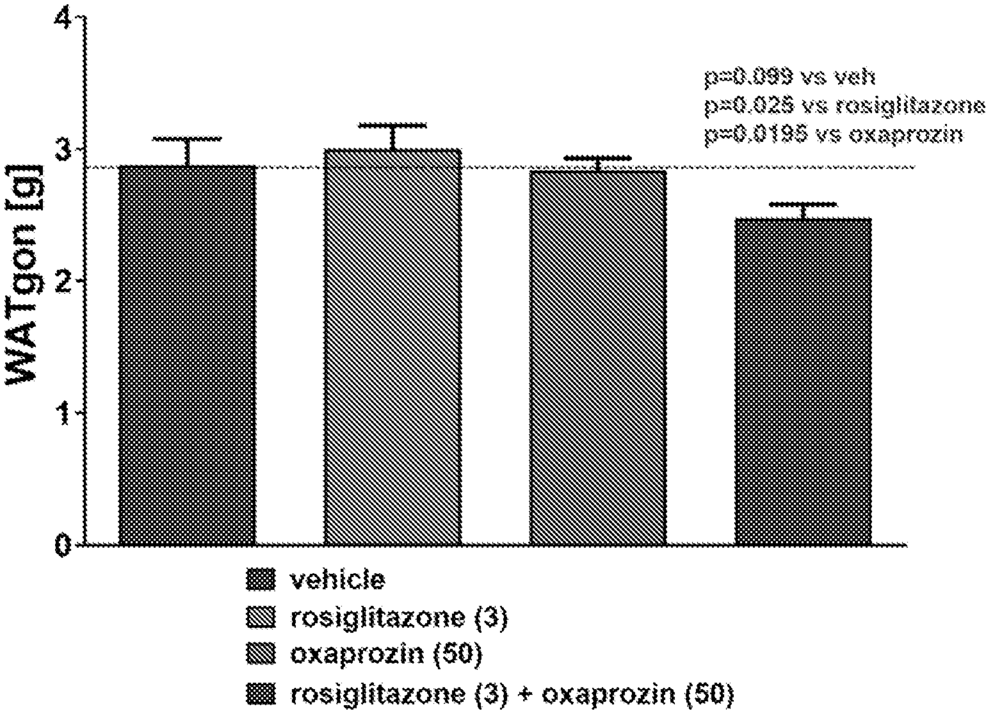

FIG. 52 shows the effects of the combination of rosiglitazone (3 mg/kg BW by oral gavage once a day) and oxaprozin (50 mg/kg BW by oral gavage once a day) on gonadal visceral fat pad mass (WATing) in DIO mice.

Figure 53:
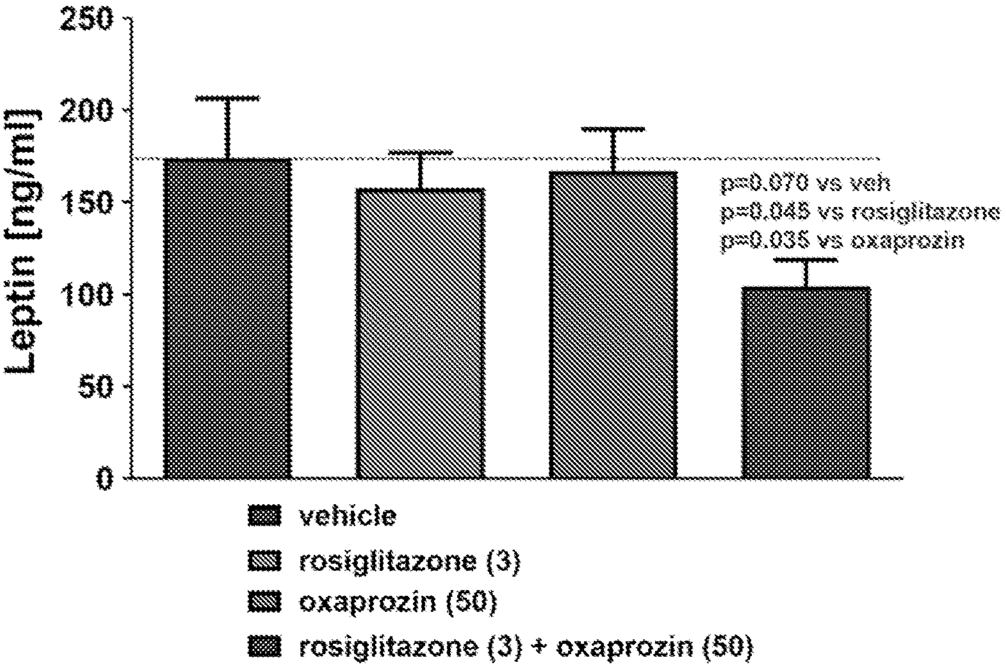

FIG. 53 shows the effects of the combination of rosiglitazone (3 mg/kg BW by oral gavage once a day) and oxaprozin (50 mg/kg BW by oral gavage once a day) on plasma leptin levels in DIO mice.

Figure 54:
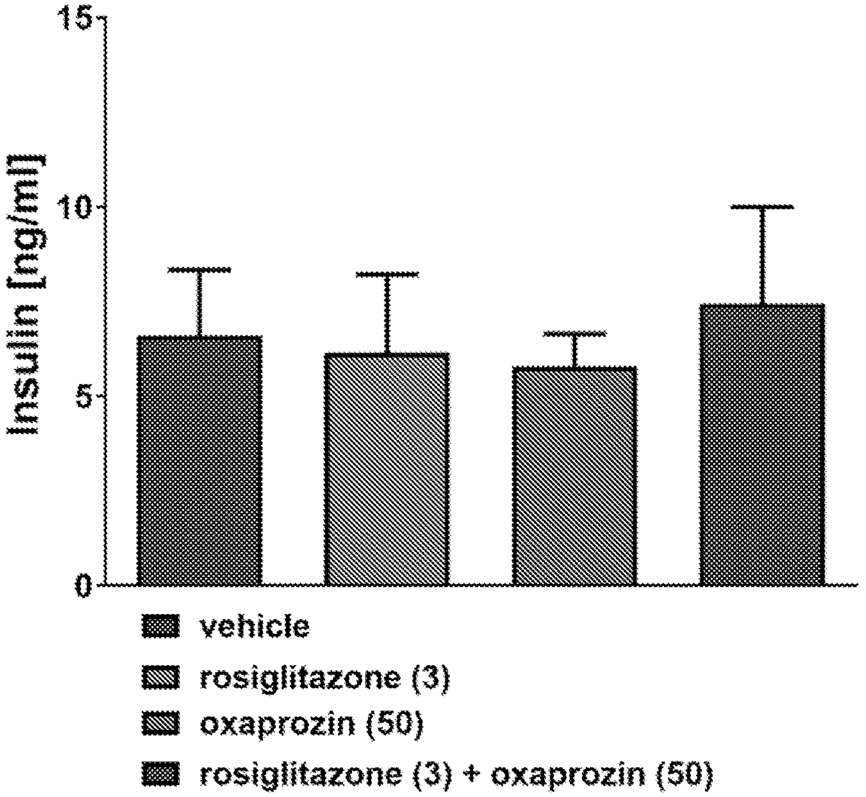

FIG. 54 shows baseline (predosing) levels of fed plasma insulin in the DIO mice used for dosing with the respective agents.

Figure 55:
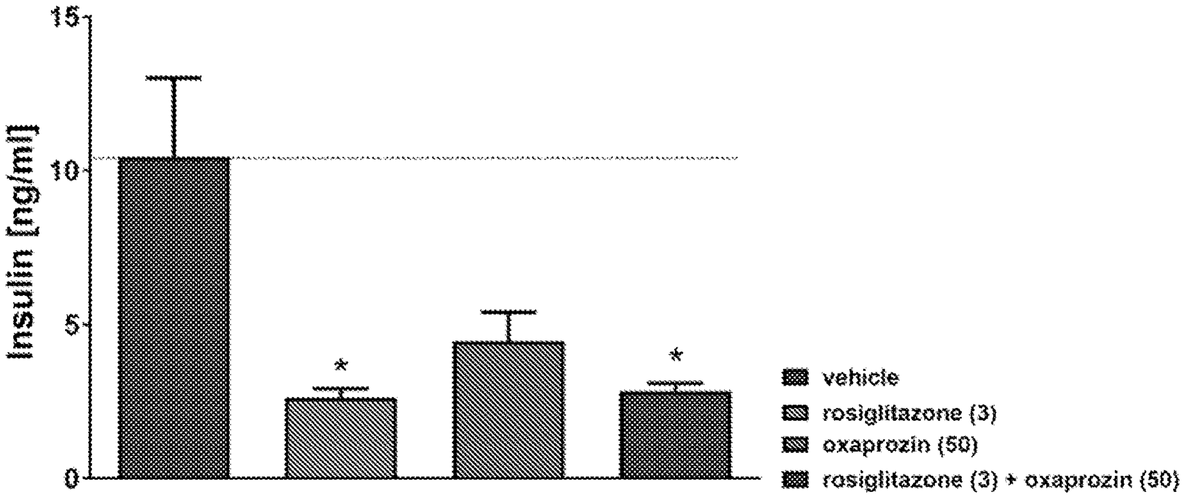

FIG. 55 shows the effects of the combination of rosiglitazone (3 mg/kg BW by oral gavage once a day) and oxaprozin (50 mg/kg BW by oral gavage once a day) on fed plasma insulin levels in DIO mice.

Figure 56:
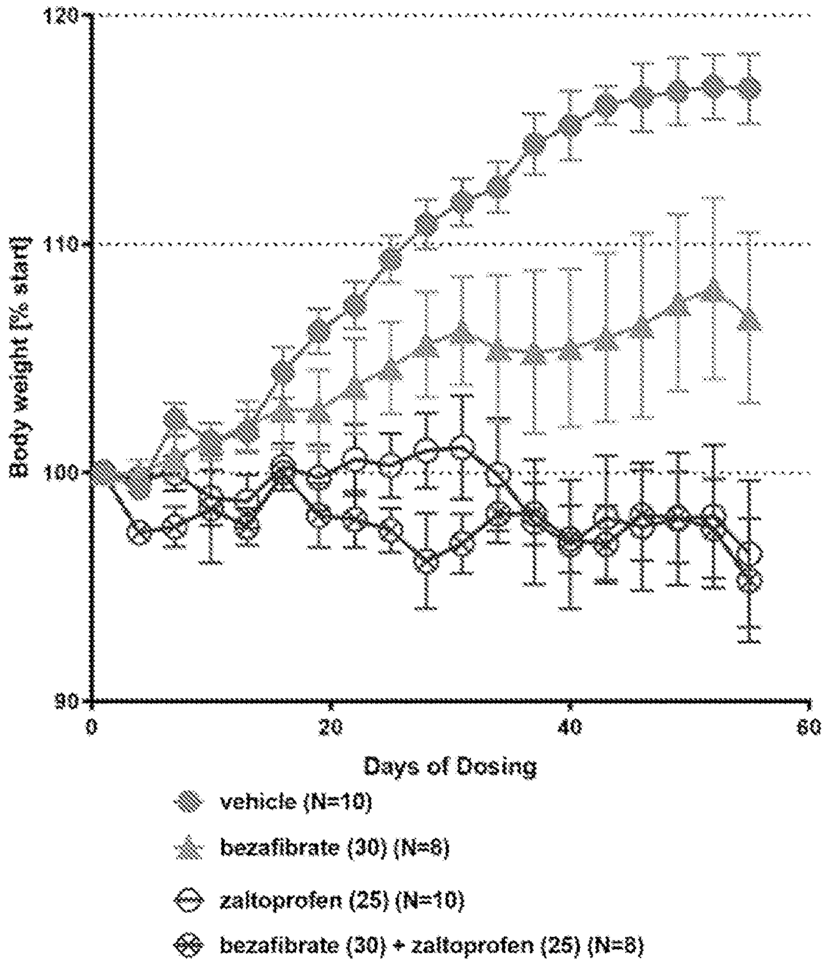

FIG. 56 shows the effects of the combination of bezafibrate (30 mg/kg BW by oral gavage once a day) and zaltoprofen (25 mg/kg BW by oral gavage once a day) on body weight in DIO mice.

Figure 57:
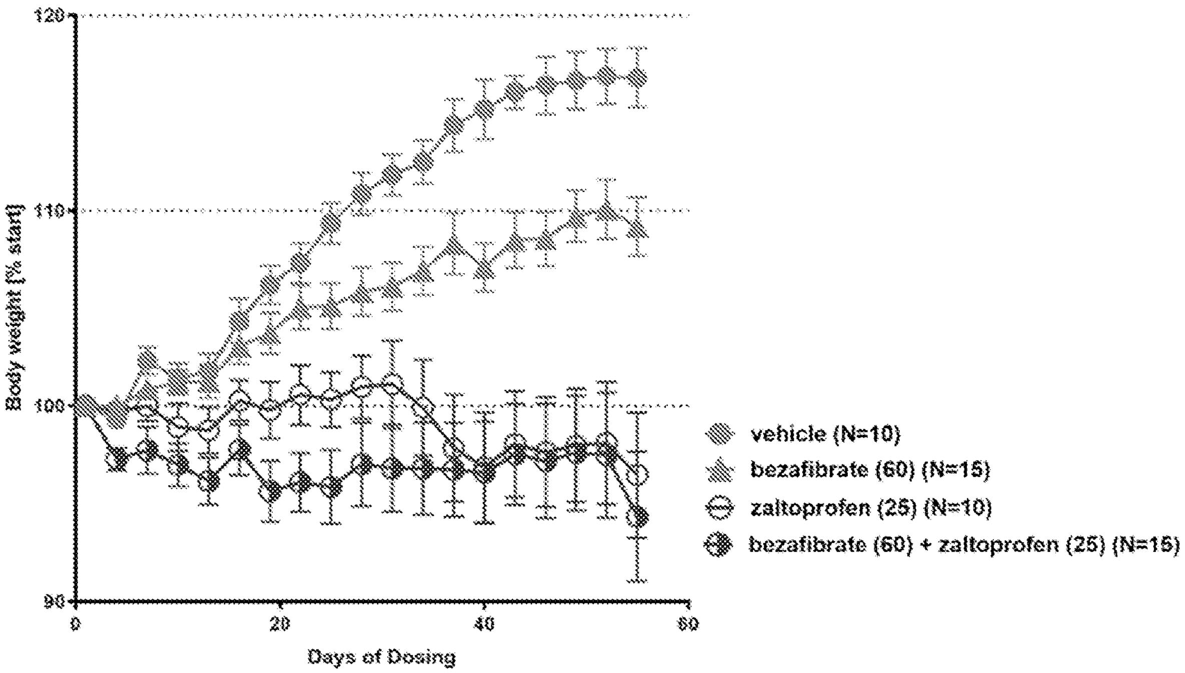

FIG. 57 shows the effects of the combination of bezafibrate (60 mg/kg BW by oral gavage once a day) and zaltoprofen (25 mg/kg BW by oral gavage once a day) on body weight in DIO mice.

Figure 58:
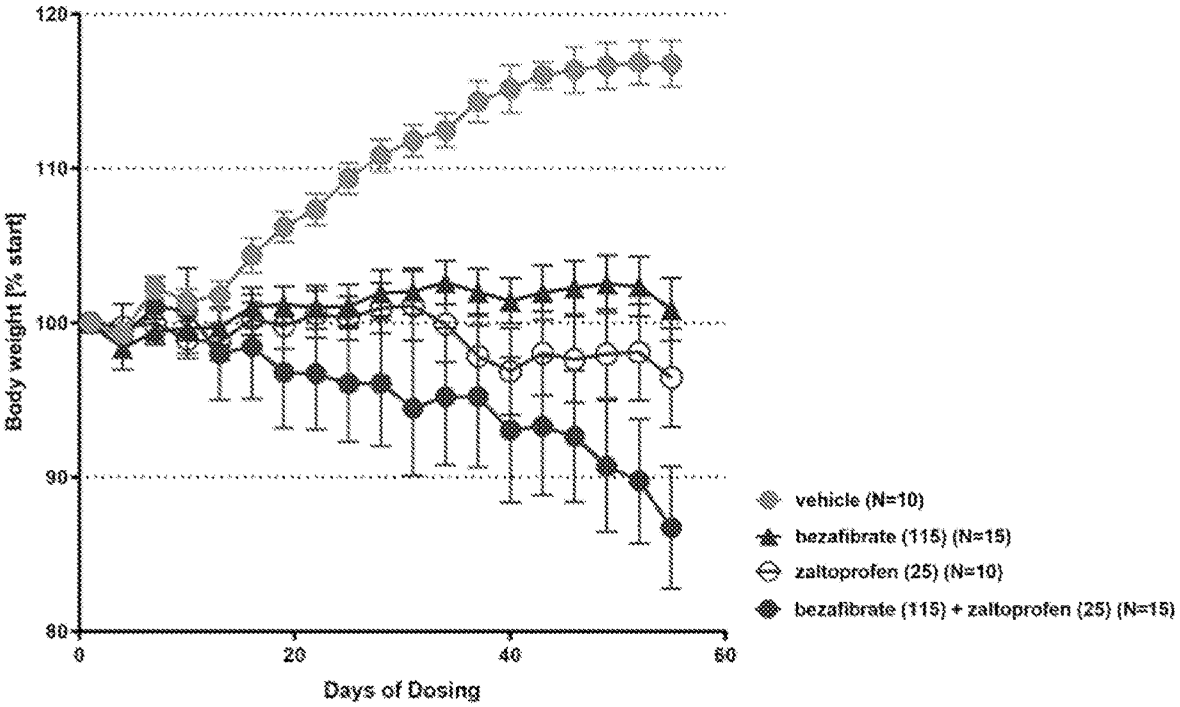

FIG. 58 shows the effects of the combination of bezafibrate (115 mg/kg BW by oral gavage once a day) and zaltoprofen (25 mg/kg BW by oral gavage once a day) on body weight in DIO mice.

Figure 59:
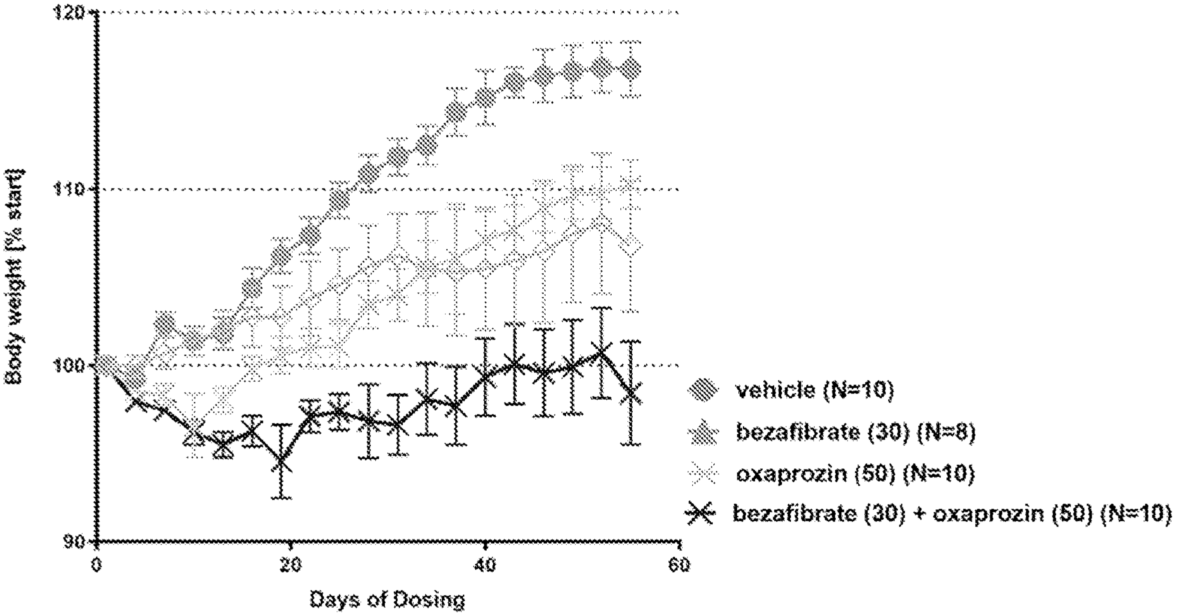

FIG. 59 shows the effects of the combination of bezafibrate (30 mg/kg BW by oral gavage once a day) and oxaprozin (50 mg/kg BW by oral gavage once a day) on body weight in DIO mice.

Figure 60:
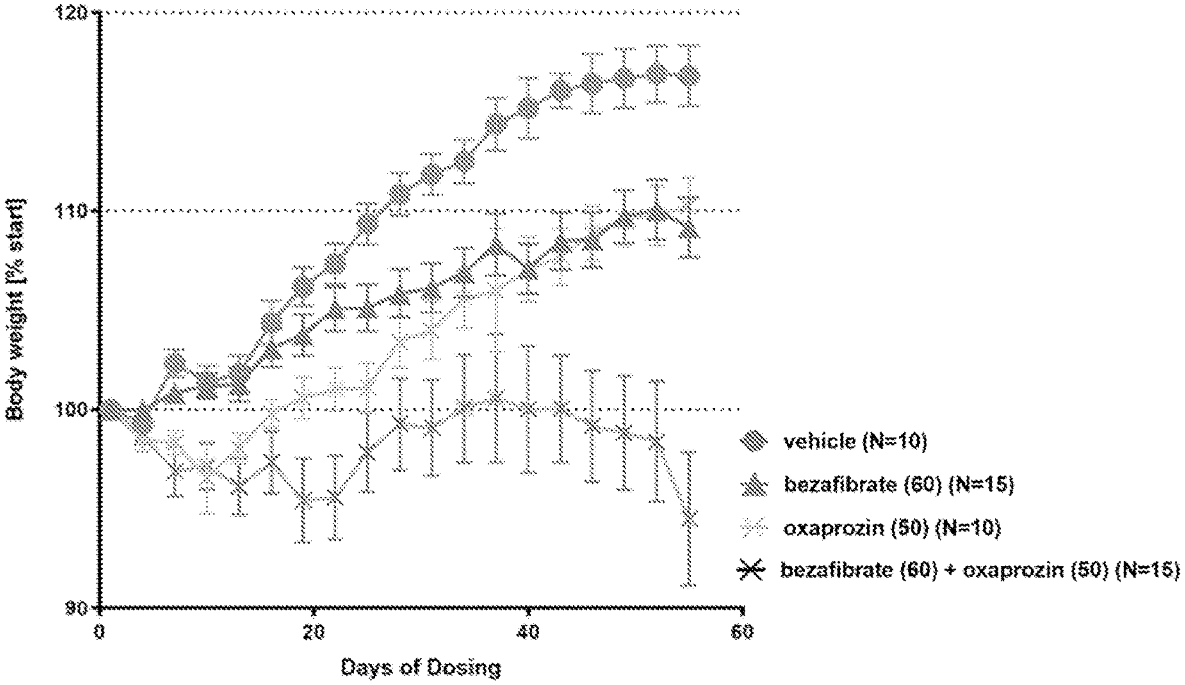

FIG. 60 shows the effects of the combination of bezafibrate (60 mg/kg BW by oral gavage once a day) and oxaprozin (50 mg/kg BW by oral gavage once a day) on body weight in DIO mice.

Figure 61:
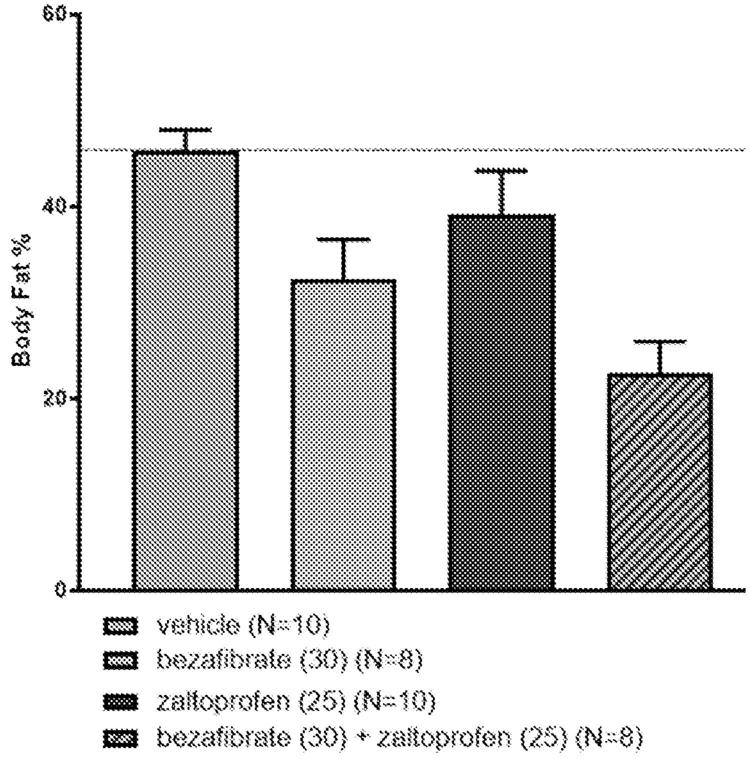

FIG. 61 shows the effects of the combination of bezafibrate (30 mg/kg BW by oral gavage once a day) and zaltoprofen (25 mg/kg BW by oral gavage once a day) on body fat (measured by MRI) in DIO mice.

Figure 62:
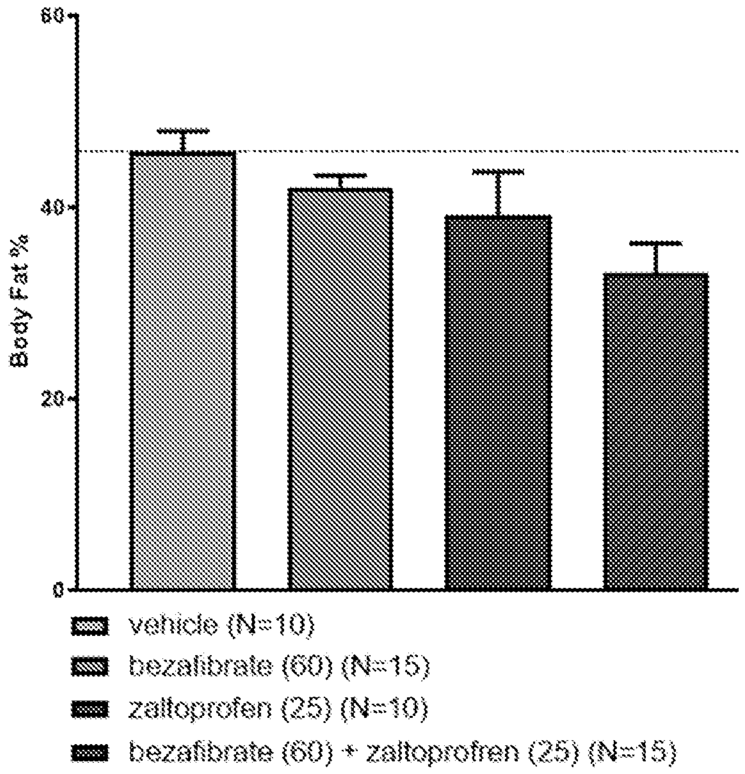

FIG. 62 shows the effects of the combination of bezafibrate (60 mg/kg BW by oral gavage once a day) and zaltoprofen (25 mg/kg BW by oral gavage once a day) on body fat (measured by MRI) in DIO mice.

Figure 63:
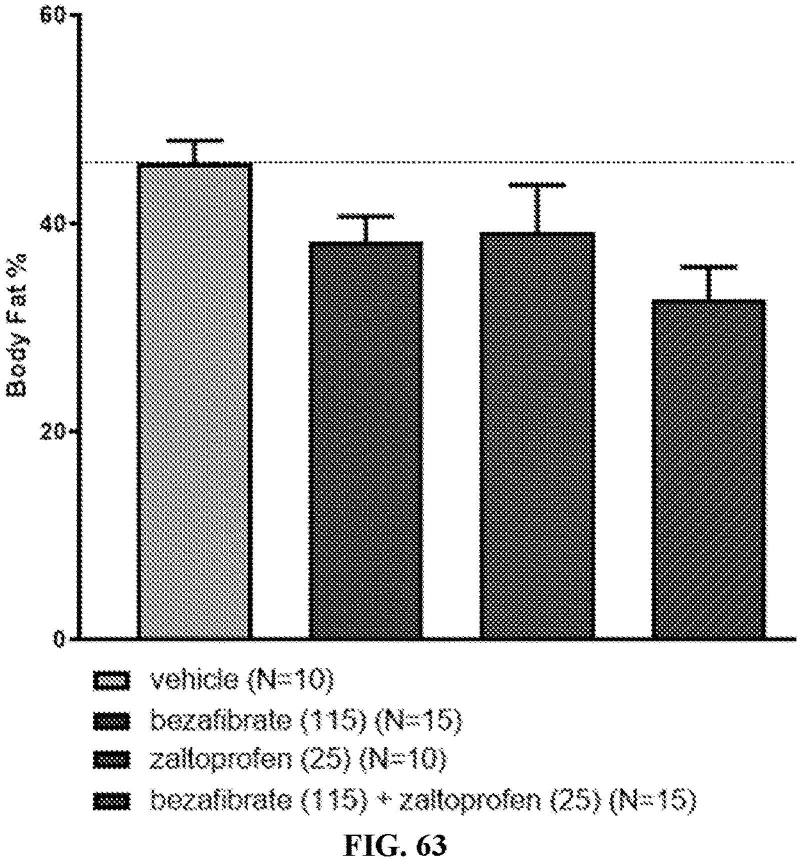

FIG. 63 shows the effects of the combination of bezafibrate (115 mg/kg BW by oral gavage once a day) and zaltoprofen (25 mg/kg BW by oral gavage once a day) on body fat (measured by MRI) in DIO mice.

Figure 64:
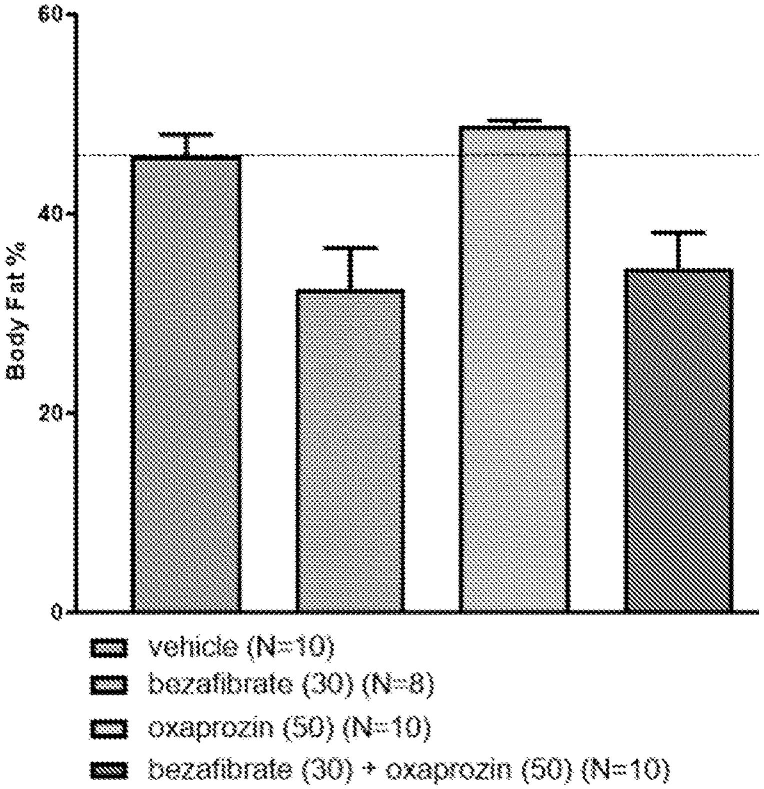

FIG. 64 shows the effects of the combination of bezafibrate (30 mg/kg BW by oral gavage once a day) and oxaprozin (50 mg/kg BW by oral gavage once a day) on body fat (measured by MRI) in DIO mice.

Figure 65:
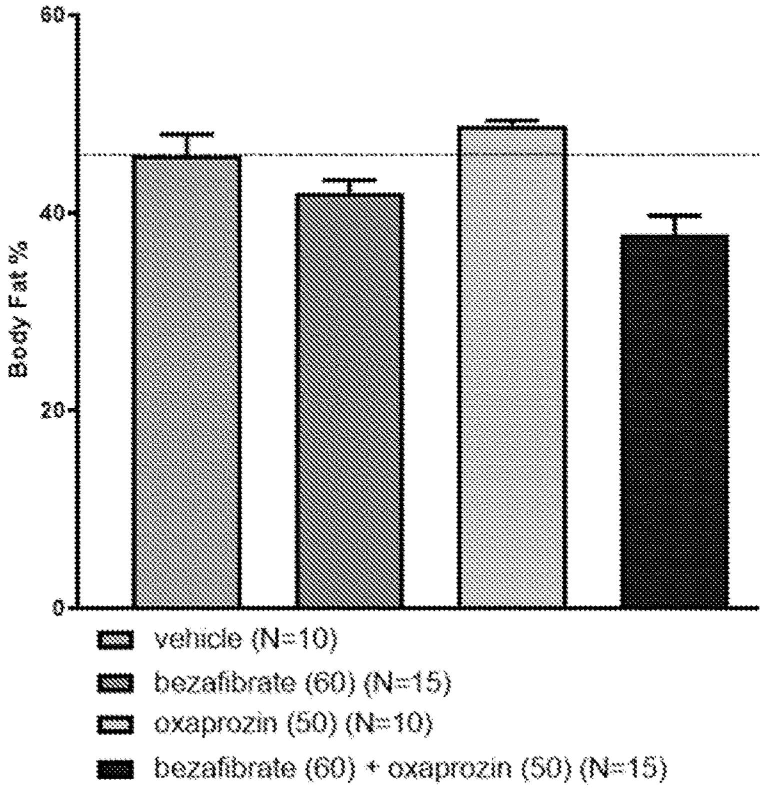

FIG. 65 shows the effects of the combination of bezafibrate (60 mg/kg BW by oral gavage once a day) and oxaprozin (50 mg/kg BW by oral gavage once a day) on body fat (measured by medical resonance imaging, MRI) in DIO mice. Bezafibrate (60)+oxaprozin (50) synergistically lowered body fat mass (p=0.048).

Figure 66:
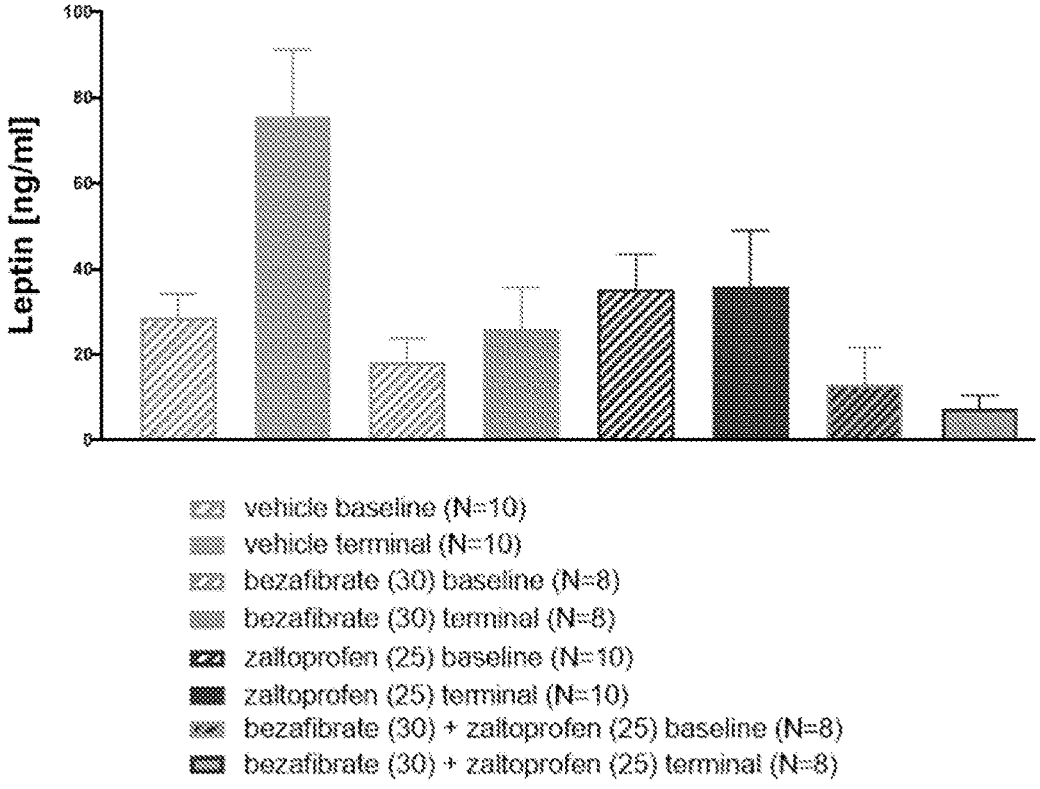

FIG. 66 shows the effects of the combination of bezafibrate (30 mg/kg BW by oral gavage once a day) and zaltoprofen (25 mg/kg BW by oral gavage once a day)) on plasma leptin levels in DIO mice.

Figure 67:
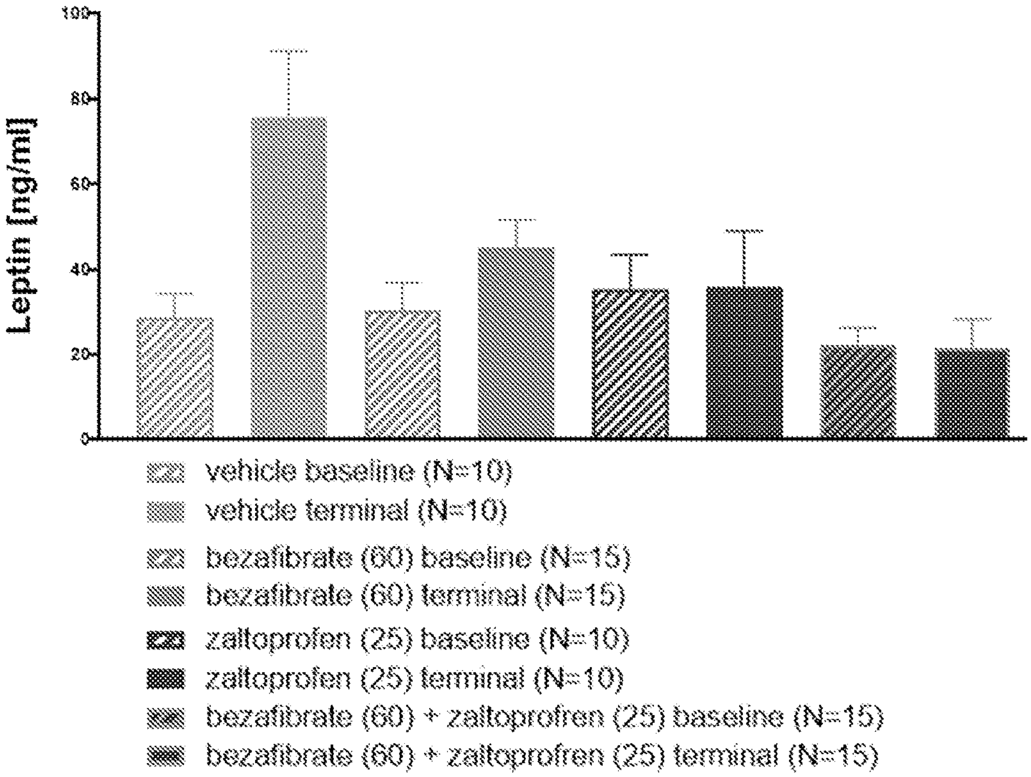

FIG. 67 shows the effects of the combination of bezafibrate (60 mg/kg BW by oral gavage once a day) and zaltoprofen (25 mg/kg BW by oral gavage once a day) on plasma leptin levels in DIO mice.

Figure 68:
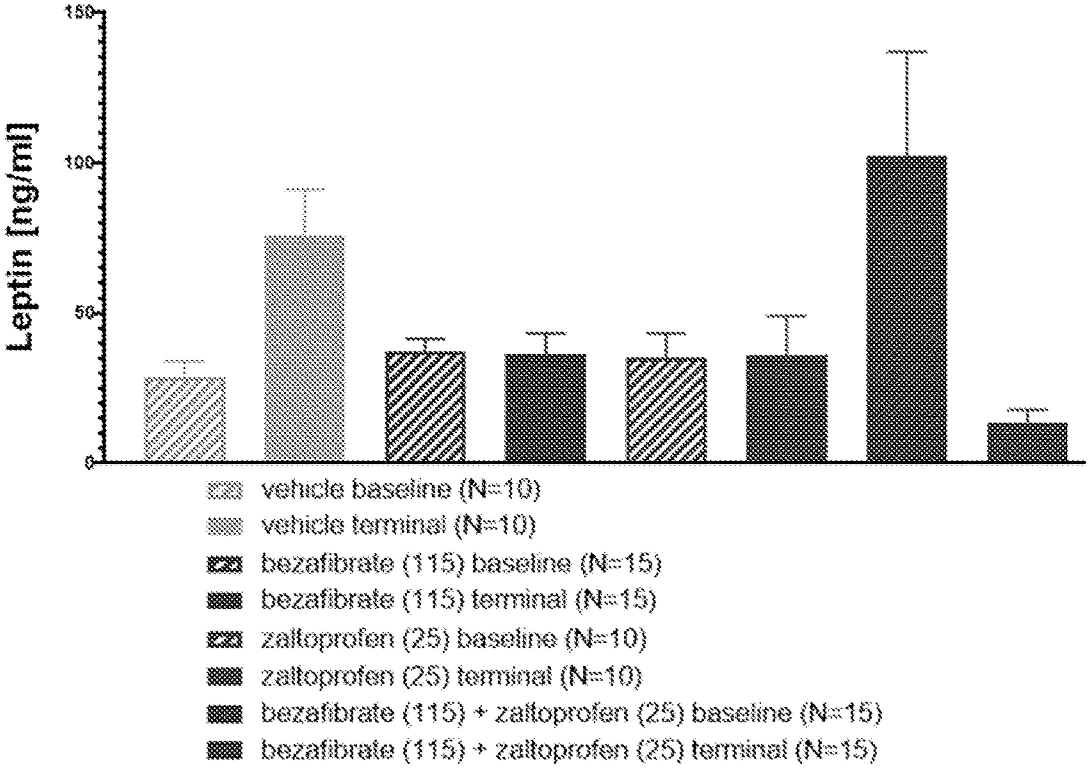

FIG. 68 shows the effects of the combination of bezafibrate (115 mg/kg BW by oral gavage once a day) and zaltoprofen (25 mg/kg BW by oral gavage once a day) on plasma leptin levels in DIO mice.

Figure 69:
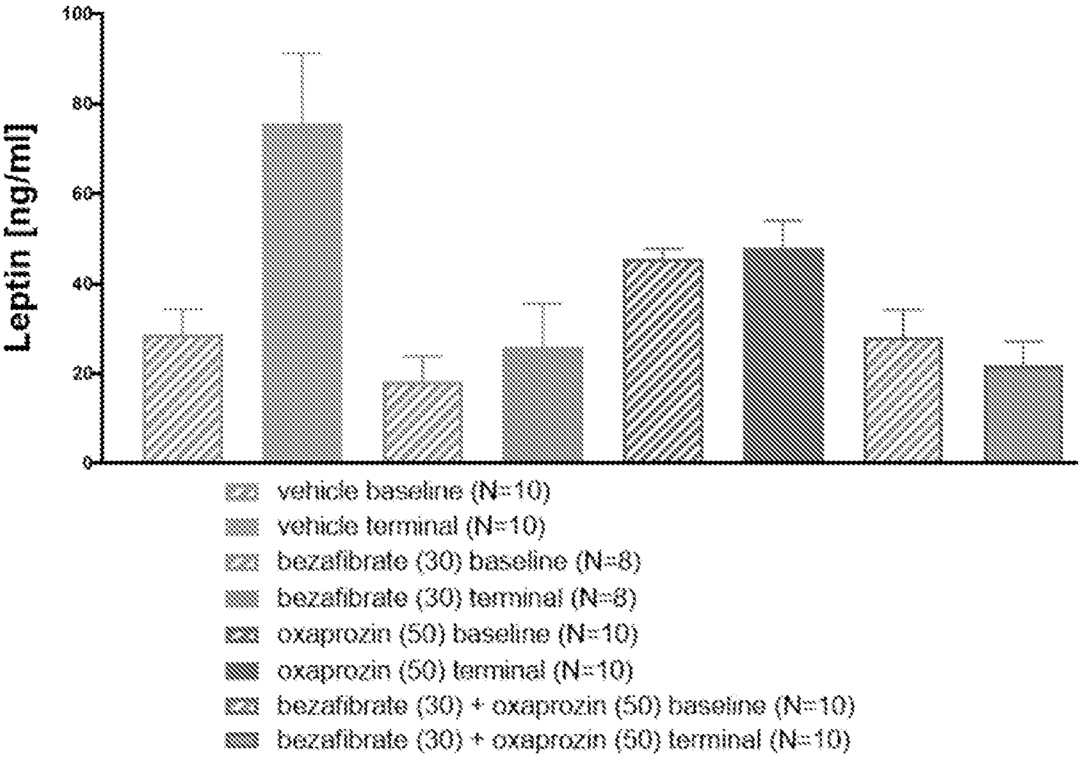

FIG. 69 shows the effects of the combination of bezafibrate (30 mg/kg BW by oral gavage once a day) and oxaprozin (50 mg/kg BW by oral gavage once a day) on plasma leptin levels in DIO mice.

Figure 70:
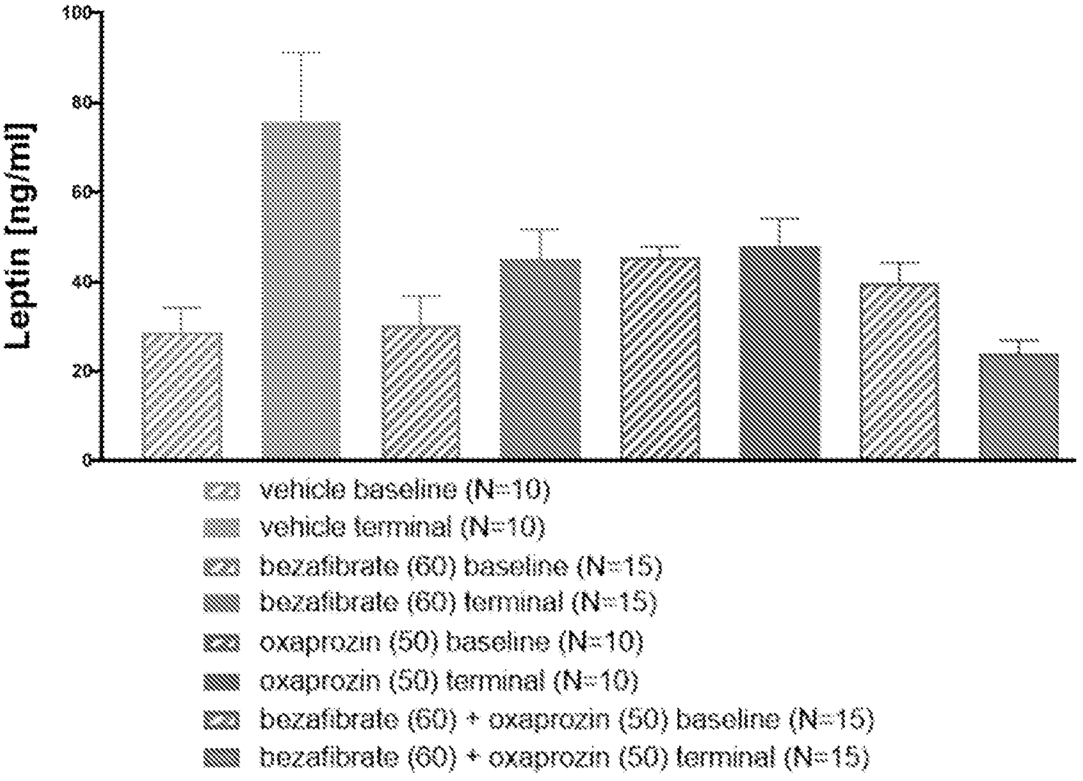

FIG. 70 shows the effects of the combination of bezafibrate (60 mg/kg BW by oral gavage once a day) and oxaprozin (50 mg/kg BW by oral gavage once a day) on plasma leptin levels in DIO mice. The combination dramatically reduced leptin vs vehicle, and the 2 drugs acted synergistically (p=0.001).

Figure 71:
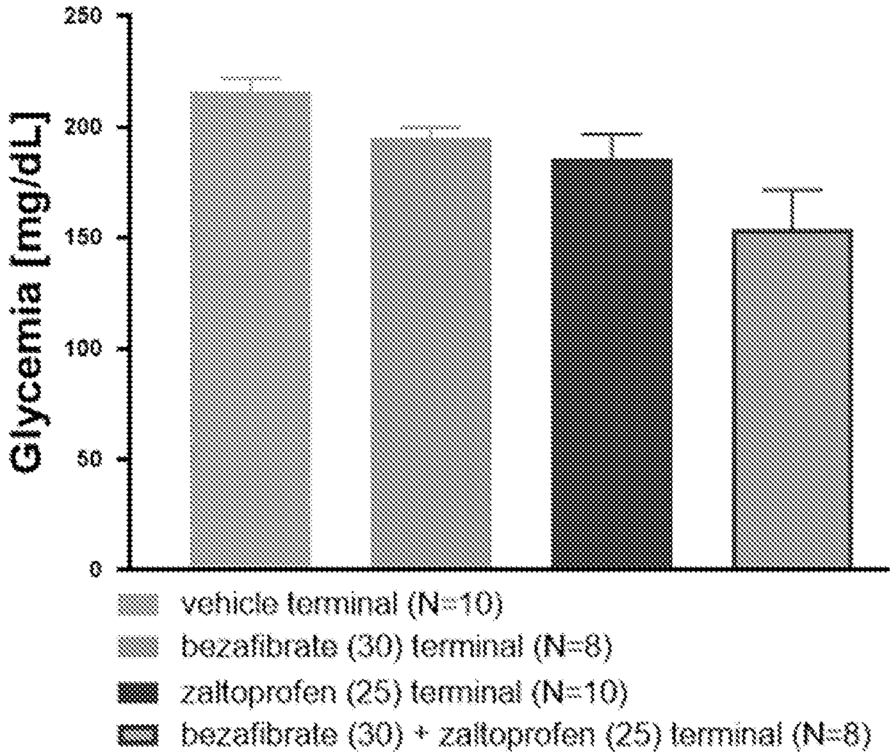

FIG. 71 shows the effects of the combination of bezafibrate (30 mg/kg BW by oral gavage once a day) and zaltoprofen (25 mg/kg BW by oral gavage once a day) on blood glucose levels in DIO mice.

Figure 72:
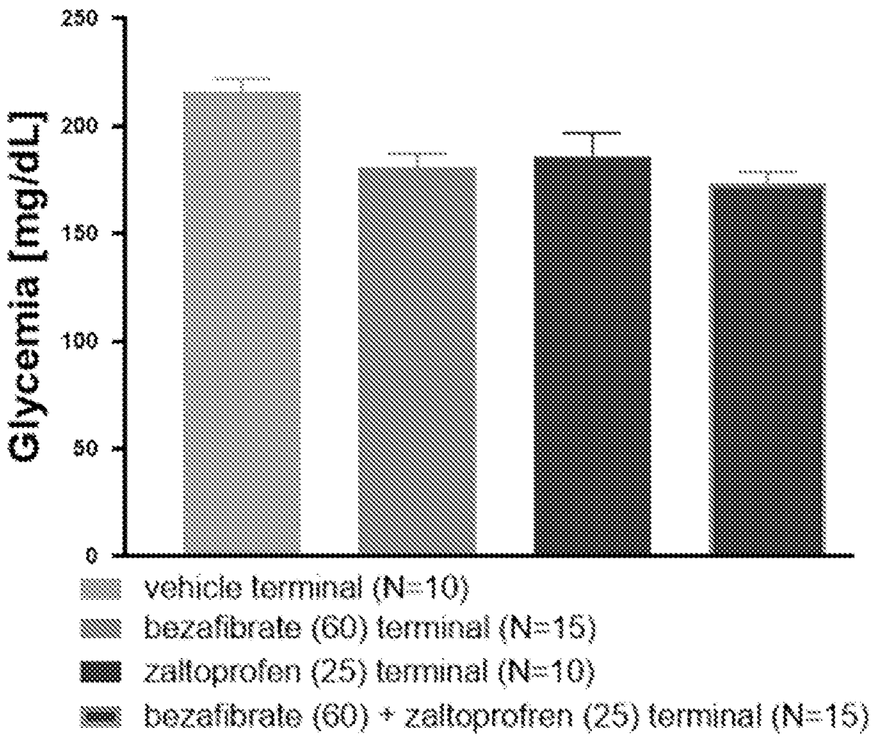

FIG. 72 shows the effects of the combination of bezafibrate (60 mg/kg BW by oral gavage once a day) and zaltoprofen (25 mg/kg BW by oral gavage once a day) on blood glucose levels in DIO mice.

Figure 73:
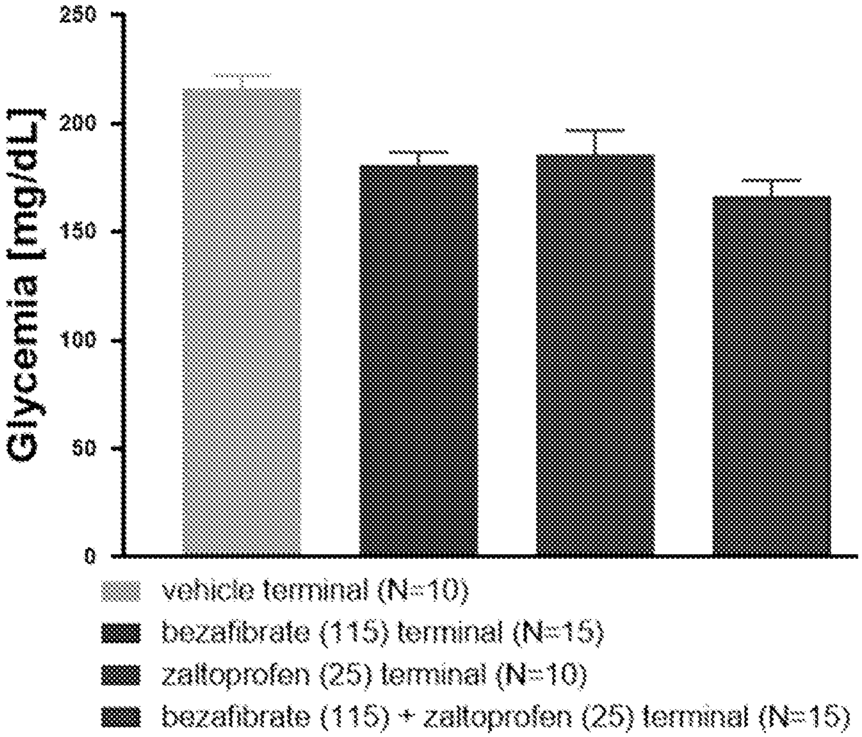

FIG. 73 shows the effects of the combination of bezafibrate (115 mg/kg BW by oral gavage once a day) and zaltoprofen (25 mg/kg BW by oral gavage once a day) on blood glucose levels in DIO mice.

Figure 74:
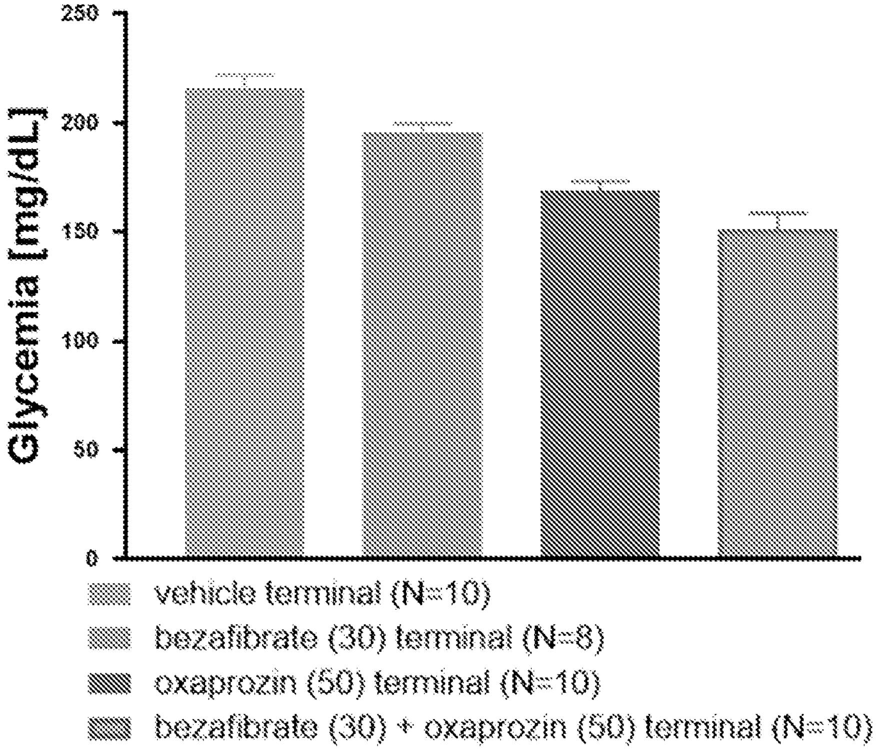

FIG. 74 shows the effects of the combination of bezafibrate (30 mg/kg BW by oral gavage once a day) and oxaprozin (50 mg/kg BW by oral gavage once a day) on blood glucose levels in DIO mice.

Figure 75:
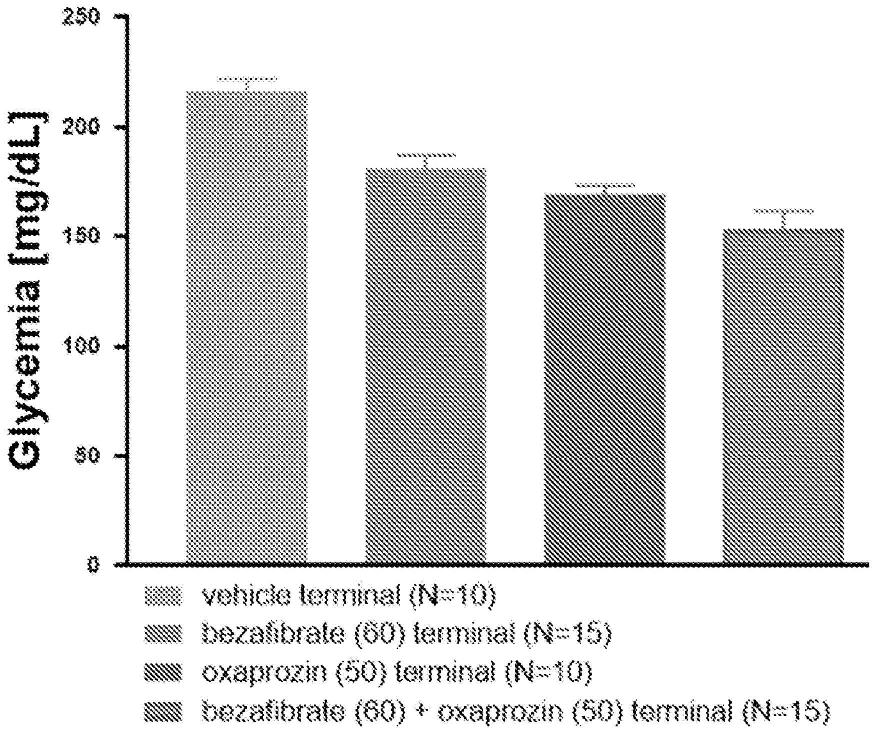

FIG. 75 shows the effects of the combination of bezafibrate (60 mg/kg BW by oral gavage once a day) and oxaprozin (50 mg/kg BW by oral gavage once a day) on blood glucose levels in DIO mice.

Figure 76:
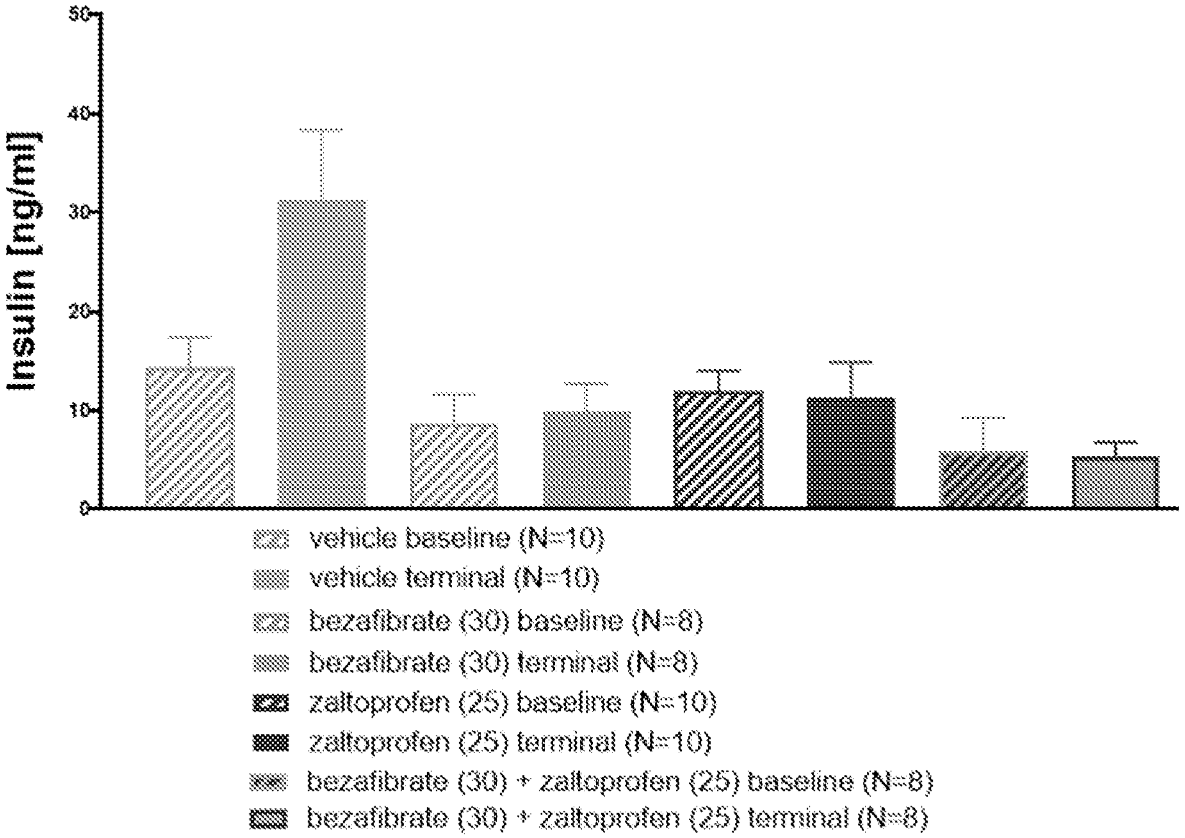

FIG. 76 shows the effects of the combination of bezafibrate (30 mg/kg BW by oral gavage once a day) and zaltoprofen (25 mg/kg BW by oral gavage once a day) on plasma insulin levels in DIO mice.

Figure 77:
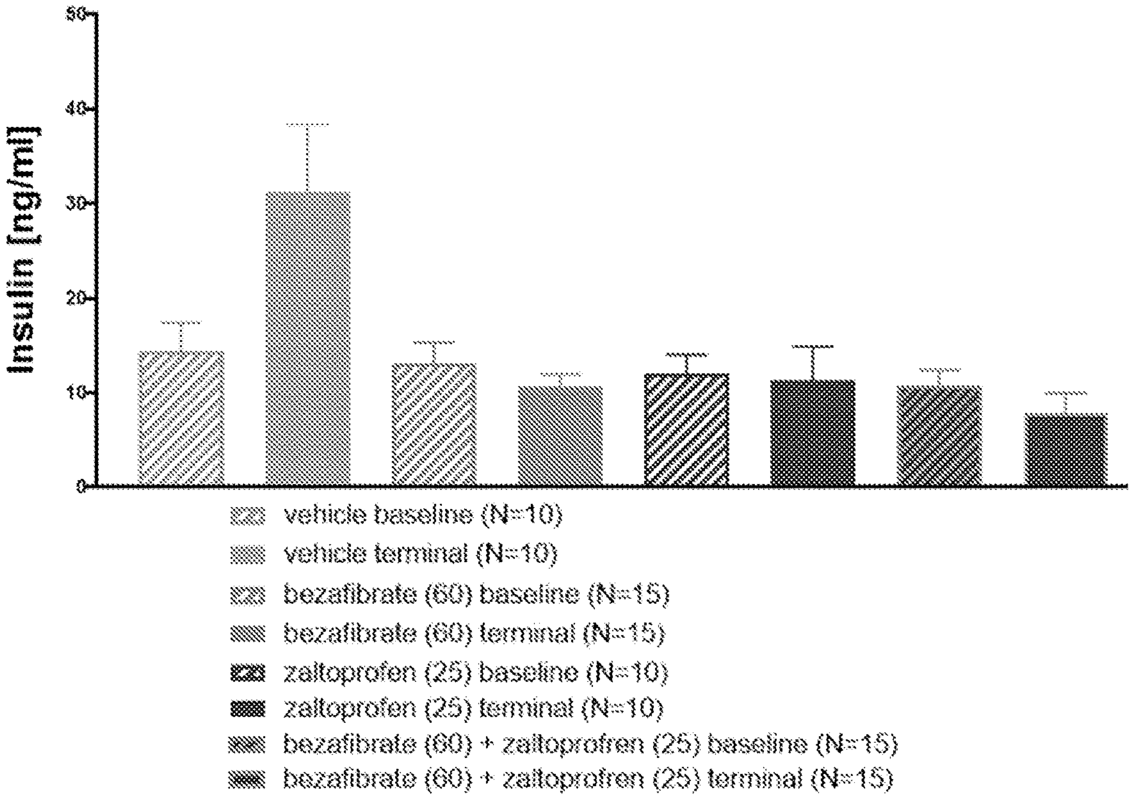

FIG. 77 shows the effects of the combination of bezafibrate (60 mg/kg BW by oral gavage once a day) and zaltoprofen (25 mg/kg BW by oral gavage once a day) on plasma insulin levels in DIO mice.

Figure 78:
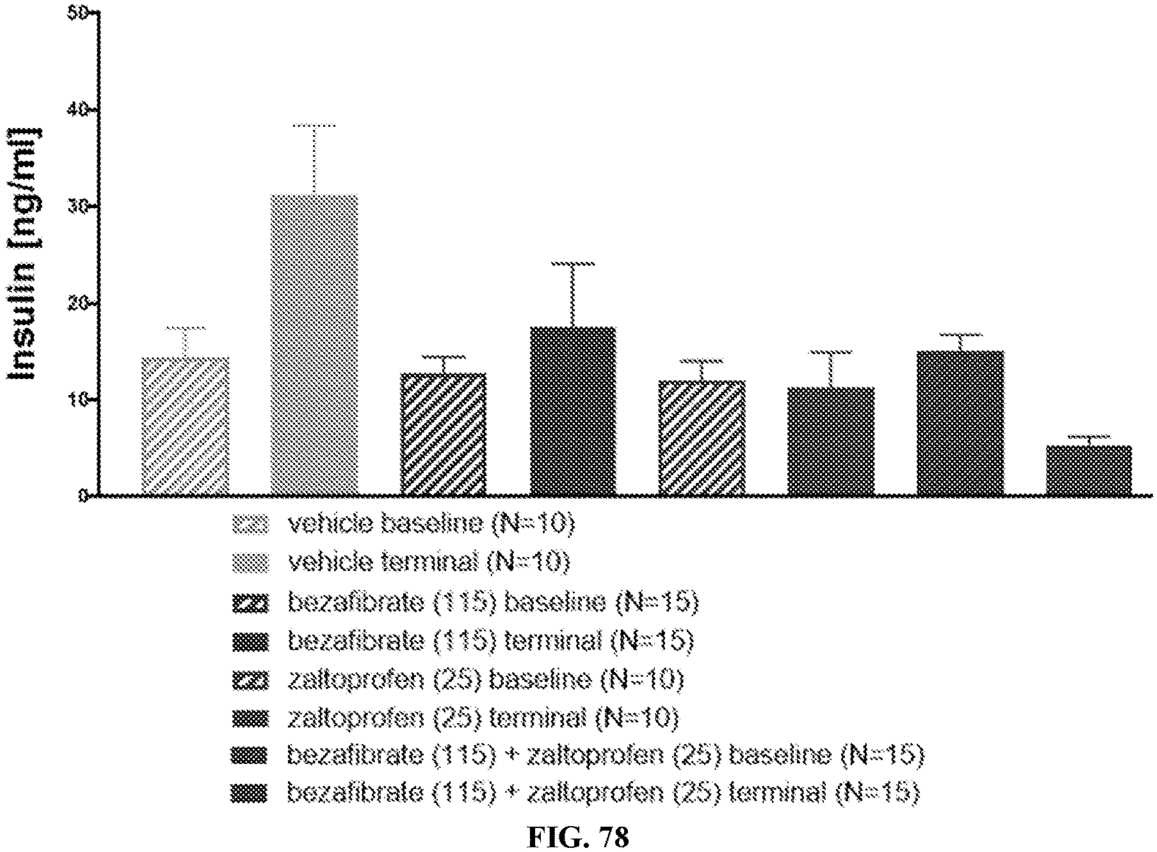

FIG. 78 shows the effects of the combination of bezafibrate (115 mg/kg BW by oral gavage once a day) and zaltoprofen (25 mg/kg BW by oral gavage once a day) on plasma insulin levels in DIO mice.

Figure 79:
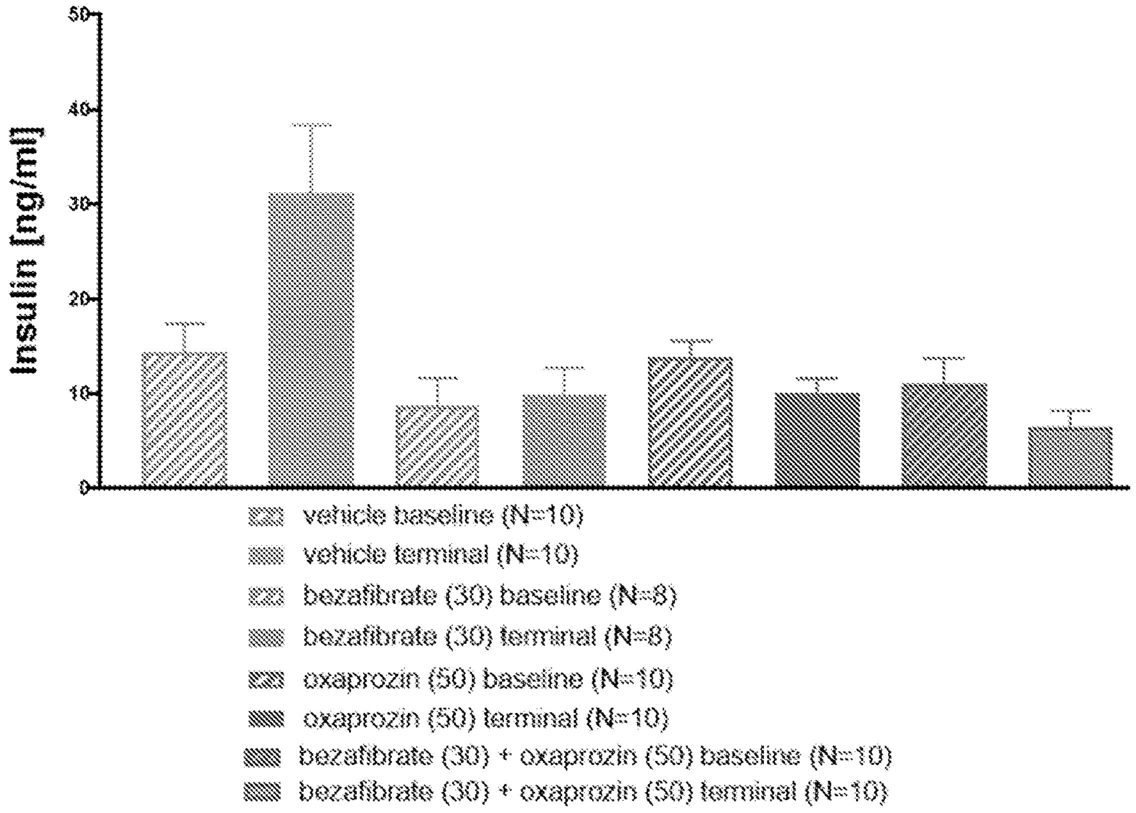

FIG. 79 shows the effects of the combination of bezafibrate (30 mg/kg BW by oral gavage once a day) and oxaprozin (50 mg/kg BW by oral gavage once a day) on plasma insulin levels in DIO mice.

Figure 80:
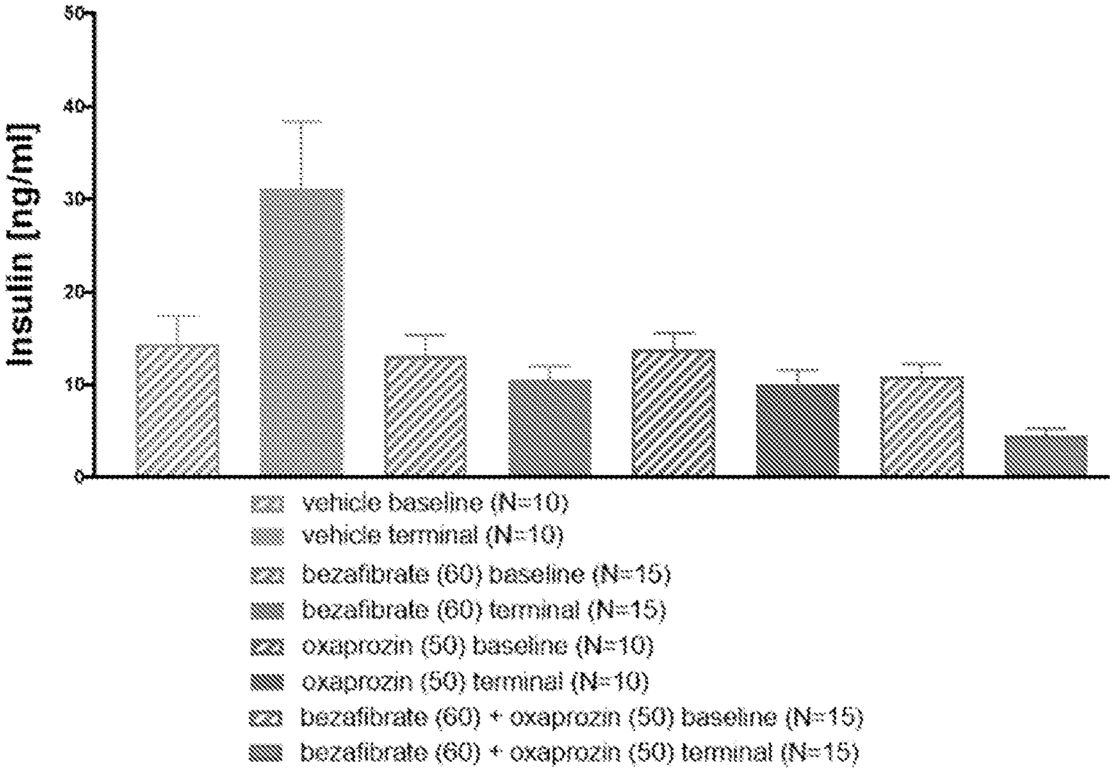

FIG. 80 shows the effects of the combination of bezafibrate (60 mg/kg BW by oral gavage once a day) and oxaprozin (50 mg/kg BW by oral gavage once a day) on plasma insulin levels in DIO mice.

Figure 81:
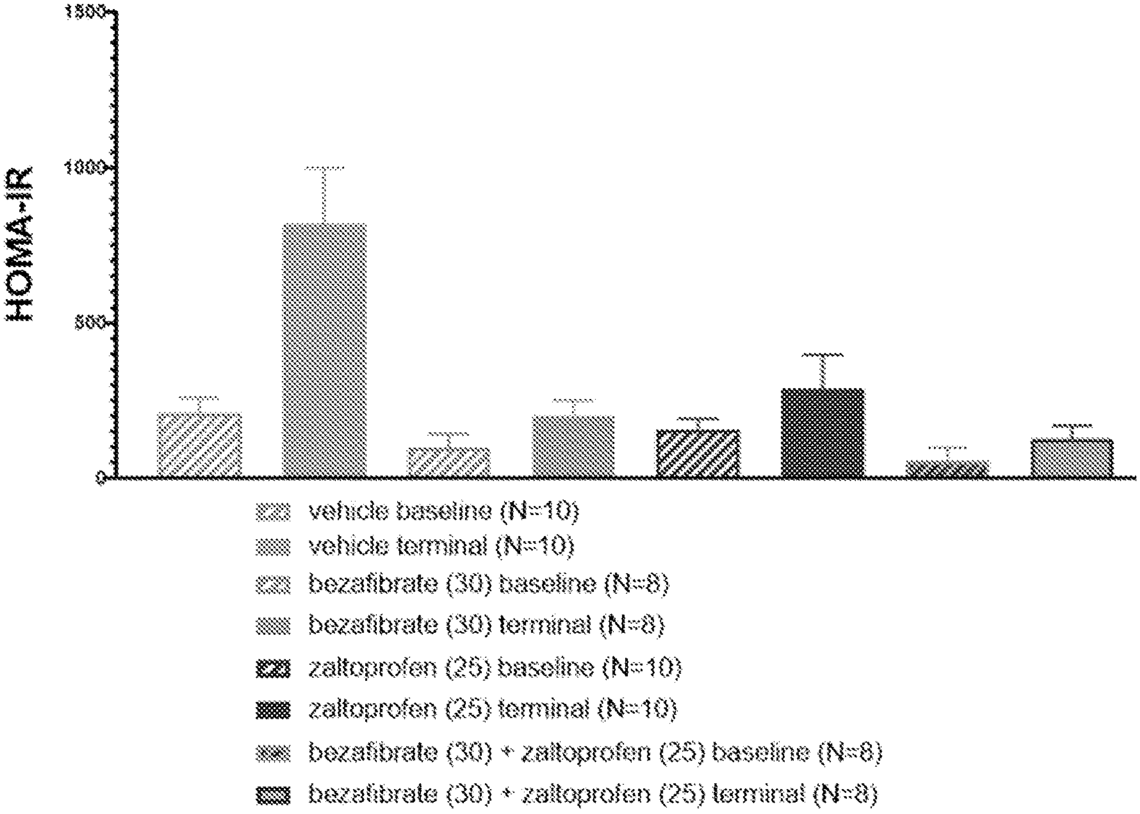

FIG. 81 shows the effects of the combination of bezafibrate (30 mg/kg BW by oral gavage once a day) and zaltoprofen (25 mg/kg BW by oral gavage once a day) on insulin sensitivity in DIO mice, as determined using the homeostasis model assessment of insulin resistance (HOMA-IR). HOMA-IR=(fasting or fed plasma glucose [mM]×fasting or fed plasma insulin [microIU/ml])/22.5.

Figure 82:
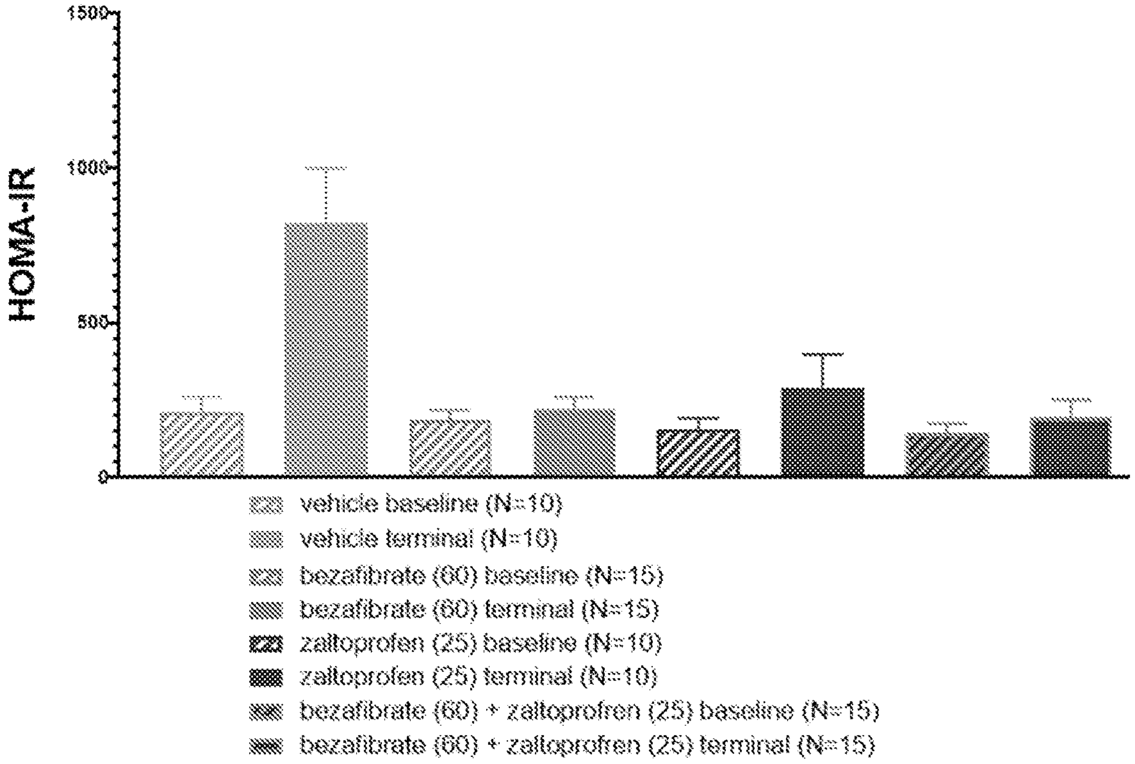

FIG. 82 shows the effects of the combination of bezafibrate (60 mg/kg BW by oral gavage once a day) and zaltoprofen (25 mg/kg BW by oral gavage once a day) on insulin sensitivity in DIO mice, as determined using the homeostasis model assessment of insulin resistance (HOMA-IR).

Figure 83:
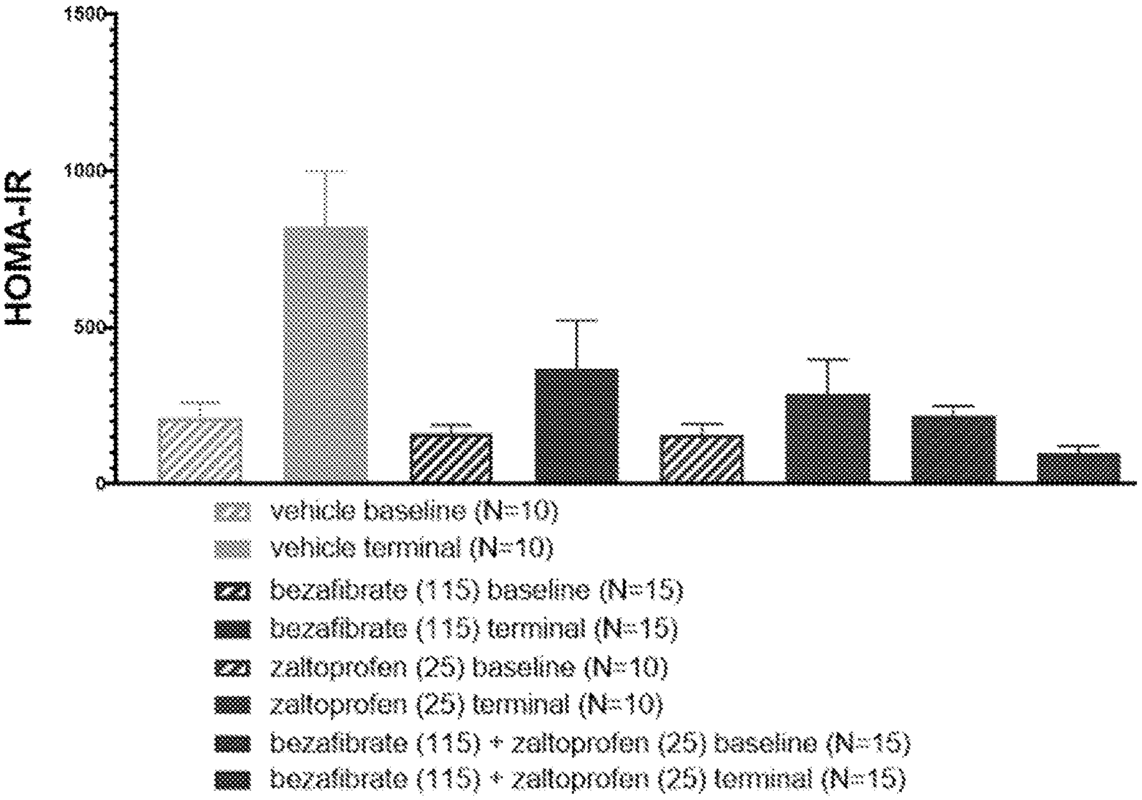

FIG. 83 shows the effects of the combination of bezafibrate (115 mg/kg BW by oral gavage once a day) and zaltoprofen (25 mg/kg BW by oral gavage once a day) on insulin sensitivity in DIO mice, as determined using the homeostasis model assessment of insulin resistance (HOMA-IR).

Figure 84:
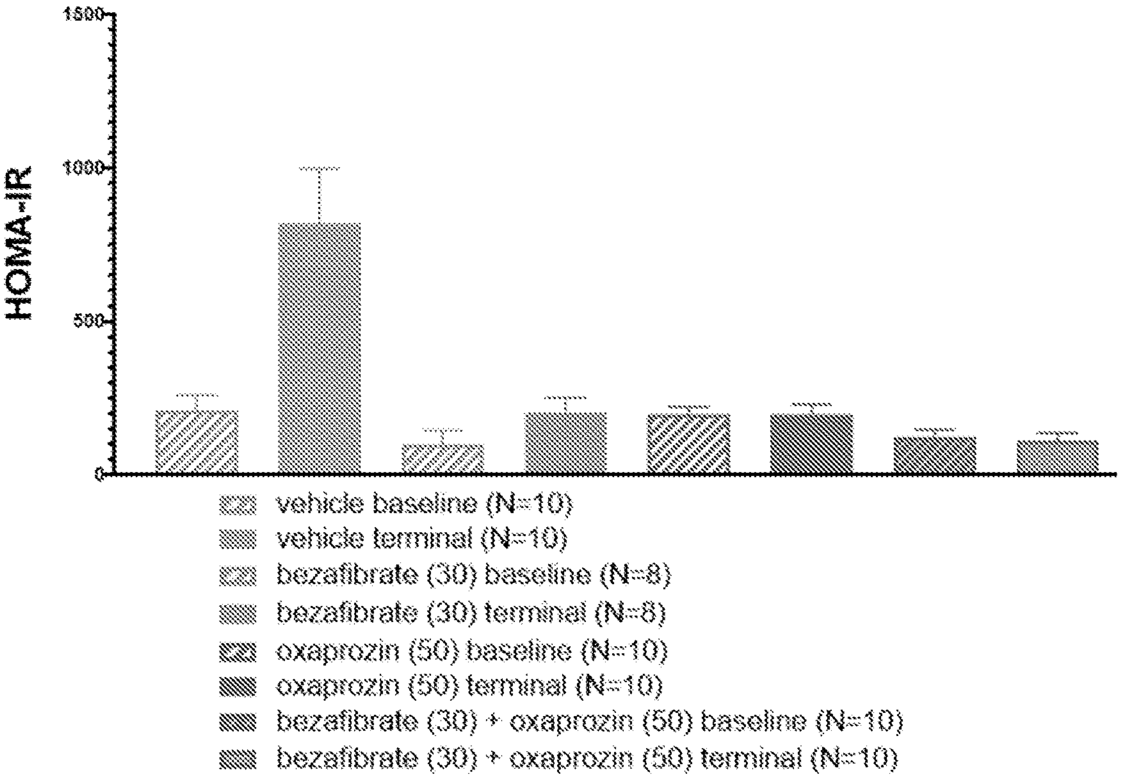

FIG. 84 shows the effects of the combination of bezafibrate (30 mg/kg BW by oral gavage once a day) and oxaprozin (50 mg/kg BW by oral gavage once a day) on insulin sensitivity in DIO mice, as determined using the homeostasis model assessment of insulin resistance (HOMA-IR).

Figure 85:
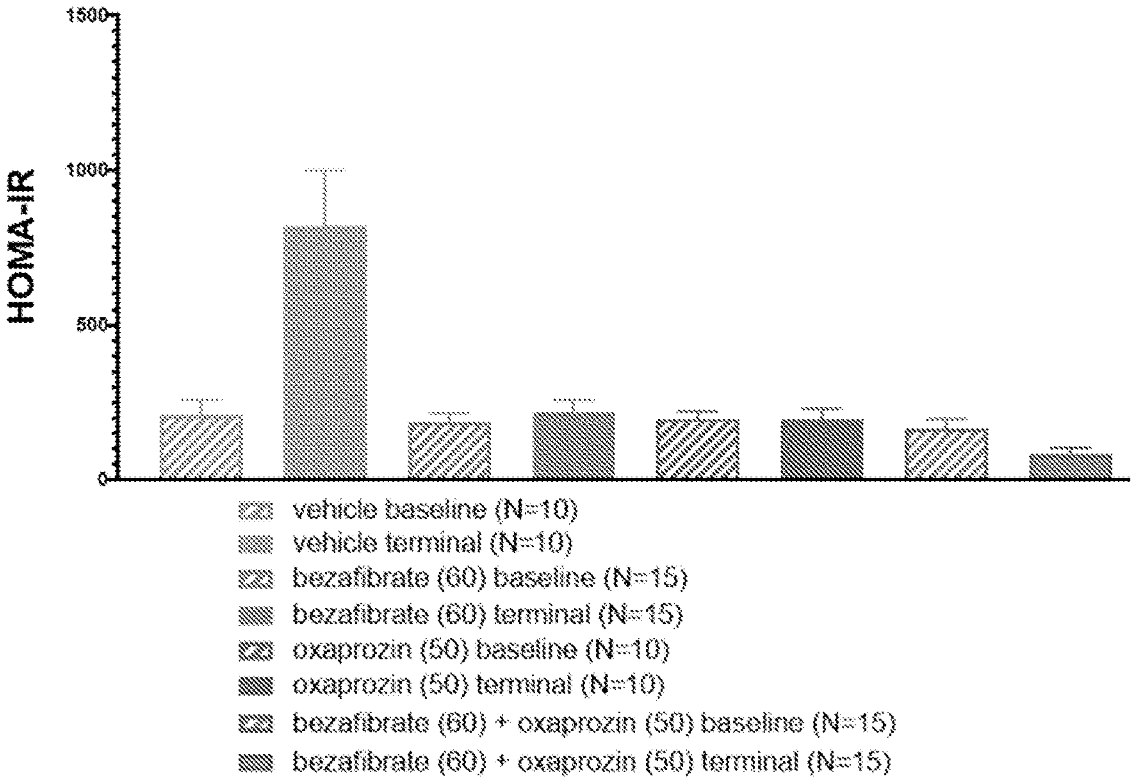

FIG. 85 shows the effects of the combination of bezafibrate (60 mg/kg BW by oral gavage once a day) and oxaprozin (50 mg/kg BW by oral gavage once a day) on insulin sensitivity in DIO mice, as determined using the homeostasis model assessment of insulin resistance (HOMA-IR).

Figure 86:
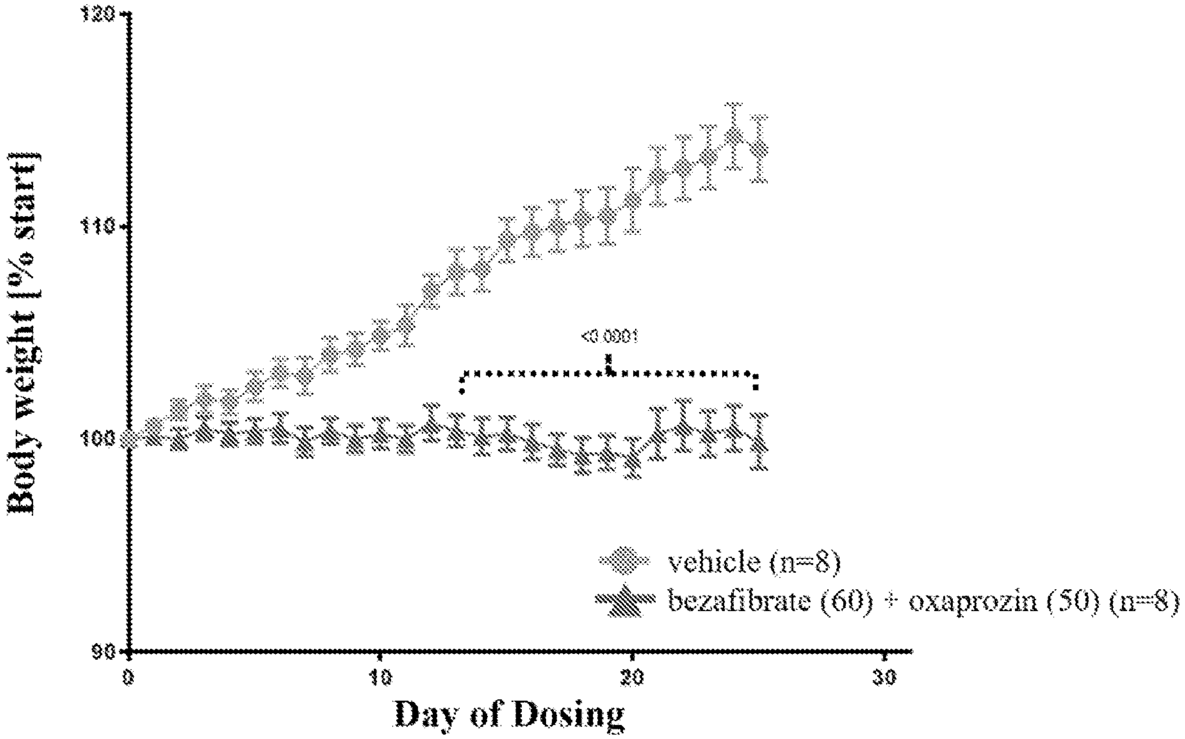

FIG. 86 shows the effects of the combination of bezafibrate (60 mg/kg BW by oral gavage once a day) and oxaprozin (50 mg/kg BW by oral gavage once a day) on body weight in DIO mice.

Figure 87:
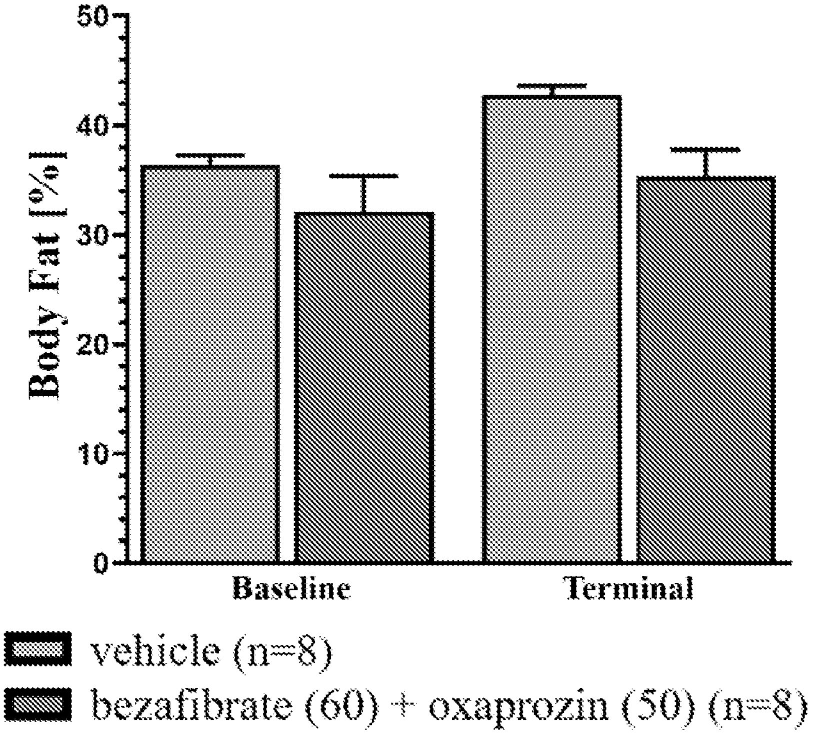

FIG. 87 shows the effects of the combination of bezafibrate (60 mg/kg BW by oral gavage once a day) and oxaprozin (50 mg/kg BW by oral gavage once a day) on body fat (measured by medical resonance imaging, MRI) in DIO mice. $p=0.2316$ at baseline, $p=0.0249$ terminal.

Figure 88:
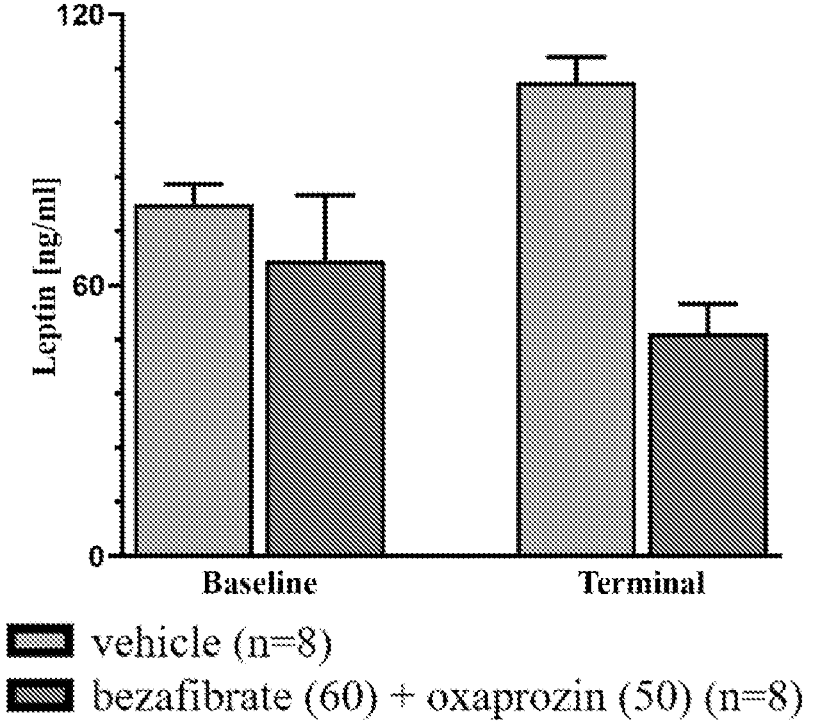

FIG. 88 shows the effects of the combination of bezafibrate (60 mg/kg BW by oral gavage once a day) and oxaprozin (50 mg/kg BW by oral gavage once a day) on plasma leptin levels in DIO mice. $p<0.0001$ terminal.

Figure 89:
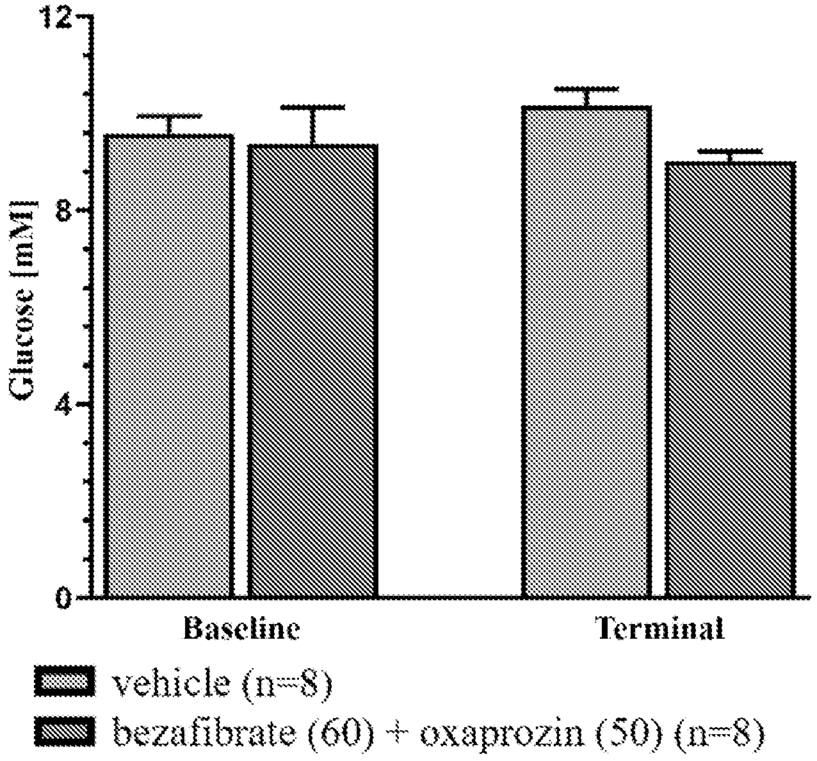

FIG. 89 shows the effects of the combination of bezafibrate (60 mg/kg BW by oral gavage once a day) and oxaprozin (50 mg/kg BW by oral gavage once a day) on blood glucose levels in DIO mice. $p=0.8019$ at baseline, $p=0.0123$ terminal.

Figure 90:
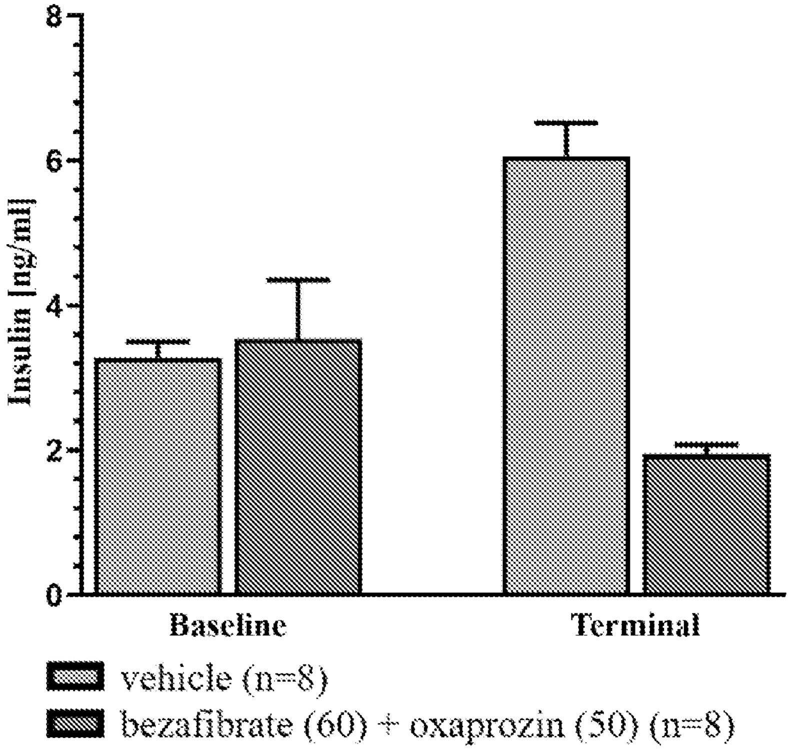

FIG. 90 shows the effects of the combination of bezafibrate (60 mg/kg BW by oral gavage once a day) and oxaprozin (50 mg/kg BW by oral gavage once a day) on plasma insulin levels in DIO mice. $p=0.7627$ at baseline, $p<0.0001$ terminal.

Figure 91:
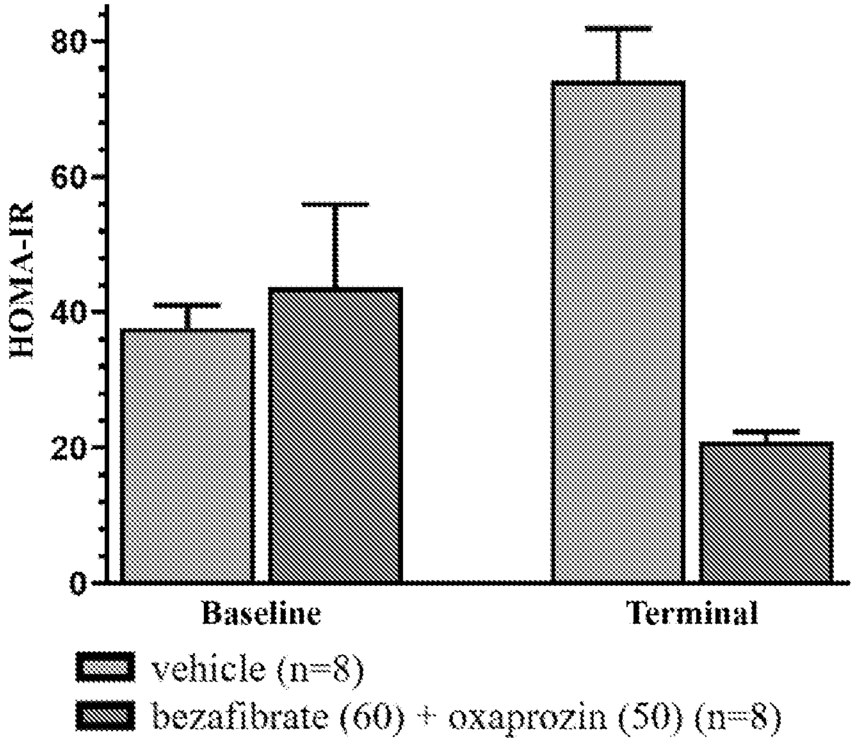

FIG. 91 shows the effects of the combination of bezafibrate (60 mg/kg BW by oral gavage once a day) and oxaprozin (50 mg/kg BW by oral gavage once a day) on insulin sensitivity in DIO mice, as determined using the homeostasis model assessment of insulin resistance (HOMA-IR). $p=0.6413$ at baseline, $p<0.0001$ terminal.

Figure 92:
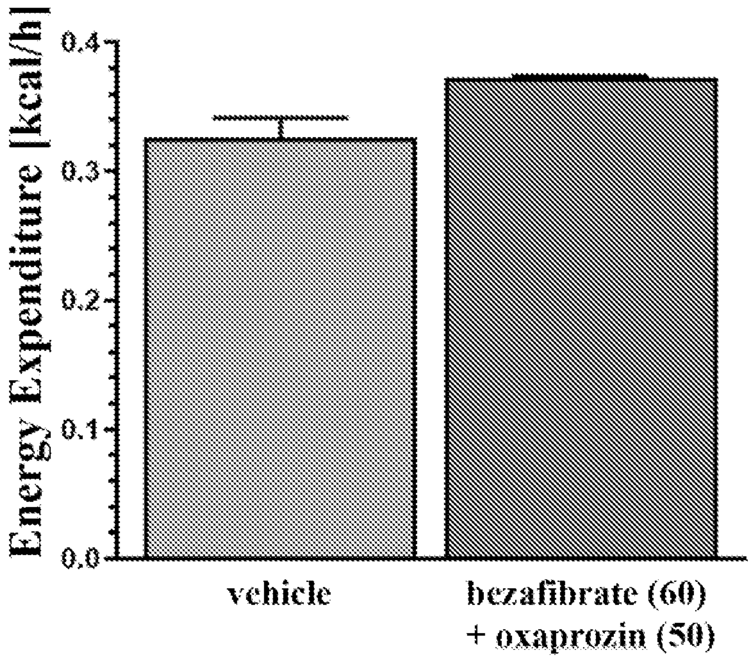

FIG. 92 shows the effects of the combination of bezafibrate (60 mg/kg BW by oral gavage once a day) and oxaprozin (50 mg/kg BW by oral gavage once a day) on energy expenditure [kcal/h] assessed over 24 h post-dosing. $p=0.0075$.

Figure 93:
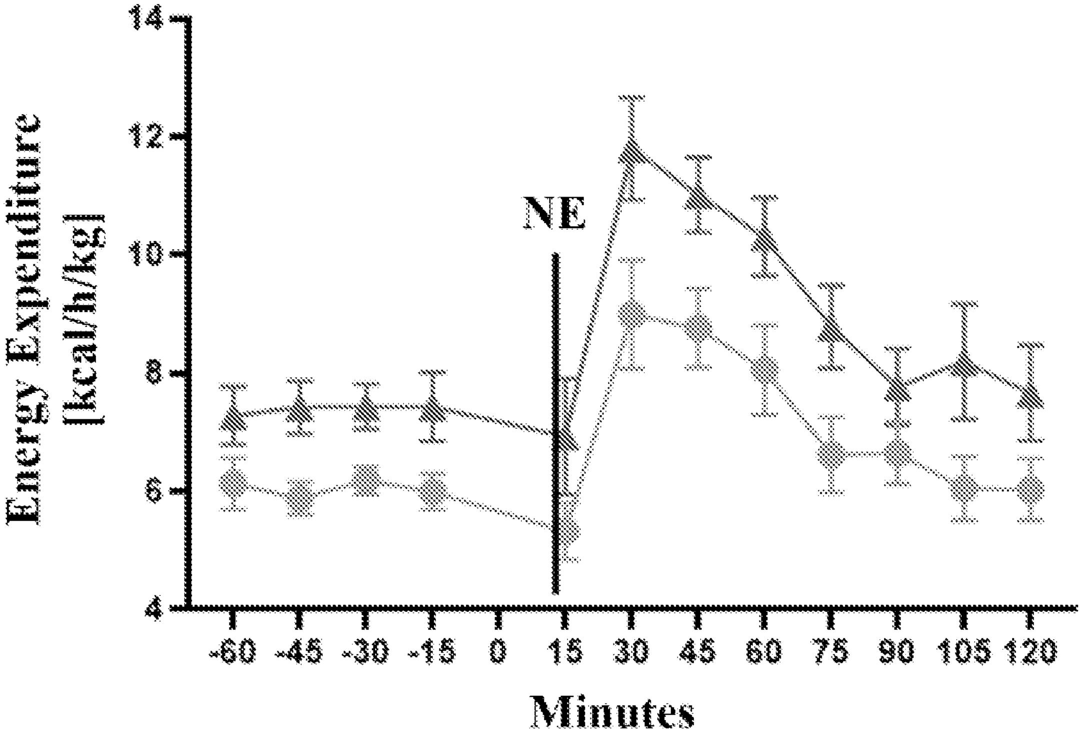

FIG. 93 shows the effects of the combination of bezafibrate (60 mg/kg BW by oral gavage once a day) and oxaprozin (50 mg/kg BW by oral gavage once a day) on energy expenditure [kcal/h] assessed over 1 h pre-norepinephrine injection and 2 h post-norepinephrine injection, post-dosing.

Figure 94:
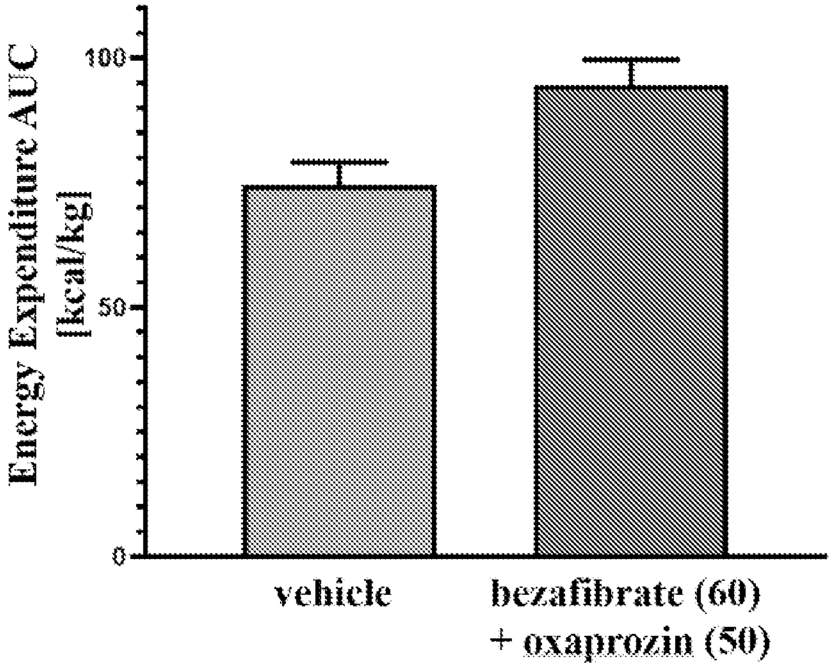

FIG. 94 shows the effects of the combination of bezafibrate (60 mg/kg BW by oral gavage once a day) and oxaprozin (50 mg/kg BW by oral gavage once a day) on energy expenditure [kcal/h] assessed over 2 h post-norepinephrine injection, post-dosing. $p=0.0112$.

DETAILED DESCRIPTION

PCT International Patent Application Nos. PCT/US2009/003217 and PCT/US2012/064366 previously identified the presence of cells in various tissues that are capable of differentiating into brown adipocytes. A population of such cells, referred to as BAT progenitor cells, are found to be present in skeletal muscle. PCT International Patent Application No. PCT/US2015/017392 provided assays that allow identification of agents (e.g., compounds, proteins, biologicals, and the like) that induce the expression of the UCP1 gene, promote the differentiation of BAT progenitor cells into brown adipocytes in vitro, promote the differentiation of BAT progenitor cells to brown adipocytes in vivo, or combinations of these activities.

Provided herein, in some embodiments, is a combination of two or more effective brown adipocyte recruiting agents that can have additive or synergistic effects, and thereby provide greater efficacy than a single agent alone, or reduce the toxicity associated with a single agent by permitting the use of lower doses, and thereby provide for superior product candidates for treating metabolic diseases such as obesity, type 2 diabetes, insulin-resistance, dyslipidemia, and the like. For example, the combination of rosiglitazone and BMP7 results in greater in vitro PPARγ2 and UCP1 expression that either agent alone. Multi-agent combinations, including two-compound combinations that show additive or synergistic activity on metabolic parameters of importance in metabolic disorders were identified by testing candidate brown adipocyte recruiting agents in an animal model of obesity and type 2 diabetes (DIO mice).

The present disclosure provides combinations of agents that promote the differentiation of BAT progenitor cells to brown adipocytes, both in vitro and in vivo. Combinations of effective brown adipocyte recruiters can provide greater efficacy than either compound alone. The combination of rosiglitazone and BMP7 results in greater PPARγ2 and UCP1 expression that either alone.

Accordingly, in some embodiments compositions containing the following can be used to promote the differentiation of BAT progenitor cells into brown adipocytes and/or induce the expression of UCP1, FABP4 (αP2), PPARγ2, mtTFA, PGC-1α, and/or COX IV in BAT progenitor cells in vitro, in vivo, or both: a cyclo-oxygenase inhibitor such as zaltoprofen or oxaprosin, an inhibitor of thromboxane synthetase such as ozagrel, or a pan-PPAR (α, δ, γ) ligand like bezafibrate, in compositions such as bezafibrate in combination with oxaprozin or bezafibrate in combination with zaltoprofen or bezafibrate in combination with ozagrel.

In still other embodiments, additional agents or combinations thereof that can be used to promote the differentiation of BAT progenitor cells into brown adipocytes and/or induce the expression of UCP1 include rosiglitazone or pioglitazone with oxaprozin or with zaltoprofen or ozagrel; Bezafibrate in combination with diflunisal or probenecid or tianeptine or glimepiride; Zaltoprofen in combination with glimepiride or probenecid; Probenecid in combination with tianeptine or ozagrel or diflunisal; or Tianeptine in combination with glimepiride.

In some embodiments, treatment of a subject, including a human subject, with a composition shown here results in an increase in the production of UCP1 mRNA or protein in the subject's skeletal muscle. For example, treatment of subjects with rosiglitazone can, in some embodiments, induce the appearance or differentiation of brown adipocytes in skeletal muscle, enhance expression of the UCP1 gene in existing brown adipocytes in or near skeletal muscle (between myofibers, at the surface of and/or adjacent to skeletal muscle tissue), or both. In some embodiments the appearance or differentiation of brown adipocytes in skeletal muscle can be induced in a subject suffering from a metabolic disease. The brown adipocytes can provide a glucose sink with high mitochondrial and cellular respiration and fatty acid oxidation rates, dissipating energy as heat (uncoupled oxidative phosphorylation). The subject metabolic rate can be enhanced, and a decrease in body weight can be induced. Induction of the appearance or differentiation of brown adipocytes can also yield improvements in insulin sensitivity, blood glucose homeostasis and cardiovascular disease risk factors. Brown adipocytes may further secrete factors that contribute to reaching a healthy energy balance and low body fat levels, increased insulin sensitivity and improved blood glucose homeostasis or cardiovascular health.

Accordingly, in some embodiments the agents disclosed herein, or combinations thereof, can be used for treatment of a subject, including a human subject. In some aspects, these agents may promote the differentiation of BAT progenitor cells into brown adipocytes. In other aspects these agents may induce the expression of UCP1, FABP4 (αP2), PPARγ2, mtTFA, PGC-1α, and/or COX IV in BAT progenitor cells in vitro, in vivo, or both.

In some aspects the treated metabolic disease may be obesity, overweight, type II diabetes, insulin resistance, hyperinsulinemia, hyperglycemia, pre-diabetes, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease.

In other embodiments, compositions may be used to activate isolated BAT progenitor cells that are then used for treatment of a subject, including a human subject.

The assay previously disclosed by PCT International Patent Application No. PCT/US2015/017392 can be used to identify additive or synergistic effects of 2 or more compounds that promote the differentiation of BAT progenitor cells into brown adipocytes. However, as some compounds individually induce almost complete (100%, or close to 100%) brown adipocyte differentiation, it can be challenging to detect significant differences between 2-compound combinations And individual compounds. In vivo studies in mice with obesity, insulin resistance, and impaired glucose tolerance were therefore used to complement the cell culture assays to identify 2-compound combinations producing additive or synergistic effects on any of the metabolic parameters of interest: body weight, body fat content, adipose depot mass, plasma leptin concentration, blood glucose concentration, plasma glucose concentration, plasma insulin concentration, HOMA-IR (Homeostatic Model Assessment of Insulin Resistance), glucose tolerance, or plasma triglyceride concentration.

The combinations tested in animals contain compounds having different known or suspected molecular mechanisms of action. For example, bezafibrate, a fibrate used to treat dyslipidemia, acts through a different molecular target (PPARs) and pathway than oxaprozin. Oxaprozin is an NSAID acting as an inhibitor of cyclooxygenase-1 and −2 (prostaglandin G/H synthase-1 and −2). However, it is likely that oxaprozin acts as described on body weight, body fat, etc., through a molecular target other than cyclooxygenase.

We have discovered that certain bezafibrate-containing compound combinations have in vitro and in vivo activities that suggest that these combinations may be useful for treating a patient that has been diagnosed with or is at risk of having a metabolic disorder. In the case of obesity and diabetes, for example, such administration may reduce the levels of body weight/fat and/or blood glucose.

In one example, we propose that the administration of bezafibrate and oxaprozin to a patient having a metabolic disorder such as obesity or diabetes within 14 days of each other will treat, prevent, or reduce the metabolic disorder.

In another example, the administration of bezafibrate and zaltoprofen to the patient within 14 days of each other will also treat, prevent, or reduce the metabolic disorder.

In another example, the administration of bezafibrate and ozagrel to the patient within 14 days of each other will also treat, prevent, or reduce the metabolic disorder.

The two agents are desirably administered within 10 days of each other, more desirably within seven days of each other, and even more desirably within twenty-four hours of each other, one hour of each other, or even simultaneously (i.e., concomitantly). If desired, either one of the two agents may be administered in low dosage.

In view of this discovery, the aforementioned combinations of drugs can be used in a variety of compositions, methods, and kits, as described herein.

By "treating, reducing, or preventing a metabolic disorder" is meant ameliorating such a condition before or after it has occurred. As compared with an equivalent untreated control, such reduction or degree of prevention is at least 5%, 10%, 20%, 40%, 50%, 60%, 80%, 90°/%, 95%, or 100% as measured by any standard technique.

A patient who is being treated for a metabolic disorder is one who a medical practitioner has diagnosed as having such a condition. Diagnosis may be performed by any suitable means, such as those described herein. A patient in whom the development of diabetes or obesity is being prevented may or may not have received such a diagnosis. One in the art will understand that patients of the disclosure may have been subjected to standard tests or may have been identified, without examination, as one at high risk due to the presence of one or more risk factors, such as family history, obesity, particular ethnicity (e.g., African Americans and Hispanic Americans), gestational diabetes or delivering a baby that weighs more than nine pounds, hypertension, having a pathological condition predisposing to obesity or diabetes, high blood levels of triglycerides, high blood levels of cholesterol, presence of molecular markers (e.g., presence of autoantibodies), and age (over 45 years of age). An individual is considered obese when their weight is 20% (25% in women) or more over the maximum weight desirable for their height. An adult who is more than 100 pounds overweight, is considered to be morbidly obese. Obesity is also defined as a body mass index (BMI) over 30 kg/m2.

By "a metabolic disorder" is meant any pathological condition resulting from an alteration in a patient's metabolism. Such disorders include those resulting from an alteration in glucose homeostasis resulting, for example, in hyperglycemia. According to this disclosure, an alteration in glucose levels is typically an increase in glucose levels by at least 5%, 10%, 20%, 30%, 40%, 50%, 60%, 70%, 80%, 90%, or even 100/relative to such levels in a healthy individual. Metabolic disorders include obesity and diabetes (e.g., diabetes type I, diabetes type II, MODY, and gestational diabetes), dyslipidemia, and endocrine deficiencies of aging.

By "reducing glucose levels" is meant reducing the level of glucose by at least 10%, 20%, 30%, 40%, 50%, 60%, 70%, 80%, 90%, 95%, or 1000% relative to an untreated control. Desirably, glucose levels are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL.

By "patient" is meant any animal (e.g., a human), including horses, dogs, cats, pigs, goats, rabbits, hamsters, monkeys, guinea pigs, rats, mice, lizards, Snakes, sheep, cattle, fish, and birds.

By "an amount sufficient" is meant the amount of a compound, alone or in combination with another therapeutic regimen, required to treat, prevent, or reduce a metabolic disorder such as diabetes in a clinically relevant manner. A sufficient amount of an active compound used to practice the present disclosure for therapeutic treatment of metabolic disorders varies depending upon the manner of administration, the age, body weight, and general health of the mammal or patient. Ultimately, the prescribers will decide the appropriate amount and dosage regimen. Additionally, an effective amount may be an amount of compound in the combination of the disclosure that is safe and efficacious in the treatment of a patient having a metabolic disorder such as diabetes over each agent alone as determined and approved by a regulatory authority (such as the U.S. Food and Drug Administration).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

Compounds useful in the disclosure include those described herein in any of their pharmaceutically acceptable forms, including isomers such as diastereomers and enantiomers, salts, esters, solvates, and polymorphs thereof, as well as racemic mixtures and pure isomers of the compounds described herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, database entries, and other references mentioned herein are incorporated by reference in their entirety. In case of conflict, the present specification, including definitions, will control.

Diagnosis of Metabolic Disorders

The methods and compositions of the present disclosure are useful for treating any patient that has been diagnosed with or is at risk of having a metabolic disorder, such as obesity or diabetes. A patient in whom the development of a metabolic disorder (e.g., obesity or diabetes) is being prevented may or may not have received such a diagnosis. One in the art will understand that patients of the disclosure may have been subjected to standard tests or may have been identified, without examination, as one at high risk due to the presence of one or more risk factors.

An individual is considered obese when their Body Mass Index is 30 $kg/M^2$ or higher. An adult with a BMI>40 is considered to be morbidly obese.

Diagnosis of other metabolic disorders may be performed using any standard method known in the art, such as those described herein. Methods for diagnosing diabetes are described, for example, in U.S. Pat. No. 6,537,806, hereby incorporated by reference. Diabetes may be diagnosed and monitored using, for example, urine tests (urinalysis) that measure glucose and ketone levels (products of the breakdown of fat); tests that measure the levels of glucose in blood; glucose tolerance tests; and assays that detect molecular markers characteristic of a metabolic disorder in a biological sample (e.g., blood, serum, or urine) collected from the mammal (e.g., measurements of Hemoglobin A1c (Hb A1c) levels in the case of diabetes).

Patients may be diagnosed as being at risk or as having diabetes if a random plasma glucose test (taken at any time of the day) indicates a value of 200 mg/dL or more, if a fasting plasma glucose test indicates a value of 126 mg/dL or more (after 8 hours), or if an oral glucose tolerance test (OGTT) indicates a plasma glucose value of 200 mg/dL or more in a blood sample taken two hours after a person has consumed a drink containing 75 grams of glucose dissolved in water. The OGTT measures plasma glucose at timed intervals over a 3-hour period. Desirably, the level of plasma glucose in a diabetic patient that has been treated according to the disclosure ranges between 160 to 60 mg/dL, between 150 to 70 mg/dL, between 140 to 70 mg/dL, between 135 to 80 mg/dL, and preferably between 120 to 80 mg/dL.

Optionally, a hemoglobin A1c (Hb A1c) test, which assesses the average blood glucose levels during the previous two and three months, may be employed. A person without diabetes typically has an HbA1c value that ranges between 4% and 6%. For every 1% increase in Hb A1c, blood glucose level increases by approximately 30 mg/dL and the risk of complications increases. Preferably, the Hb A1c value of a patient being treated according to the present disclosure is reduced to less than 9%, less than 7%, less than 6%, and most preferably to around 5%. Thus, the Hb A1c levels of the patient being treated are preferably lowered by 10%, 20%, 30%, 40%, 50%, or more relative to such levels prior to treatment.

Gestational diabetes is typically diagnosed based on plasma glucose values measured during the OGTT. Since glucose levels are normally lower during pregnancy, the threshold values for the diagnosis of diabetes in pregnancy are lower than in the same person prior to pregnancy. If a woman has two plasma glucose readings that meet or exceed any of the following numbers, she has gestational diabetes: a fasting plasma glucose level of 95 mg/dL, a 1-hour level of 180 mg/dL, a 2-hour level of 155 mg/dL, or a 3-hour level of 140 mg/dL.

The use of any of the above tests or any other tests known in the art may be used to monitor the efficacy of the present treatment. Since the measurements of hemoglobin A1c (HbA1c) levels is an indication of average blood glucose during the previous two to three months, this test may be used to monitor a patient's response to diabetes treatment.

Bezafibrate (2-(4-{2-[(4-chlorobenzoyl)amino]ethyl}phenoxy)-2-methylpropanoic acid) has the following structure:

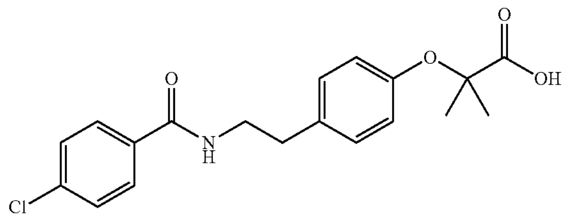 [SMILES: CC(C)(Oc1ccc(CCNC(=O)c2ccc(Cl)cc2)cc1)C(=O)O]

Oxaprozin (3-(4,5-Diphenyloxazol-2-yl)propionic acid) has the following structure:

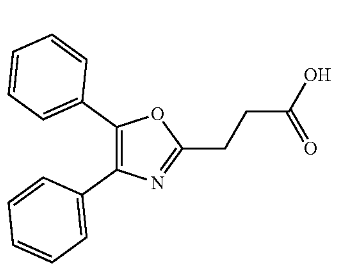 [SMILES: O=C(O)CCc1nc(-c2ccccc2)c(-c2ccccc2)o1]

Zaltoprofen (2-(6-Oxo-5H-benzo[b][1]benzothiepin-3-yl)propanoic acid) has the following structure:

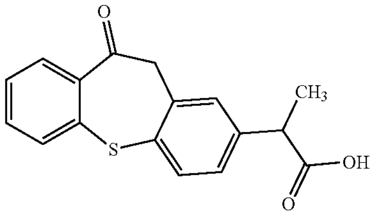 [SMILES: CC(C(=O)O)c1ccc2c(c1)CC(=O)c1ccccc1S2]

Ozagrel ((2E)-3-{4-[(1H-imidazol-1-yl)methyl]phenyl}prop-2-enoic acid) has the following structure:

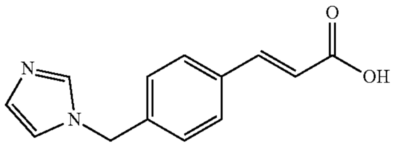 [SMILES: O=C(O)/C=C/c1ccc(Cn2ccnc2)cc1]

EXAMPLES

Aspects of the present teachings may be further understood in light of the following examples, which should not be construed as limiting the scope of the present teachings in any way.

Example 1: Screening of Potential Modulators of Human UCP1 mRNA by Quantification Using TaqMan Real-Time PCR CD34+ cells can be used as a tool to identify agents (small molecule compounds, proteins, biologicals, and the like) that induce the differentiation of these cells into brown adipocytes or modulate the expression of UCP1. For example, an RT-PCR based approach can be used to measure UCP1 mRNA levels which may be affected by certain agents.

This allows the identification of agents that can enhance the differentiation of CD34+ cells into brown adipocytes and/or the expression of UCP1 by enhancing the transcription of the UCP1 gene and/or by stabilizing the UCP1 transcript.

For example, a PPARγ ligand like rosiglitazone can be used to promote the differentiation of CD34+ progenitor cells into brown adipocytes (FIGS. 1-10). Another example is the use of the recombinant protein, human BMP-7 (FIGS. 1-2, 4, 6-9).

A robust method, previously disclosed, was used for detection of CD34+ cell differentiation into brown adipocytes by simultaneously quantifying mRNA species corresponding to the brown adipocyte marker UCP1, the adipocyte marker PPARγ2, and the "housekeeping" gene cyclophilin A which was used as the internal control.

This method permits analysis of a large number of samples to identify agents that enhance the differentiation of CD34+ cells into brown adipocytes. When differentiated into brown adipocytes, CD34+ cells express much higher levels of UCP1 and PPARγ2 mRNA for a given level of cyclophilin A. UCP1 and PPARγ2 mRNA levels normalized to cyclophilin A mRNA levels give an indication of the level of differentiation of the CD34+ cells into brown adipocytes, independent of the total number of cells in the sample.

Quantification of UCP1, PPARγ2 and cyclophilin A mRNA by multiplexed TaqMan real-time PCR was thus used to quantify differentiation of the CD34+ cells into brown adipocytes.

Applicants hypothesized that some previously approved drugs may show activity in recruiting brown adipocytes (inducing the differentiation of brown adipocyte progenitor cells into brown adipocytes), and could thus be of benefit to treat obesity and diabetes. Furthermore, two agents recruiting brown adipocytes through distinct molecular mechanisms could produce effects on brown adipocyte recruitment greater than the individual agents, enhancing in vivo efficacy on parameters of metabolic health.

Materials and Methods

Screening for Brown Adipocyte Recruiters:

UCP1 is the key protein in brown adipocytes responsible for uncoupled respiration and is also highly specific for brown adipocyte differentiation. It is expressed exclusively by fully differentiated brown adipocytes and not by the CD34+ progenitor cells. We used a real-time semi-quantitative RT PCR-based assay for detection of UCP1 expression, in order to screen for brown adipocyte recruiters. The assay is multiplexed for the simultaneous detection of UCP1 (brown fat specific), PPARγ2 (adipocyte-specific and confirmatory for brown differentiation/maturation in the cells as the CD34+ cells do not become white, only brown), and cyclophilin A, for message normalization to cell number. The assay has the added advantage of allowing light microscopic visualization of the distinct morphological changes accompanying differentiation into brown adipocytes. This serves as further confirmation of differentiation. The system responds as predicted to several positive controls (including PPARγ activators like rosiglitazone, pioglitazone, and ciglitazone, and the protein BMP7) with appropriate dose-responsive behavior.

Combinations of compounds can exhibit combinatorial effects. We have shown that with CD34+ cells rosiglitazone and BMP7 both robustly increase the recruitment of brown adipocytes. Given that they may be acting via different mechanisms, they were tested together at their most effective individual concentrations to determine whether they could promote additional recruitment beyond that seen with either compound. In fact, the two together are considerably more effective than either alone (FIGS. 1, 2, 6: Rosiglitazone+BMP7 vs. Rosiglitazone and vs. BMP7), suggesting both that these 2 compounds have different mechanisms and that more generally polypharmacy has the potential to be more effective than individual compounds for brown adipocyte recruitment. The potential to combine active compounds for greater effect was demonstrated. Alternatively, additive (or synergistic) effects with compound combinations may permit the use of lower dosing of one or both drugs, reducing side effects associated with their use.

Cell Culture

Cells were seeded at 10,000 per $cm^2$ (48-well tissue culture, Chemglass #CLS-3500-048), cultured until confluency (1-4 days) at 37° C. in Endothelial cell growth medium-2 (EGM2) (BulletKit growth medium, Lonza #CC-3162) and until differentiation (6-12 more days). After 1-4 days in EGM2 media the cells were incubated with test agents (or positive controls) for 2-3 days (from day −3 or −2 to day 0). Rosiglitazone (1 μM) and rhBMP7 (6.3 nM) were used as reference agents (positive controls). Then (on day 0) the culture media (containing the test agents or positive controls) was removed, and minimal adipogenic medium (MDM) was added and the cells were left to differentiate of 6-12 days. The MDM media is a modification of the adipogenic media described by Rodriguez et al. [21], and contains: DMEM/Ham's F-12 50/50 Mix (3.151 g/l, 17.5 mM D-glucose, 3.651 g/l L-glutamine) (Cellgro #10-090-CV), 5 μg/ml (0.86 μM) insulin, 1 μM dexamethasone, 100 μM 3-isobutyl-1-methylxanthine, 0.2 nM 3,3',5-triiodo-L-thyronine, 10 μg/ml (127 nM) transferrin, and 1% penicillin-streptomycin. Adipocyte scores were determined by light microscopy and defined as the number of cells, on a per well basis, that contain multilocular lipid droplets, at the end of the differentiation of the cells, approximately 6 to 12 days following the end of compound treatment and switch into MDM media.

Quantification of UCP1 and PPARγ2 mRNA by Quantitative Reverse Transcription, Real-Time PCR Total RNA was prepared from cells using PureLink RNA Isolation Kit (Invitrogen #12183-016). Alternatively, cells were simply lyzed by freezing (−80° C.). First strand cDNA were synthesized using the High Capacity cDNA Reverse Transcription kit (Applied Biosystems, Foster City, CA) and random primers.

Quantitative real-time PCR was performed using an Applied Biosystems StepOnePlus™ instrument, TaqMan Gene Expression Master Mix (Applied Biosystems #4369016), and custom TaqMan gene expression probes and primers for human uncoupling protein-1 "UCP1" (GenBank NM_021833) and for human peptidylprolyl isomerase A "cyclophilin A" (GenBank NM_021130). Custom TaqMan Gene Expression reagents were also developed for simultaneous measurement of peroxisome proliferator-activated receptor gamma, transcript variant 2 (PPARγ2) (GenBank NM_015869) in a multiplexed fashion (with UCP1 and cyclophilin A): UCP1 FAM-MGB probe: TCA AGG GGT TGG TAC CTT CC (SEQ ID NO: 1), sense primer: CAC TAA CGA AGG ACC AAC GG (SEQ ID NO: 2), and antisense primer: TTC CAG GAT CCA AGT CGC AA (SEQ ID NO: 3). Cyclophilin A NED-MGB probe: ACT GCC AAG ACT GAG TGG TT (SEQ ID NO: 4), sense primer: CAA ATG CTG GAC CCA ACA CA (SEQ ID NO: 5), and antisense primer: TCA CTT TGC CAA ACA CCA CA (SEQ ID NO: 6). PPARγ2 VIC-MGB probe: TCA CAA GAA ATG ACC ATG GTT G (SEQ ID NO: 7), sense primer: AGC GAT TCC TTC ACT GAT ACA C (SEQ ID NO: 8), and antisense primer: CCA GAA TGG CAT CTC TGT GT (SEQ ID NO: 9).

Cyclophilin A was used as a control to account for any variations due to the efficiency of reverse transcription. Arbitrary units were determined by normalizing target mRNA levels to cyclophilin A mRNA levels (based on Cts).

Pictures for Cell Morphology

Pictures of cells were taken using a hand-held digital camera (Nikon Coolpix 950) and inverted microscope (Nikon TMS) used for cell culture observations; images were optimized using Paint.net version 4.0 functions for Auto-Level Brightness and Contrast.

Results

We incubated CD34+ brown adipocyte progenitors with compounds (at 10 μM) contained in a collection of 1018 FDA approved drugs (FDA Approved Drug Screening Library collection, Selleckchem, Houston, TX). Compounds that were found to be active in the first screen (at 10 μM) were retested at concentrations 1 nM to 50 μM for dose-dependency confirmation.

Using this method the following agents were identified or confirmed to promote the differentiation of brown adipocyte progenitor cells into brown adipocytes, as indicated by expression of UCP1 and PPARγ2, in vitro: an analog of prostaglandin E1 (PGE1) such as Alprostadil, a pan-PPAR (α, δ, γ) ligand like benzofibrate (bezafibrate), a cyclooxygenase inhibitor such as Diflunisal, Zaltoprofen, Indomethacin, Acemethacin, Diclofenac, Mefenamic acid, Niflumic acid, Meclofenamate, or Oxaprozin, an inhibitor of thromboxane synthetase such as Ozagrel, a sulfonylurea such as Glimepiride or Gliquidone, or Probenecid, Tianeptine, Epalrestat (FIGS. 6C-6G, 7-21).

These agents (with the possible exception of bezafibrate and indomethacin) would not have been expected to induce brown adipocyte progenitor cell differentiation, and their biological activity as brown adipocyte-recruiting agents in vitro could not have been predicted based on their respective known molecular targets or approved indications.

Except where otherwise indicated, all organic and inorganic chemicals of analytical or molecular biology grade were purchased from Cayman Chemical (including rosiglitazone, #71742), R&D Systems (including recombinant human BMP7 (rhBMP7), 100 μg/ml, 6.3 μM, #354-BP-010), Sigma Chemical Co. (St Louis, MI), Life Technologies (Grand Island, NY). The FDA Approved Drug Screening Library collection of 1018 FDA approved drugs was purchased from Selleck Chemicals/Selleckchem (Houston, TX).

Using this method the following agents were identified or confirmed to promote the differentiation of BAT progenitor cells into brown adipocytes and/or induce the expression of UCP1, FABP4 (αP2), PPARγ2, mtTFA, PGC-1α, and/or COX IV in BAT progenitor cells in vitro, in vivo, or both: an analog of prostaglandin E1 (PGE1) such as Alprostadil, a pan-PPAR (α, δ, γ) ligand like benzofibrate (bezafibrate), a cyclooxygenase inhibitor such as Diflunisal, Zaltoprofen, Indomethacin, Acemethacin, Diclofenac, Mefenamic acid, Niflumic acid, Meclofenamate, or Oxaprozin, an inhibitor of thromboxane synthetase such as Ozagrel, a sulfonylurea such as Glimepiride or Gliquidone, or Probenecid, Tianeptine, Epalrestat.

Example 2: Quantification of UCP1 Protein by Fluorescence Immunohistochemistry (IHC)

Differentiation of brown adipocyte progenitors into brown adipocytes can be detected through quantification of UCP1 protein by immunohistochemistry.

Culturing and differentiation of CD34+ cells into brown adipocytes were performed using adipogenic differentiation medium lacking (Minimal Differentiation Medium, MDM) or containing 1 μM rosiglitazone (Reference Differentiation Medium, RDM). After 15 days of differentiation cells were fixed with 4% Paraformaldehyde PBS pH 7.4, and incubated with a UCP1 antibody (Abcam ab23841) and Alexafluor 488 goat anti-rabbit antibody to quantify relative UCP1 levels (green) according to standard protocols. Prior to fixation of cells, nuclei were labeled with 5 μM DAPI (blue) for 10 minutes. Each treatment condition was evaluated in triplicate in a 96-well plate corresponding to approximately 360-480 cells for each data point in total. The InCell 1000 Developer Toolbox software was used to develop an automated cell detection script to measure UCP1 signal intensity, using the nuclei and cytoplasm detection algorithms. As a readout, total intensity of UCP1 signal within the cell was used, normalized to cell number.

In some embodiments, agents or combinations thereof that were identified using this technique include Famotidine, Tiapride hydrochloride, Guanfacine hydrochloride, Reserpine, Minoxidil, Spiperone, Diflunisal, Syrosingopine, Probenecid, Metformin, Thiethylperazine, Colchicine, and Felodipine.

Example 3: Detection of Brown Adipocyte Differentiation Using BODIPY

BODIPY fluorescent dye-labeled neutral lipids become incorporated in cytoplasmic lipid droplets allowing analysis of cellular fatty acid uptake and adipocyte differentiation by fluorescent cellular imaging. Cells are incubated with C1-BODIPY® 500/510 C12 (Molecular Probes #D-3823) for 3 to 6 hours before imaging on a microplate-based high-throughput, high-content, brightfield and fluorescence cellular imager and analyzer (Cyntellect Celigo® or GE Healthcare IN Cell Analyzer).

Example 4: The Combination of Bezafibrate and Oxaprozin Induces Body Weight Loss, an Increase in Insulin Sensitivity, and Improvement in Blood Glucose Homeostasis in a Mouse Model of Obesity and Diabetes An agent that promotes the differentiation of brown adipocyte progenitor cells into brown adipocytes, i.e., an agent that recruits brown adipocytes or brown adipose tissue in vivo could be expected to cause improvement of any of the following parameters of metabolic health in obese individuals or animals: decreases in body weight, body fat content, plasma levels of leptin, glucose and insulin, and index of insulin resistance HOMA-IR (HOMA-IR=(plasma insulin [microIU/ml]×plasma glucose [mM])/22.5).

We investigated the effects of agents that were found to recruit brown adipocytes in vitro on parameters of metabolic health in obese, pre-diabetic mice. In order to uncover possible combinatorial effects between several compounds, we also investigated the effects of combinations of two agents that recruit brown adipocytes in vitro and are known, or believed to, affect different molecular targets and intracellular signaling pathways.

Materials and Methods

Animal Studies

Obesity and insulin resistance, an early stage in the development of type 2 diabetes (or pre-diabetes), was induced in C57Bl/6 mice by feeding the mice with a high fat diet (Research diet, Cat #D12492, 60/a fat kcal) for 12 weeks starting at 6 weeks of age. The mice were maintained at 22-23° C. with abundant bedding material, maintaining the animals in an environmental temperature close to their thermoneutrality, starting 2 weeks prior to the dosing period and for the full dosing period with a 12 h/12 h light/dark cycle.

Mice were dosed once per day by oral gavage (200 μl per mouse), first for 3 days with the vehicle (PBS+0.5% CMC+0.1% Tween-80) as acclimation for running into the study, then with either vehicle alone or testing material dissolved in the vehicle for 28 to 55 days (4 to 8 weeks).

Body weight was recorded every 3 days, body composition (fat and lean mass with EchoMRI) was assessed at the end of the study (University of Cincinnati Mouse Metabolic Phenotyping Center), blood glucose level (measured with a glucometer) was monitored 3-5 days before (baseline) and at the end of the dosing period.

At the end of the dosing period, animals were fasted for 6 hours and euthanized by $CO_2$, blood was collected, and plasma was isolated and saved at −20° C. Plasma glucose, insulin and leptin levels were assessed 3-5 days before (baseline) and at the end of the dosing period (mice were fasted for 6 hours before all plasma collection) (University of Cincinnati Mouse Metabolic Phenotyping Center). Insulin sensitivity was determined using the homeostasis model assessment of insulin resistance (HOMA-IR) [38]. HOMA-IR=(plasma insulin [microIU/ml]×plasma glucose [mM])/22.5.

The mice were maintained on a high fat diet (60% calories from fat) throughout the study. An overnight fast was performed the last night of the study in preparation for glucose tolerance testing.

Animal Study with Indirect Calorimetry (Bezafibrate (60)+Oxaprozin (50))

Diet-induced obesity mice: C57Bl/6 males mice were fed with a high fat diet (Research diet, Cat #D12492, 60% fat kcal) for 12 weeks starting at 6 weeks of age. The mice were maintained at 22-23° C. with abundant bedding material, maintaining the animals in an environmental temperature close to their thermoneutrality, starting 2 weeks prior to the dosing period and for the full dosing period with a 12 h/12 h light/dark cycle.

Mice were dosed once per day by oral gavage (200 μl per mouse) with either vehicle alone (PBS+0.5% CMC+0.1% Tween-80) or the combination of bezafibrate at 60 mg/kg+oxaprozin at 50 mg/kg dissolved in the vehicle for 24 days.

Body weight was recorded daily, body composition (fat and lean mass with EchoMRI) was assessed at baseline (before dosing) and at the end of the dosing period (University of Michigan Mouse Metabolic Phenotyping Center).

At the end of the dosing period, animals were fasted for 6 hours and euthanized by $CO_2$, blood was collected, and plasma was isolated and saved at −20° C. Plasma glucose, insulin and leptin levels were assessed at baseline and at the end of the dosing period (mice were fasted for 6 hours before all plasma collection) (University of Michigan Mouse Metabolic Phenotyping Center).

After 24 days of dosing the mice were transferred to calorimetry chambers (1 mouse per cage) and maintained 3 days at 30° C., a temperature close to mouse thermoneutrality. During the 3 days in the calorimetry chambers (TSE Systems Phenomaster) the following parameters were measured: energy expenditure by indirect calorimetry (using oxygen consumption rate (VO2), carbon dioxide production (VCO2), respiratory quotient (RQ)), food intake, locomotor activity, ambulatory activity and distance traveled (beam breaks).

The first day in the calorimetric chamber was used as acclimation period (parameters measured were not used in the data analysis). The values obtained during the second day (over 24 h) in the calorimetric chamber were used as non-stimulated/resting values. On the third day in the calorimetric chamber we measured whole-body non-shivering thermogenesis of the mice, a measure of whole-body brown adipose tissue capacity [39] using a single injection of 1 mg/kg norepinephrine.

Statistical Analysis

Data from cell culture studies are expressed as mean f SEM. Significances were evaluated using the paired or unpaired Student's t-test using online GraphPad QuickCalcs t test calculator (GraphPad Software, San Diego, CA). Significances were set at p<00.05.

Data from in vivo mouse studies are presented as mean f SEM. Significances were evaluated using the paired or unpaired Student's t-test, 2-way ANOVA or 1-way ANOVA with Bonferroni's or Dunnett's multiple comparison test using GraphPad Prism version 7 or 8 (GraphPad Software, San Diego, CA). Significances were set at p<0.05, with *: p<0.05 vs. Vehicle, : p<0.01 vs. Vehicle, *: p<0.001 vs. Vehicle.

Results

In the first study reported here we tested the effects of bezafibrate (60 mg/kg), oxaprozin (50 mg/kg) and the combination of bezafibrate (60)+oxaprozin (50) in DIO mice over 56 days of dosing on parameters of metabolic health. These data were generated using bezafibrate at approximately half of the recommended dosing level in humans being treated for hyperlipidemia, allometrically scaled for mice according to current FDA guidance. Oxaprozin was used at approximately one-quarter of the scaled recommended human dose in our animal studies.

Treatment of DIO mice with bezafibrate (60 mg/kg) or with oxaprozin (50 mg/kg) over 56 days, compared to treatment with vehicle, induced significant decreases in body weight (FIG. 60), body fat mass (FIG. 65), plasma leptin (FIG. 70), glycemia (FIG. 75), plasma insulin (FIG. 80) and insulin resistance index (HOMA-IR) (FIG. 85).

In addition, we found that the combination of bezafibrate (60 mg/kg)+oxaprozin (50 mg/kg) caused further decreases in all these metabolic parameters. In fact, the weight loss inducing effect of the combination (FIG. 60) as well as the effect on body fat (FIG. 65) were statistically synergistic (i.e., greater than additive).

We found that bezafibrate+oxaprozin produced highly significant reduction in body weight in DIO mice over 56 days (p=2.6×10−10). The observed effect was synergistic (greater than the sum of the effects of the 2 individual agents vs vehicle (p=0.043). P-values for all figures from this 56 day study of bezafibrate (60)+oxaprozin were determined based on two-sided Z-tests with standard errors estimated via the bootstrap method. To assess synergistic effects, we tested whether the percent change from baseline with the combination is higher than the sum of the percent changes from baseline of the 2 individual drugs. A log-transformation was used for Z-tests on group differences for all end of study measurements. These data were generated using bezafibrate at approximately half of the recommended dosing level in humans being treated for hyperlipidemia, allometrically scaled for mice according to current FDA guidance. Oxaprozin was used at approximately one-quarter of the scaled recommended human dose in our animal studies.

Bezafibrate is known to lower plasma levels of triglycerides and LDL cholesterol through activation of PPARα in the liver, and is used to treat dyslipidemia and increased cardiovascular risk. Oxaprozin is a non-steroid agent anti-inflammatory (NSAID) agent that inhibits cyclooxygenases 1 and 2, and is used to treat rheumatoid arthritis.

Based on this, the synergistic effects of the combination of bezafibrate and oxaprozin on body weight, body fat content and plasma leptin levels could not have been anticipated based on the known effects of these individual agents. It is possible that the known molecular targets of these two agents mediate the brown adipocyte-recruiting (and metabolic) effects of these agents. Alternatively, it is possible that one or both of these agents affect brown adipocyte recruitment and metabolic health through other molecular targets.

Using this general method, the following, comprising combinations of certain existing drugs, were identified or confirmed to induce body weight loss, an increase in insulin sensitivity, and improvement in blood glucose homeostasis in a mouse model of obesity and diabetes: Bezafibrate in combination with oxaprozin or zaltoprofen or ozagrel or diflunisal or probenecid or tianeptine or glimepiride, Rosiglitazone or Pioglitazone in combination with oxaprozin or zaltoprofen or ozagrel, Zaltoprofen in combination with glimepiride or probenecid, Probenecid in combination with tianeptine or ozagrel or diflunisal, and Tianeptine in combination with glimepiride.

In a second study the effects of the combination of bezafibrate (60 mg/kg)+oxaprozin (50 mg/kg) was investigated in DIO mice over 24 days of dosing on parameters of metabolic health and energy expenditure (metabolic rate) at rest and after maximal sympathetic stimulation with norepinephrine. The aim of this study was to assess the energy expenditure and whole-body thermogenic capacity of the mice after 24 days of dosing with bezafibrate (60)+oxaprozin (50). The purpose was to assess whether the mice treated with bezafibrate (60)+oxaprozin (50) showed evidence of increased brown adipose mass (and capacity) compared to the mice given the vehicle.

Treatment of DIO mice with the combination of bezafibrate (60 mg/kg)+oxaprozin (50 mg/kg) over 24 days, compared to treatment with vehicle, induced significant decreases in body weight (FIG. 86), body fat mass (FIG. 87), plasma leptin (FIG. 88), glycemia (FIG. 89), plasma insulin (FIG. 90) and insulin resistance index (HOMA-IR) (FIG. 91).

In addition, energy expenditure assessment by indirect calorimetry showed that the mice treated with the combination of bezafibrate (60)+oxaprozin (50) had significantly higher energy expenditure (over 24 h, unstimulated, FIG. 92).

Furthermore, the thermogenic (energy expenditure) response to the norepinephrine injection was significantly higher in the mice treated with the combination of bezafibrate (60)+oxaprozin (50) vs. the mice treated with vehicle (FIGS. 93-94), demonstrating increased thermogenic capacity, i.e., capacity/mass of brown adipose tissue in the animal.

There was no significant difference between the groups of mice in food intake, locomotor activity, ambulatory activity and distance traveled.

These data clearly demonstrate that, in DIO mice, the combination of bezafibrate (60)+oxaprozin (50) induces a recruitment, an increase, in thermogenic brown/brite/beige adipose tissue, which results in enhanced energy expenditure (metabolic rate) and an improvement in parameters of metabolic health (decreases in body weight, fat mass, plasma leptin, glucose and insulin levels, and index of insulin resistance HOMA-IR).

The section headings and subheadings used in this specification are for organizational purposes only and are not to be construed as limiting the subject matter described in any way. Further, while the present teachings are described in conjunction with various embodiments, it is not intended that the present teachings be limited to such embodiments. On the contrary, the present teachings encompass various alternatives, modifications, and equivalents as will be appreciated by those of skill in the art.

Other Embodiments

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present disclosure provides among other things novel compositions capable of recruiting brown adipocytes in vitro and in vivo. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Incorporation by Reference

All publications, patents and patent applications referenced in this specification are incorporated herein by reference in their entirety for all purposes to the same extent as if each individual publication, patent or patent application were specifically indicated to be so incorporated by reference.

REFERENCES

[1] M. Klingenspor, Cold-induced recruitment of brown adipose tissue thermogenesis, Exp Physiol. 88 (2003) 141-148.

[2] B. Cannon, J. Nedergaard, The biochemistry of an inefficient tissue: brown adipose tissue, Essays Biochem. 20 (1985) 110-164.

[3] N. J. Rothwell, M. J. Stock, A role for brown adipose tissue in diet-induced thermogenesis, Nature. 281 (1979) 31-35.

[4] B. B. Lowell, V. S-Susulic, A. Hamann, J. A. Lawitts, J. Himms-Hagen, B. B. Boyer, L. P. Kozak, J. S. Flier, Development of obesity in transgenic mice after genetic ablation of brown adipose tissue, Nature 366 (1993) 740-742.

[5] H. M. Feldmann, V. Golozoubova, B. C. M. Cannon, J. Nedergaard, UCP1 ablation induces obesity and abolishes diet-induced thermogenesis in mice exempt from thermal stress by living at thermoneutrality, Cell Metab. 9 (2009) 203-209.

[6] J. Kopecky, G. Clarke, S. Enerback, B. Spiegelman, L. P. Kozak, Expression of the mitochondrial uncoupling protein gene from the αP2 gene promoter prevents genetic obesity, J Clin Invest. 96 (1995).

[7] K. Tsukiyama-Kohara, F. Poulin, M. Kohara, CT. DeMaria, A. Cheng, Z. Wu, A. C. Gingras, A. Katsume, M. Elchebly, B. M. Spiegelman, M. E. Harper, M. L. Tremblay, N. Sonenberg, Adipose tissue reduction in mice lacking the translational inhibitor 4E-BP1, Nature Medicine 7 (2001) 1128-1132.

[8] K. Almind, M. Manieri, W. I. Sivitz, S. Cinti, CR. Kahn, Ectopic brown adipose tissue in muscle provides a mechanism for differences in risk of metabolic syndrome in mice, Proc Natl Acad Sci USA. (2007).

[9] M. Del Mar Gonzalez-Barroso, D. Ricquier, A. M. Cassard-Doulcier, The human uncoupling protein-1 gene (UCP1): present status and perspectives in obesity research, Obes Rev. 1 (2000) 61-72.

[10] B. Cannon, J. Nedergaard, Brown adipose tissue: function and physiological significance, Physiol Rev. 84 (2004) 277-359.

[11] W. D. van Marken Lichtenbelt, J. W. Vanhommerig, N. M. Smulders, J. M. Drossaerts, G. J. Kemerink, N. D. Bouvy, P. Schrauwen, G. J. Teule, Cold-activated brown adipose tissue in healthy men, N Engl J Med. 360 (2009) 1500-1508.

[12] A. M. Cypess, S. Lehman, G. Williams, I. Tal, D. Rodman, A. B. Goldfine, F. C Kuo, E. L. Palmer, Y. H. Tseng, A. Doria, G. M. Kolodny, CR. Kahn, Identification and importance of brown adipose tissue in adult humans, N Engl J Med. 360 (2009) 1509-1517.

[13] K. A. Virtanen, M. E. Lidell, J. Orava, M. Heglind, R. Westergren, T. Niemi, M. Taittonen, J. Laine, N.J. Savisto, S. Enerback, P. Nuutila, Functional brown adipose tissue in healthy adults, N Engl J Med. 360 (2009) 1518-1525.

[14] H. L. Garstka, W. E. Schmitt, J. Schultz, B. Sogl, B. Silakowski, A. Perez-Martos, J. Montoya, R. J. Wiesner, Import of mitochondrial transcription factor A (TFAM) into rat liver mitochondria stimulates transcription of mitochondrial DNA, Nucleic Acids Res. 31 (2003) 5039-5047.

[15] Z. Wu, P. Puigserver, B. M. Spiegelman, Transcriptional activation of adipogenesis, Curr Opin Cell Biol. 11 (1999) 689-694.

[17] L. A. Foellmi-Adams, B. M. Wyse, D. Herron, J. Nedergaard, R. F. Kletzien, Induction of uncoupling protein in brown adipose tissue. Synergy between norepinephrine and pioglitazone, an insulin-sensitizing agent, Biochem Pharmacol. 52 (1996) 693-701.

[18] M. Mensink, M. K. Hesselink, A. P. Russell, G. Schaart, J. P. SeIs, P. Schrauwen, Improved skeletal muscle oxidative enzyme activity and restoration of PGC-I alpha and PPAR beta/delta gene expression upon rosiglitazone treatment in obese patients with type 2 diabetes mellitus, Int J Obes (Lond). 31 (2007) 1302-1310.

[19] L. Lehr, K. Canola, C. Asensio, M. Jimenez, F. Kuehne, J. P. Giacobino, P. Muzzin, The control of UCP1 is dissociated from that of PGC-I alpha or of mitochondriogenesis as revealed by a study using beta-less mouse brown adipocytes in culture, FEBS Lett. 580 (2006) 4661-4666.

[20] O. Champigny, B. R. Holloway, D. Ricquier, Regulation of UCP gene expression in brown adipocytes differentiated in primary culture. Effects of a new beta-adrenoceptor agonist, Mol Cell Endocrinol. 86 (1992) 73-82.

[24] M. Jimenez, C. Yvon, L. Lehr, B. Leger, P. Keller, A. Russell, F. Kuhne, P. Flandin, J. P. Giacobino, P. Muzzin, Expression of uncoupling protein-3 in subsarcolemmal and intermyofibrillar mitochondria of various mouse muscle types and its modulation by fasting, Eur J Biochem. 269 (2002) 2878-2884.

[26] Tseng Y H, Kokkotou E, Schulz T J, Huang T L, Winnay J N, Taniguchi C M, Tran T T, Suzuki R, Espinoza D O, Yamamoto Y, Ahrens M J, Dudley A T, Norris A W, Kulkarni R N, Kahn C R. New role of bone morphogenetic protein 7 in brown adipogenesis and energy expenditure. Nature. 2008 Aug. 21; 454(7207): 1000-4. PubMed PMID: 18719589; PubMed Central PMCID: PMC2745972.

[27] Zhang H, Schulz T J, Espinoza D O, Huang T L, Emanuelli B, Kristiansen K, Tseng Y H. Cross talk between insulin and bone morphogenetic protein signaling systems in brown adipogenesis. Mol Cell Biol. 2010 September; 30(17):4224-33. Epub 2010 Jun. 28. PubMed PMID: 20584981; PubMed Central PMCID: PMC2937545.

[28] Schulz T J, Huang T L, Tran T T, Zhang H, Townsend K L, Shadrach J L, Cerletti M, McDougall L E, Giorgadze N, Tchkonia T, Schrier D, Falb D, Kirkland J L, Wagers A J, Tseng Y H. Identification of inducible brown adipocyte progenitors residing in skeletal muscle and white fat. Proc Natl Acad Sci USA. 2011 Jan. 4; 108(1):143-8. Epub 2010 Dec. 20. PubMed PMID: 21173238; PubMed Central PMCID: PMC3017184.

[29] Farmer S R, Boss O (2012) Recruitment of Brown Adipose Tissue as a Therapy for Obesity-Associated Diseases. Frontiers in Endocrinology 3.

[30] Zhang N, Chen W, Zhou X, Xie X, Meng A, et al. (2013) C333H ameliorated insulin resistance through selectively modulating PPARgamma in brown adipose tissue of db/db mice. Biol Pharm Bull.

[31] Yoneshiro T, Aita S, Matsushita M, Kayahara T, Kameya T, et al. (2013) Recruited brown adipose tissue as an antiobesity agent in humans. J Clin Invest.

[32] Vijgen G H, Sparks L M, Bouvy N D, Schaart G, Hoeks J, et al. (2013) Increased Oxygen Consumption in Human Adipose Tissue From the "Brown Adipose Tissue" Region. J Clin Endocrinol Metab.

[33] Vijgen G H, van Marken Lichtenbelt WD (2013) Brown adipose tissue: clinical impact of a re-discovered thermogenic organ. Front Biosci (Elite Ed) E5: 823-833.

[34] van der Lans A A, Hoeks J, Brans B, Vijgen G H, Visser M G, et al. (2013) Cold acclimation recruits human brown fat and increases nonshivering thermogenesis. The Journal of Clinical Investigation 123: 3395-3403.

[35] Stanford K I, Middelbeek R J, Townsend K L, An D, Nygaard E B, et al. (2013) Brown adipose tissue regulates glucose homeostasis and insulin sensitivity. J Clin Invest 123: 215-223.

[36] Pasanisi F, Pace L, Fonti R, Marra M, Sgambati D, et al. (2013) Evidence of Brown Fat Activity in Constitutional Leanness. J Clin Endocrinol Metab.

[37] Yin H, Pasut A, Soleimani V D, Bentzinger C F, Antoun G, et al. (2013) MicroRNA-133 Controls Brown Adipose Determination in Skeletal Muscle Satellite Cells by Targeting Prdm16. Cell Metab 17: 210-224.

[38] Matthews D R, Hosker J P, Rudenski A S, Naylor B A, Treacher D F, and Turner R C. Homeostasis model assessment: insulin resistance and beta-cell function from fasting plasma glucose and insulin concentrations in man. Diabetologia 28: 412-419, 1985.

[39] Cannon B, Nedergaard J. Nonshivering thermogenesis and its adequate measurement in metabolic studies, J. Exp. Biol. 214 (2011), 242-253.

The invention claimed is:

1. A pharmaceutical composition comprising a therapeutically effective amount of bezafibrate as a first active ingredient, a therapeutically effective amount of a second active ingredient selected from the group consisting of oxaprozin, and a pharmaceutically acceptable carrier, wherein the therapeutically effective amount of bezafibrate ranges from about 5 mg to about 500 mg, and wherein the therapeutically effective amount of oxaprozin ranges from about 5 mg to about 500 mg.

2. The pharmaceutical composition of claim 1, wherein the therapeutically effective amount of bezafibrate ranges from about 100 mg to about 300 mg, and wherein the therapeutically effective amount of oxaprozin ranges from about 5 mg to about 500 mg.

3. The pharmaceutical composition of claim 1, wherein the therapeutically effective amount of bezafibrate ranges from about 100 mg to about 400 mg and wherein the therapeutically effective amount of oxaprozin ranges from about 5 mg to about 500 mg.

4. A method of treating a metabolic disorder in a subject comprising administering a composition of claim 1 to a subject in need thereof.

5. The method of claim 4, wherein the metabolic disorder is one or more of obesity, overweight, type II diabetes, insulin resistance, hyperinsulinemia, hyperglycemia, prediabetes, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease.

6. A method of promoting brown adipogenesis in a subject in need thereof, the method comprising administering to the subject the pharmaceutical composition of claim 1.

7. The method of claim 6, further comprising modulating a metabolic response in the subject and/or treating a metabolic disorder in the subject.

8. The method of claim 7, wherein the metabolic disorder is one or more of obesity, overweight, type II diabetes, insulin resistance, hyperinsulinemia, hyperglycemia, prediabetes, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease.

9. The method of claim 8, wherein the metabolic disorder is obesity and the pharmaceutical composition comprises a therapeutically effective amount of bezafibrate that ranges from about 100 mg to about 300 mg, and a therapeutically effective amount of oxaprozin that ranges from about 5 mg to about 500 mg.

10. The method of claim 8, wherein the metabolic disorder is obesity and the pharmaceutical composition comprises a therapeutically effective amount of bezafibrate that ranges from about 100 mg to about 400 mg and a therapeutically effective amount of oxaprozin that ranges from about 5 mg to about 500 mg.

11. The method of claim 5, wherein the metabolic disorder is obesity and the pharmaceutical composition comprises a therapeutically effective amount of bezafibrate that ranges from about 100 mg-100 mg to about 300 mg300 mg, and a therapeutically effective amount of oxaprozin that ranges from about 5 mg to about 500 mg.

12. The method of claim 5, wherein the metabolic disorder is obesity and the pharmaceutical composition comprises a therapeutically effective amount of bezafibrate that ranges from about 100 mg to about 400 mg and a therapeutically effective amount of oxaprozin that ranges from about 5 mg to about 500 mg.

* * * * *